US012740832B2

(12) United States Patent
de Souza et al.

(10) Patent No.: US 12,740,832 B2
(45) **Date of Patent: *Sep. 22, 2026**

(54) SYSTEMS AND METHODS FOR PREOPERATIVE PLANNING AND POSTOPERATIVE ANALYSIS OF SURGICAL PROCEDURES

(71) Applicant: MAKO Surgical Corp., Weston, FL (US)

(72) Inventors: Kevin Michael de Souza, Ilkley (GB); Emily Hampp, Far Hills, NJ (US); Laura Scholl, Sparta, NJ (US)

(73) Assignee: MAKO Surgical Corp., Weston, FL (US)

( * ) Notice: Subject to any disclaimer, the term of this patent is extended or adjusted under 35 U.S.C. 154(b) by 99 days.

This patent is subject to a terminal disclaimer.

(21) Appl. No.: 18/917,192

(22) Filed: Oct. 16, 2024

(65) Prior Publication Data

US 2025/0032191 A1 Jan. 30, 2025

Related U.S. Application Data

(63) Continuation of application No. 18/221,760, filed on Jul. 13, 2023, now Pat. No. 12,144,558, which is a (Continued)

(51) Int. Cl.
*A61B 34/10* (2016.01)
*A61B 34/20* (2016.01)

(52) U.S. Cl.
CPC .............. *A61B 34/10* (2016.02); *A61B 34/20* (2016.02); *A61B 2034/102* (2016.02); *A61B 2034/105* (2016.02)

(58) Field of Classification Search
CPC ... A61B 34/10; A61B 34/20; A61B 2034/102; A61B 2034/105
See application file for complete search history.

(56) References Cited

U.S. PATENT DOCUMENTS

| | | | | |
|---|---|---|---|---|
| 2004/0068187 | A1* | 4/2004 | Krause ................. | A61B 17/151 600/443 |
| 2018/0153624 | A1* | 6/2018 | Hughes .................. | A61B 34/20 |
| 2019/0029757 | A1* | 1/2019 | Roh ....................... | A61B 34/10 |

* cited by examiner

*Primary Examiner* — Michelle Chin
(74) *Attorney, Agent, or Firm* — Howard & Howard Attorneys PLLC

(57) ABSTRACT

A system for determining accuracy of a surgical procedure to implant an implant on a patient bone. The system including at least one computing device configured to perform the following steps. Receive preoperative patient data including preoperative images of the patient bone and planned implant position and orientation data. Receive postoperative patient data including postoperative images of the patient bone and an implant implanted on the patient bone. Segment the patient bone and the implant from the postoperative images of the patient bone and the implant. Register separately the patient bone and the implant from the postoperative images to the patient bone from the preoperative images. And compare an implanted position and orientation of the implant from the postoperative images relative to the patient bone from the preoperative images to the planned implant position and orientation data relative to the patient bone from the preoperative images.

19 Claims, 50 Drawing Sheets
(42 of 50 Drawing Sheet(s) Filed in Color)

Related U.S. Application Data continuation of application No. 16/713,485, filed on Dec. 13, 2019, now Pat. No. 11,737,826.

(60) Provisional application No. 62/931,982, filed on Nov. 7, 2019, provisional application No. 62/779,921, filed on Dec. 14, 2018.

SYSTEMS AND METHODS FOR PREOPERATIVE PLANNING AND POSTOPERATIVE ANALYSIS OF SURGICAL PROCEDURES

CROSS-REFERENCE TO RELATED APPLICATIONS

This application is a continuation application of U.S. application Ser. No. 18/221,760 filed Jul. 13, 2023, which application is a continuation of U.S. application Ser. No. 16/713,485 filed Dec. 13, 2019, now U.S. Pat. No. 11,737,826, which application claims the benefit of U.S. Provisional Application No. 62/931,982, filed Nov. 7, 2019, and U.S. Provisional Application No. 62/779,921, filed Dec. 14, 2018. All the above-referenced applications are hereby incorporated by reference in their entireties into the present application.

TECHNICAL FIELD

The present disclosure relates to medical systems and methods. More specifically, the present disclosure relates to preoperative planning and postoperative analysis of surgeries performed manually or by a computerized surgical system.

BACKGROUND

Modern orthopedic joint replacement surgery typically involves at least some degree of preoperative planning of the surgery in order to increase the effectiveness and efficiency of the particular procedure. In particular, preoperative planning may increase the accuracy of bone resections and implant placement while reducing the overall time of the procedure and the time the patient joint is open and exposed.

The use of robotic systems in the performance of orthopedic joint replacement surgery can greatly reduce the intraoperative time of a particular procedure. Increasingly, the effectiveness of the procedure may be based on the tools, systems, and methods utilized during the preoperative planning stages.

Examples of steps involved in preoperative planning may involve determining: implant size, position, and orientation; resection planes and depths; access trajectories to the surgical site; and others. In certain instances, the preoperative plan may involve generating a three-dimensional ("3D"), patient specific, model of the patient bone(s) and soft tissue to undergo the joint replacement. The 3D patient model may be used as a visual aid in planning the various possibilities of implant sizes, implant orientations, implant positions, and corresponding resection planes and depths, among other parameters.

After the surgery is performed, postoperative analysis of the patient can help determine if the results of the surgery are according to the plan.

While the framework for certain aspects of preoperative planning and postoperative analysis may be known in the art, there is a need for tools, systems, and methods to further refine certain aspects of preoperative planning to further increase efficiency and effectiveness in robotic and robotic-assisted orthopedic joint replacement surgery.

SUMMARY

Aspects of the present disclosure may include a system for determining accuracy of a surgical procedure to implant an implant on a patient bone. The system may include at least one computing device configured to perform the following steps. Receive preoperative patient data may include preoperative images of the patient bone and planned implant position and orientation data. Receive postoperative patient data may include postoperative images of the patient bone and an implant implanted on the patient bone, the postoperative images having been generated after the preoperative images and after the surgical procedure to implant the implant on the patient bone. From the postoperative images of the patient bone and the implant, segment the patient bone. From the postoperative images of the patient bone and the implant, segment the implant. Register the patient bone from the postoperative images to the patient bone from the preoperative images. Register the implant from the postoperative images to the patient bone from the preoperative images. And compare an implanted position and orientation of the implant from the postoperative images relative to the patient bone from the preoperative images to the planned implant position and orientation data relative to the patient bone from the preoperative images.

In certain instances, the at least one computing device is further configured to determine the accuracy of the surgical procedure by computing a difference between the implanted position and orientation and the planned implant position and orientation data.

In certain instances, the at least one computing device is further configured to display the implant from the postoperative images overlaid on the patient bone from the preoperative images on a display screen.

In certain instances, the at least one computing device is further configured to generate a three-dimensional bone model of the patient bone from the preoperative images.

In certain instances, the at least one computing device is further configured to generate a postoperative three-dimensional bone model from the postoperative images of the patient bone and the implant where the patient bone was segmented.

In certain instances, the postoperative three-dimensional bone model includes a void corresponding to a location of the implant.

In certain instances, the patient bone may include a femur. In certain instances, the implant may include a total-knee femoral implant. In certain instances, the implant may include a partial-knee femoral implant. In certain instances, the patient bone may include a tibia. In certain instances, the implant may include a total-knee tibia implant. In certain instances, the implant may include a partial-knee tibia implant. In certain instances, the patient bone may include at least one of a femur, a tibia, or an ilium.

In certain instances, the at least one computing device is further configured to label discrete portions of the postoperative images as corresponding to implant. In certain instances, the discrete portions may include voxels of the postoperative images. In certain instances, the discrete portions of the postoperative images are labeled as corresponding to implant based on voxel classification.

In certain instances, segmenting the patient bone from the postoperative images of the patient bone and the implant may include using an Active Appearance Model (AAM). In certain instances, the AAM is configured to disregard the discrete portions of the postoperative images as corresponding to implant so as to only segment portions of the postoperative images corresponding to bone.

In certain instances, the system further may include a surgical navigation system in communication with the at least one computing device. In certain instances, the system further may include a surgical robot in communication with the at least one computing device.

Aspects of the present disclosure may include a computer program stored on one or more tangible, non-transitory, computer-readable storage media having executable instructions for performing the computer program on a computing system. The computer program may include the following steps. Receiving postoperative patient data that may include postoperative image data of a patient bone with an implant implanted thereon. Performing a first segmentation operation isolating the patient bone from the implant in the postoperative image data. Performing a second segmentation operation isolating the implant from the patient bone in the postoperative image data. Registering the patient bone from the first segmentation operation to preoperative image data that is representative of the patient bone prior to implantation of the implant. Registering the implant from the second segmentation operation to the preoperative image data that is representative of the patient bone prior to implantation of the implant. Comparing an implanted position and orientation of the implant registered to the preoperative image data to preoperatively planned implant position and orientation data.

In certain instances, the computer program further may include labeling discrete portions of the postoperative image data as corresponding to implant. In certain instances, the discrete portions may include voxels of the postoperative image data. In certain instances, the discrete portions of the postoperative image data are labeled as corresponding to implant based on voxel intensity.

In certain instances, the first segmentation operation isolating the patient bone from the implant in the postoperative image data is performed using an Active Appearance Model (AAM). In certain instances, the AAM is configured to disregard the discrete portions of the postoperative image data so as to segment only bone.

Aspects of the present disclosure may include a computerized method of registering postoperative patient data and preoperative patient data. The computerized method may include the following steps. Receiving postoperative patient data that may include postoperative image data of a patient bone with an implant implanted thereon. Performing a first segmentation operation separating the patient bone from the implant in the postoperative image data. Performing a second segmentation operation separating the implant from the patient bone in the postoperative image data. Registering the patient bone from the first segmentation operation to preoperative image data of the patient bone prior to implantation of the implant. Registering the implant from the second segmentation operation to preoperative image data of the patient bone prior to implantation of the implant. Comparing an implanted position and orientation of the implant registered to the preoperative image data to preoperatively planned implant position and orientation data.

In certain instances, the computerized method further may include labeling discrete portions of the postoperative image data as either corresponding to bone or corresponding to implant. In certain instances, the discrete portions may include voxels of the postoperative image data. In certain instances, the discrete portions of the postoperative image data are labeled as either corresponding to bone or corresponding to implant based on voxel intensity.

In certain instances, the first segmentation operation isolating the patient bone from the implant in the postoperative image data is performed using an Active Appearance Model (AAM). In certain instances, the AAM is configured to disregard the discrete portions of the postoperative image data so as to segment only bone.

In certain instances, the computerized method further may include planning a revision surgery based on results of comparing the implanted position and orientation of the implant registered to the preoperative image data and the preoperatively planned implant position and orientation data.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
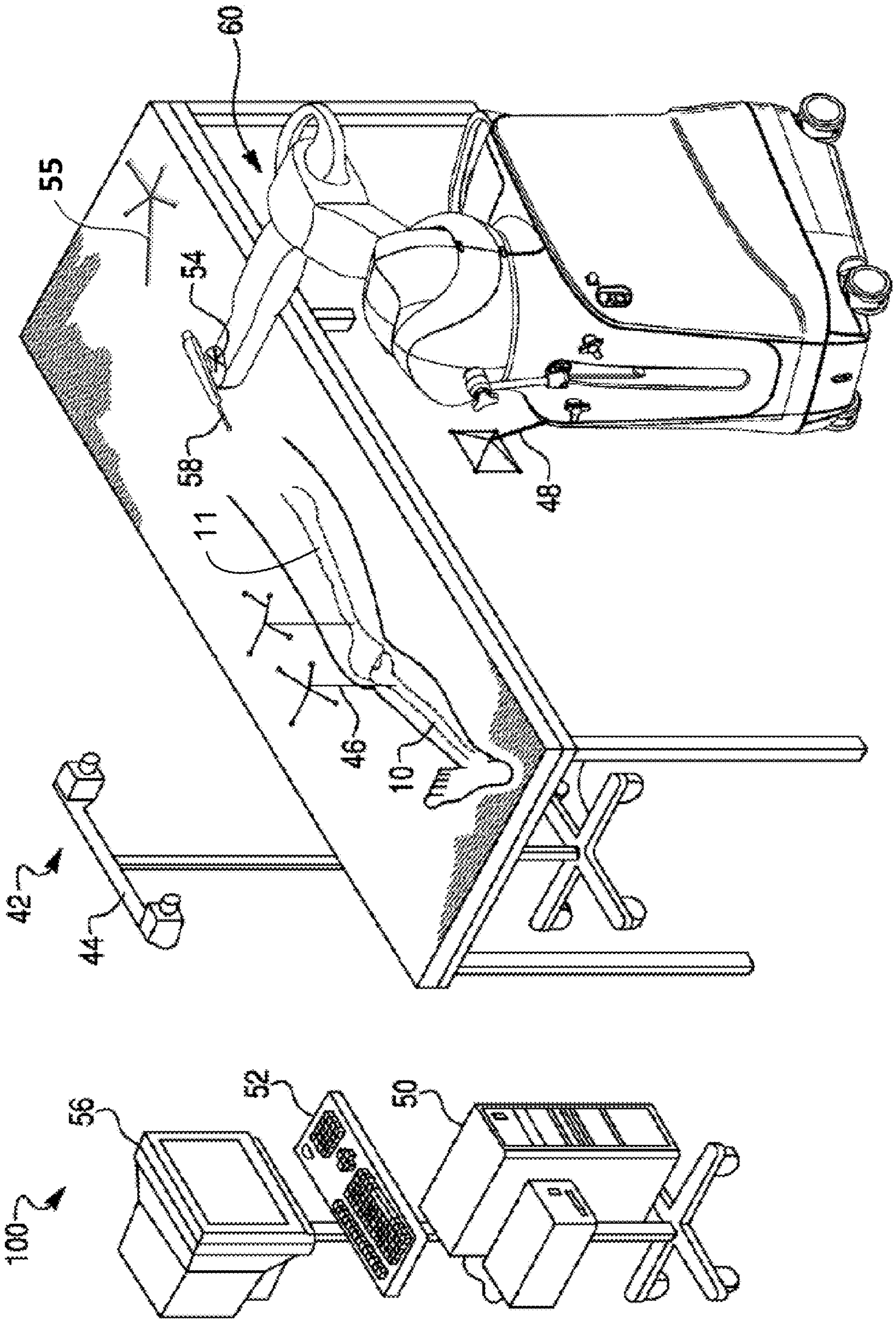
FIG. 1 is an illustration of a surgical system.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein. The term "comprising" means "including, but not necessarily limited to"; it specifically indicates open-ended inclusion or membership in a so-described combination, group, series and the like.

The present application incorporates by reference the following applications in their entireties: International Application PCT/US2017/049466, filed Aug. 30, 2017, entitled "SYSTEMS AND METHODS FOR INTRA-OPERATIVE PELVIC REGISTRATION"; PCT/US2016/034847 filed May 27, 2016, entitled "PREOPERATIVE PLANNING AND ASSOCIATED INTRAOPERATIVE REGISTRATION FOR A SURGICAL SYSTEM"; U.S. patent application Ser. No. 12/894,071, filed Sep. 29, 2010, entitled "SURGICAL SYSTEM FOR POSITIONING PROSTHETIC COMPONENT AND/OR FOR CONSTRAINING MOVEMENT OF SURGICAL TOOL"; U.S. patent application Ser. No. 13/234,190, filed Sep. 16, 2011, entitled "SYSTEMS AND METHOD FOR MEASURING PARAMETERS IN JOINT REPLACEMENT SURGERY"; U.S. patent application Ser. No. 11/357,197, filed Feb. 21, 2006, entitled "HAPTIC GUIDANCE SYSTEM AND METHOD"; U.S. patent application Ser. No. 12/654,519, filed Dec. 22, 2009, entitled "TRANSMISSION WITH FIRST AND SECOND TRANSMISSION ELEMENTS"; U.S. patent application Ser. No. 12/644,964, filed Dec. 22, 2009, entitled "DEVICE THAT CAN BE ASSEMBLED BY COUPLING"; and U.S. patent application Ser. No. 11/750,807, filed May 18, 2007, entitled "SYSTEM AND METHOD FOR VERIFYING CALIBRATION OF A SURGICAL DEVICE".

Preoperative planning of arthroplasty surgical procedures for execution via a surgical system 100 is disclosed herein. The preoperative planning may include, for example, defining bone resection depths and identifying whether or not unacceptable notching of the femoral anterior cortex is associated with the proposed bone resection depths and proposed pose of the candidate implants. Assuming the preoperatively planned bone resection depths and implant poses are free of unacceptable notching of the femoral anterior cortex and approved by the surgeon, the bone resection depths can be updated to account for cartilage thickness by intraoperatively registering the cartilage condylar surfaces of the actual patient bones to the patient bone models employed in the preoperative planning. By so accounting for the cartilage thickness, the actual implants, upon implantation via the surgical system 100, will have their respective condylar surfaces located so as to act in place of the resected cartilage condylar surfaces of the actual patient bones.

Before beginning a detailed discussion of the preoperative planning and the intraoperative registering of the cartilage condylar surface, an overview of the surgical system and its operation will now be given as follows.

I. Overview of Surgical System

To begin a detailed discussion of the surgical system, reference is made to FIG. 1. As can be understood from FIG. 1, the surgical system 100 includes a navigation system 42, a computer 50, and a haptic device or robot 60. The navigation system tracks the patient's bone (i.e., tibia 10, femur 11), as well as surgical tools (e.g., pointer device, probe, cutting tool) utilized during the surgery, to allow the surgeon to visualize the bone and tools on a display 56 during the osteotomy procedure. And while the system 100 is described as including a robot 60 and a navigation system 42, the system 100 may perform certain functions described herein with only the computer 50. For example, certain preoperative planning methods and postoperative analysis methods may be performed using on a computer 50.

The navigation system 42 may be any type of navigation system configured to track the pose (i.e. position and orientation) of a bone. For example, the navigation system 42 may include a non-mechanical tracking system, a mechanical tracking system, or any combination of non-mechanical and mechanical tracking systems. The navigation system 42 includes a detection device 44 that obtains a pose of an object with respect to a coordinate frame of reference of the detection device 44. As the object moves in the coordinate frame of reference, the detection device tracks the pose of the object to detect movement of the object.

In one embodiment, the navigation system 42 includes a non-mechanical tracking system as shown in FIG. 1. The non-mechanical tracking system is an optical tracking system with a detection device 44 and a trackable element (e.g. navigation marker 46) that is disposed on a tracked object and is detectable by the detection device 44. In one embodiment, the detection device 44 includes a visible light-based detector, such as a MicronTracker (Claron Technology Inc., Toronto, Canada), that detects a pattern (e.g., a checkerboard pattern) on a trackable element. In another embodiment, the detection device 44 includes a stereo camera pair sensitive to infrared radiation and positionable in an operating room where the arthroplasty procedure will be performed. The trackable element is affixed to the tracked object in a secure and stable manner and includes an array of markers having a known geometric relationship to the tracked object. As is known, the trackable elements may be active (e.g., light emitting diodes or LEDs) or passive (e.g., reflective spheres, a checkerboard pattern, etc.) and have a unique geometry (e.g., a unique geometric arrangement of the markers) or, in the case of active, wired or wireless markers, a unique firing pattern. In operation, the detection device 44 detects positions of the trackable elements, and the surgical system 100 (e.g., the detection device 44 using embedded electronics) calculates a pose of the tracked object based on the trackable elements' positions, unique geometry, and known geometric relationship to the tracked object. The tracking system 42 includes a trackable element for each object the user desires to track, such as the navigation marker 46 located on the bone 10. During haptically guided robotic-assisted surgeries, the navigation system may further include a haptic device marker 48 (to track a global or gross position of the haptic device 60), an end effector marker 54 (to track a distal end of the haptic device 60), and a free-hand navigation probe 55 for use in the registration process.

As indicated in FIG. 1, the surgical system 100 further includes a processing circuit, represented in the figures as a computer 50. The processing circuit includes a processor and memory device. The processor can be implemented as a general purpose processor, an application specific integrated circuit (ASIC), one or more field programmable gate arrays (FPGAs), a group of processing components, a purpose-specific processor, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes, layers and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit and includes computer code for executing (e.g., by the processing circuit and/or processor) one or more processes described herein.

The computer 50 is configured to communicate with the navigation system 42 and the haptic device 60. Furthermore, the computer 50 may receive information related to orthopedic/arthroplasty procedures and perform various functions related to performance of osteotomy procedures. For example, the computer 50 may have software as necessary to perform functions related to image analysis, surgical planning, registration, navigation, image guidance, and haptic guidance. More particularly, the navigation system may operate in conjunction with an autonomous robot or a surgeon-assisted device (haptic device) in performing the arthroplasty procedure.

Figure 2:
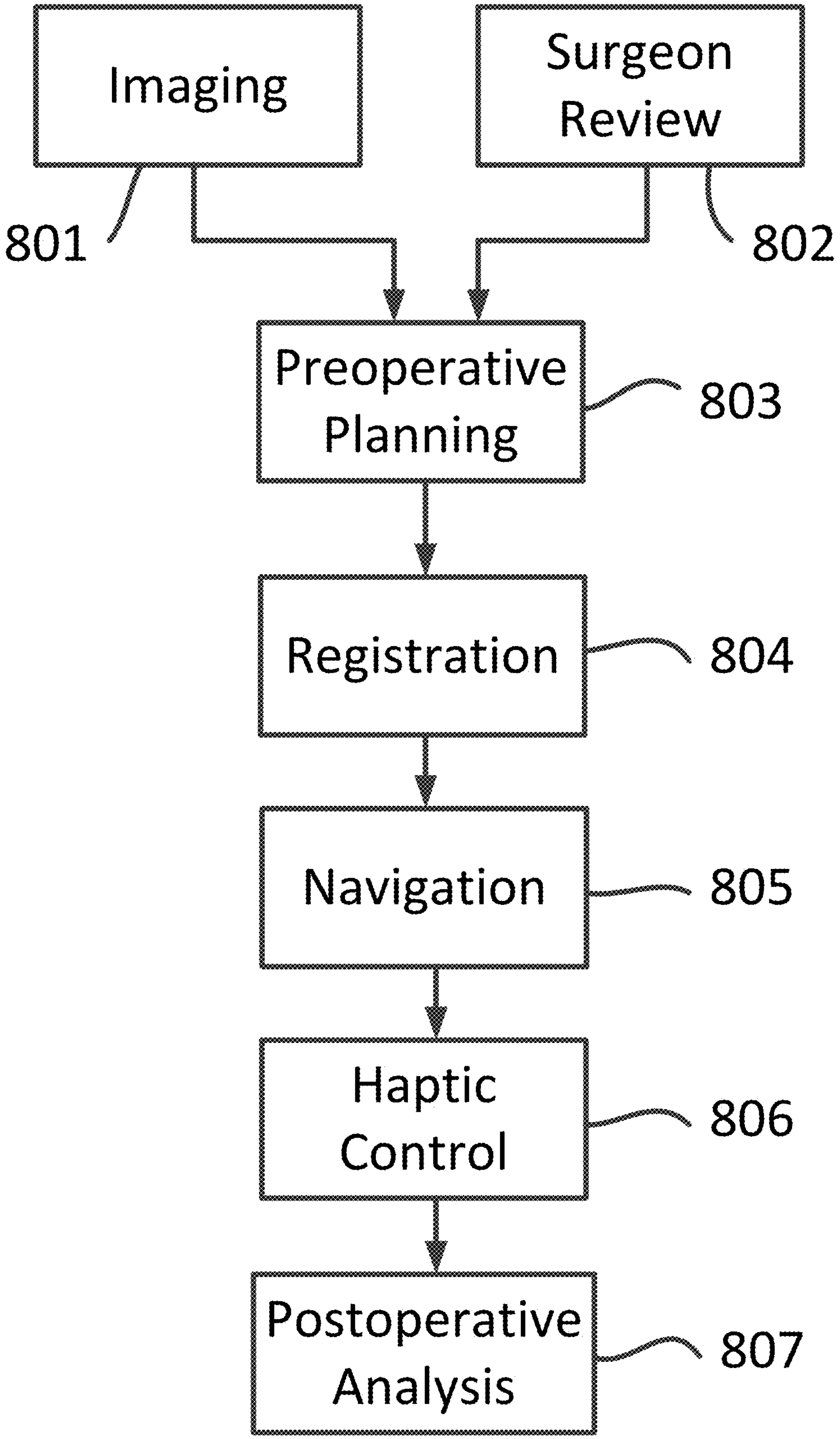
FIG. 2 is a flow chart illustrating surgical planning and performance of an arthroplasty.

The computer 50 receives images of the patient's anatomy on which an arthroplasty procedure is to be performed. Referring to FIG. 2, prior to performance of an arthroplasty, the patient's anatomy is scanned using any known imaging technique, such as CT or MRI (Step 801) captured with a medical imaging machine. And while the disclosure makes reference to medical images captured or generated with a medical imaging machine such as a CT or MRI machine, other methods of generating the medical images are possible and contemplated herein. For example, an image of the bone may be generated intra-operatively via a medical imaging machine such as a hand-held scanning or imaging device that scans or registers the topography of the bone surface (e.g., ultrasound). Thus, the term medical imaging machine is intended to encompass devices of various size (e.g., C-arm, hand-held device), located at imaging centers or used intra-operatively.

Continuing on, the scan data is then segmented to obtain a three-dimensional representation of the patient's anatomy. For example, prior to performance of a knee arthroplasty, a three-dimensional representation of the femur and tibia is created. Using the three-dimensional representation and as part of the planning process, femoral and tibial landmarks can be selected, and the patient's femoral-tibial alignment is calculated along with the orientation and placement of the proposed femoral and tibial implants, which may be selected as to model and size via the computer 50. The femoral and tibial landmarks may include the femoral head center, the distal trochlear groove, the center of intercondylar eminence, the tibia-ankle center, and the medial tibial spine, among others. The femoral-tibial alignment is the angle between the femur mechanical axis (i.e., line from femoral head center to distal trochlear groove) and the tibial mechanical axis (i.e., line from ankle center to intercondylar eminence center). Based on the patient's current femoral-tibial alignment and the desired femoral-tibial alignment to be achieved by the arthroplasty procedure and further including the size, model and placement of the proposed femoral and tibial implants, including the desired extension, varus-valgus angle, and internal-external rotation associated with the implantation of the proposed implants, the computer 50 is programmed to calculate the desired implantation of the proposed implants or at least assist in the preoperative planning of the implantation of the proposed implants, including the resections to be made via the haptic device 60 in the process of performing the arthroplasty procedure (Step 803). The preoperative plan achieved via Step 803 is provided to the surgeon for review, adjustment and approval, and the preoperative plan is updated as directed by the surgeon (Step 802).

Since the computer 50 is used to develop a surgical plan according to Step 803, it should be understood that a user can interact with the computer 50 at any stage during surgical planning to input information and modify any portion of the surgical plan. The surgical plan may include a plurality of planned virtual boundaries. The virtual boundaries can represent holes and/or cuts to be made in a bone 10, 11 during an arthroplasty procedure. Once the surgical plan has been developed, a haptic device 60 is used to assist a user in creating the planned holes and cuts in the bones 10, 11. Preoperative planning, especially with respect to bone resection depth planning and the prevention of femoral anterior shaft notching, will be explained more fully below.

The drilling of holes and creation of cuts or resections in bones 10, 11 can be accomplished with the assistance of a haptically guided interactive robotic system, such as the haptic guidance system described in U.S. Pat. No. 8,010,180, titled "Haptic Guidance System and Method," granted Aug. 30, 2011, and hereby incorporated by reference herein in its entirety. As the surgeon manipulates a robotic arm to drill holes in the bone or perform cuts with a high speed drill, sagittal saw, or other suitable tool, the system provides haptic feedback to guide the surgeon in sculpting the holes and cuts into the appropriate shape, which is pre-programmed into the control system of the robotic arm. Haptic guidance and feedback will be explained more fully below.

During surgical planning, the computer 50 further receives information related to femoral and tibial implants to be implanted during the arthroplasty procedure. For example, a user may input parameters of selected femoral and tibial implants into the computer 50 using the input device 52 (e.g. keyboard, mouse, etc.). Alternatively, the computer 50 may contain a pre-established database of various implants and their parameters, and a user can choose the selected implants from the database. In a still further embodiment, the implants may be custom designed based on a patient-specific surgical plan. Selection of the implants may occur during any stage of surgical planning.

The surgical plan may further be based on at least one parameter of the implants or a function of a parameter of the implants. Because the implants can be selected at any stage of the surgical planning process, the implants may be selected prior to or after determination of the planned virtual boundaries by the computer 50. If the implants are selected first, the planned virtual boundaries may be based at least in part on a parameter of the implants. For example, the distance (or any other relationship) between the planned virtual boundaries representing holes or cuts to made in the bones 10, 11 may be planned based on the desired varus-valgus femoral-tibial alignment, extension, internal-external rotation, or any other factors associated with a desired surgical outcome of the implantation of the arthroplasty implants. In this manner, implementation of the surgical plan will result in proper alignment of the resected bone surfaces and holes to allow the selected implants to achieve the desired surgical outcome. Alternatively, the computer 50 may develop the surgical plan, including the planned virtual boundaries, prior to implant selection. In this case, the implant may be selected (e.g. input, chosen, or designed) based at least in part on the planned virtual boundaries. For example, the implants can be selected based on the planned virtual boundaries such that execution of the surgical plan will result in proper alignment of the resected bone surfaces and holes to allow the selected implants to achieve the desired surgical outcome.

The virtual boundaries exist in virtual space and can be representative of features existing or to be created in physical (i.e. real) space. Virtual boundaries correspond to working boundaries in physical space that are capable of interacting with objects in physical space. For example, working boundaries can interact with a surgical tool 58 coupled to haptic device 60. Although the surgical plan is often described herein to include virtual boundaries representing holes and resections, the surgical plan may include virtual boundaries representing other modifications to a bone 10, 11. Furthermore, virtual boundaries may correspond to any working boundary in physical space capable of interacting with objects in physical space.

Referring again to FIG. 2, after surgical planning and prior to performing an arthroplasty procedure, the physical anatomy (e.g. bones 10, 11) is registered to a virtual representation of the anatomy (e.g. a preoperative three-dimensional representation) using any known registration technique (Step 804). Possible registration techniques include the point-based registration technique described in above-referenced U.S. Pat. No. 8,010,180, or 2D/3D registration utilizing a hand-held radiographic imaging device as described in U.S. application Ser. No. 13/562,163, titled "Radiographic Imaging Device," filed Jul. 30, 2012, and hereby incorporated by reference herein in its entirety. Registration of the patient's anatomy allows for accurate navigation during the surgical procedure (Step 805), which enables each of the virtual boundaries to correspond to a working boundary in physical space. For example, referring to FIGS. 3A and 3B, a virtual boundary 62 representing a resection in a tibia bone 10 is displayed on a computer or other display 63 and the virtual boundary 62 corresponds to a working boundary 66 in physical space 69, such as a surgery site in a surgical operating room. A portion of working boundary 66 in turn corresponds to the planned location of the resection in the tibia 10.

Figure 3B:
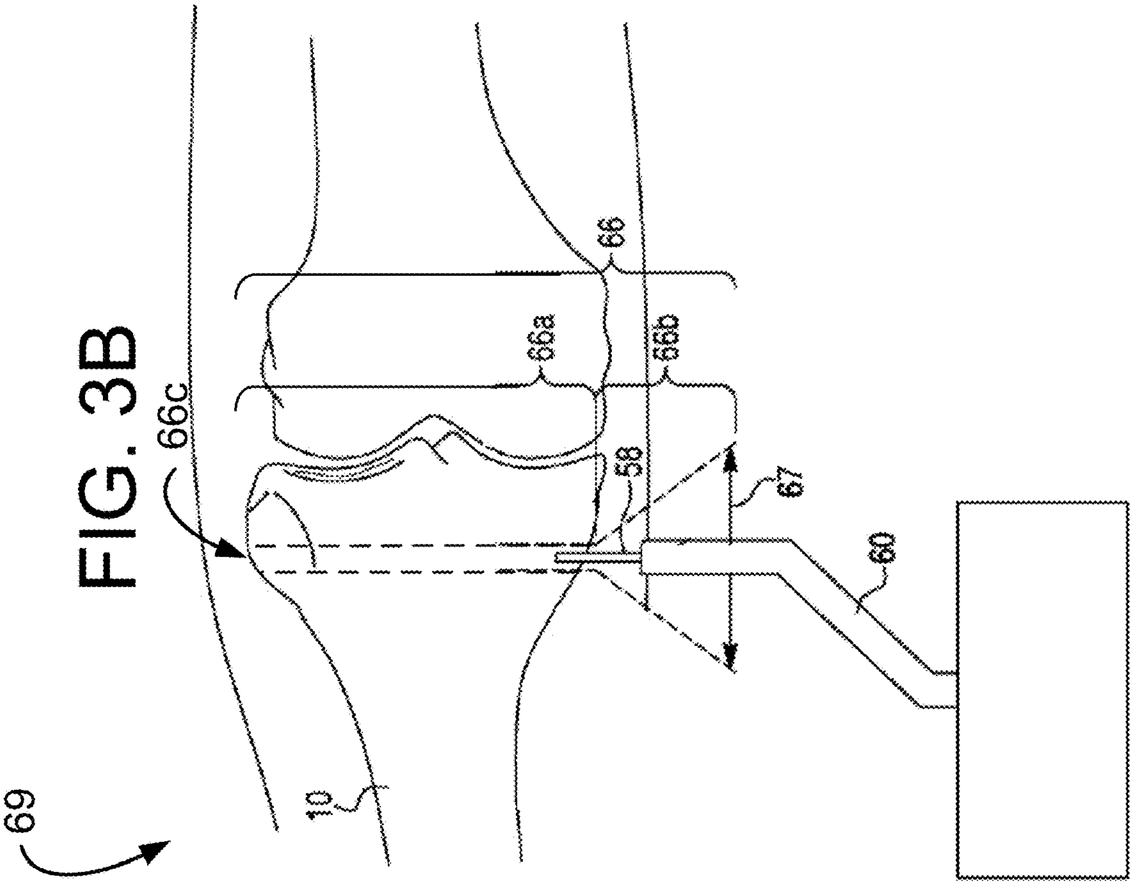
FIGS. 3A and 3B illustrate haptic guidance during performance of an arthroplasty.
Figure 3A:
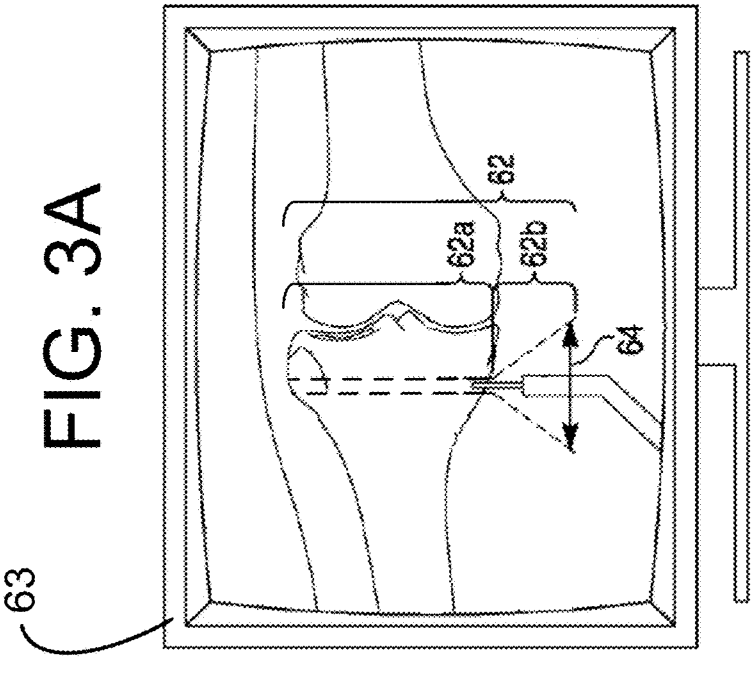

The virtual boundaries and, therefore, the corresponding working boundaries, can be any configuration or shape. Referring to FIG. 3A, virtual boundary 62 representing a proximal resection to be created in the tibia bone 10, may be any configuration suitable for assisting a user during creation of the proximal resection in the tibia 10. Portions of virtual boundary 62, illustrated within the virtual representation of the tibia bone 10, represent bone to be removed by a surgical tool. Similar virtual boundaries may be generated for holes to be drilled or milled into the tibia bone 10 for facilitating the implantation of a tibial implant on the resected tibia 10. The virtual boundaries (and therefore, the corresponding working boundaries) may include a surface or surfaces that fully enclose and surround a three-dimensional volume. In an alternative embodiment, the virtual and working boundaries do not fully enclose a three-dimensional volume, but rather include both "active" surfaces and "open" portions. For example, virtual boundary 62 representing a proximal resection in a tibia bone may have an essentially rectangular box-shaped "active" surface 62*a* and a collapsing funnel or triangular box-shaped "active" surface 62*b* connected to the rectangular box-shaped portion, with an "open" portion 64. In one embodiment, virtual boundary 62 can be created with a collapsing funnel as described in U.S. application Ser. No. 13/340,668, titled "Systems and Methods for Selectively Activating Haptic Guide Zones," filed Dec. 29, 2011, and hereby incorporated by reference herein in its entirety. The working boundary 66 corresponding to virtual boundary 62 has the same configuration as virtual boundary 62. In other words, working boundary 66 guiding a proximal resection in a tibia bone 10 may have an essentially rectangular box-shaped "active" surface 66*a* and a collapsing funnel or triangular box-shaped "active" surface 66*b* connected to the rectangular box-shaped portion, with an "open" portion 67.

In an additional embodiment, the virtual boundary 62 representing the resection in the bone 10 includes only the substantially rectangular box-shaped portion 62 *a*. An end of a virtual boundary having only a rectangular box-shaped portion may have an "open" top such that the open top of the corresponding working boundary coincides with the outer surface of the bone 10. Alternatively, as shown in FIGS. 3A and 3B, the rectangular box-shaped working boundary portion 66 *a* corresponding to virtual boundary portion 62 *a* may extend past the outer surface of the bone 10.

In some embodiments, the virtual boundary 62 representing a resection through a portion of the bone may have an essentially planar shape, with our without a thickness. Alternatively, virtual boundary 62 can be curved or have an irregular shape. Where the virtual boundary 62 is depicted as a line or planar shape and the virtual boundary 62 also has a thickness, the virtual boundary 62 may be slightly thicker than a surgical tool used to create the resection in the bone, such that the tool can be constrained within the active surfaces of working boundary 66 while within the bone. Such a linear or planar virtual boundary 62 may be planned such that the corresponding working boundary 66 extends past the outer surface of the bone 10 in a funnel or other appropriate shape to assist a surgeon as the surgical tool 58 is approaching the bone 10. Haptic guidance and feedback (as described below) can be provided to a user based on relationships between surgical tool 58 and the active surfaces of working boundaries.

The surgical plan may also include virtual boundaries to facilitate entry into and exit from haptic control, including automatic alignment of the surgical tool, as described in U.S. application Ser. No. 13/725,348, titled "Systems and Methods for Haptic Control of a Surgical Tool," filed Dec. 21, 2012, and hereby incorporated by reference herein in its entirety.

The surgical plan, including the virtual boundaries, may be developed based on information related to the patient's bone density. The density of a patient's bone is calculated using data obtained from the CT, MRI, or other imaging of the patient's anatomy. In one embodiment, a calibration object representative of human bone and having a known calcium content is imaged to obtain a correspondence between image intensity values and bone density measurements. This correspondence can then be applied to convert intensity values of individual images of the patient's anatomy into bone density measurements. The individual images of the patient's anatomy, with the corresponding map of bone density measurements, are then segmented and used to create a three-dimensional representation (i.e. model) of the patient's anatomy, including the patient's bone density information. Image analysis, such as finite element analysis (FEA), may then be performed on the model to evaluate its structural integrity.

The ability to evaluate the structural integrity of the patient's anatomy improves the effectiveness of arthroplasty planning. For example, if certain portions of the patient's bone appear less dense (i.e. osteoporotic), the holes, resections and implant placement can be planned to minimize the risk of fracture of the weakened portions of bone. Furthermore, the planned structure of the bone and implant combination after implementation of the surgical plan (e.g. the post-operative bone and implant arrangement) can also be evaluated for structural integrity, pre-operatively, to improve surgical planning. In this embodiment, holes and/or cuts are planned and the bone model and implant model are manipulated to represent the patient's bone and implant arrangement after performance of the arthroplasty and implantation procedures. Various other factors affecting the structural integrity of the post-operative bone and implant arrangement may be taken into account, such as the patient's weight and lifestyle. The structural integrity of the post-operative bone and implant arrangement is analyzed to determine whether the arrangement will be structurally sound and kinematically functional post-operatively. If the analysis uncovers structural weaknesses or kinematic concerns, the surgical plan can be modified to achieve a desired post-operative structural integrity and function.

Once the surgical plan has been finalized, a surgeon may perform the arthroplasty procedure with the assistance of haptic device 60 (step 806). Through haptic device 60, the surgical system 100 provides haptic guidance and feedback to the surgeon to help the surgeon accurately implement the surgical plan. Haptic guidance and feedback during an arthroplasty procedure allows for greater control of the surgical tool compared to conventional arthroplasty techniques, resulting in more accurate alignment and placement of the implant. Furthermore, haptic guidance and feedback is intended to eliminate the need to use K-wires and fluoroscopy for planning purposes. Instead, the surgical plan is created and verified using the three-dimensional representation of the patient's anatomy, and the haptic device provides guidance during the surgical procedure.

"Haptic" refers to a sense of touch, and the field of haptics relates to human interactive devices that provide tactile and/or force feedback to an operator. Tactile feedback generally includes tactile sensations such as, for example, vibration. Force feedback (also known as "wrench") refers to feedback in the form of force (e.g., resistance to movement) and/or torque. Wrench includes, for example, feedback in the form of force, torque, or a combination of force and torque. Haptic feedback may also encompass disabling or altering the amount of power provided to the surgical tool, which can provide tactile and/or force feedback to the user.

Surgical system 100 provides haptic feedback to the surgeon based on a relationship between surgical tool 58 and at least one of the working boundaries. The relationship between surgical tool 58 and a working boundary can be any suitable relationship between surgical tool 58 and a working boundary that can be obtained by the navigation system and utilized by the surgical system 100 to provide haptic feedback. For example, the relationship may be the position, orientation, pose, velocity, or acceleration of the surgical tool 58 relative to one or more working boundaries. The relationship may further be any combination of position, orientation, pose, velocity, and acceleration of the surgical tool 58 relative to one or more working boundaries. The "relationship" between the surgical tool 58 and a working boundary may also refer to a quantity or measurement resulting from another relationship between the surgical tool 58 and a working boundary. In other words, a "relationship" can be a function of another relationship. As a specific example, the "relationship" between the surgical tool 58 and a working boundary may be the magnitude of a haptic force generated by the positional relationship between the surgical tool 58 and a working boundary.

During operation, a surgeon manipulates the haptic device 60 to guide a surgical tool 58 coupled to the device. The surgical system 100 provides haptic feedback to the user, through haptic device 60, to assist the surgeon during creation of the planned holes, cuts, or other modifications to the patient's bone needed to facilitate implantation of the femoral and tibial implants. For example, the surgical system 100 may assist the surgeon by substantially preventing or constraining the surgical tool 58 from crossing a working boundary. The surgical system 100 may constrain the surgical tool from crossing a working boundary by any number and combination of haptic feedback mechanisms, including by providing tactile feedback, by providing force feedback, and/or by altering the amount of power provided to the surgical tool. "Constrain," as used herein, is used to describe a tendency to restrict movement. Therefore, the surgical system may constrain the surgical tool 58 directly by applying an opposing force to the haptic device 60, which tends to restrict movement of the surgical tool 58. The surgical system may also constrain the surgical tool 58 indirectly by providing tactile feedback to alert a user to change his or her actions, because alerting a user to change his or her actions tends to restrict movement of the surgical tool 58. In a still further embodiment, the surgical system 100 may constrain the surgical tool 58 by limiting power to the surgical tool 58, which again tends to restrict movement of the tool.

In various embodiments, the surgical system 100 provides haptic feedback to the user as the surgical tool 58 approaches a working boundary, upon contact of the surgical tool 58 with the working boundary, and/or after the surgical tool 58 has penetrated the working boundary by a predetermined depth. The surgeon may experience the haptic feedback, for example, as a vibration, as a wrench resisting or actively opposing further movement of the haptic device, or as a solid "wall" substantially preventing further movement of the haptic device. The user may alternatively experience the haptic feedback as a tactile sensation (e.g. change in vibration) resulting from alteration of power provided to the surgical tool 58, or a tactile sensation resulting from cessation of power provided to the tool. If power to the surgical tool is altered or stopped when the surgical tool 58 is drilling, cutting, or otherwise operating directly on bone, the surgeon will feel haptic feedback in the form of resistance to further movement because the tool is no longer able to drill, cut, or otherwise move through the bone. In one embodiment, power to the surgical tool is altered (e.g. power to the tool is decreased) or stopped (e.g. the tool is disabled) upon contact between the surgical tool 58 and a working boundary. Alternatively, the power provided to the surgical tool 58 may be altered (e.g. decreased) as the surgical tool 58 approaches a working boundary.

In another embodiment, the surgical system 100 may assist the surgeon in creating the planned holes, cuts, and other modifications to the bone by providing haptic feedback to guide the surgical tool 58 towards or along a working boundary. As one example, the surgical system 100 may provide forces to the haptic device 60 based on a positional relationship between the tip of surgical tool 58 and the closest coordinates of a working boundary. These forces may cause the surgical tool 58 to approach the closest working boundary. Once the surgical tool 58 is substantially near to or contacting the working boundary, the surgical system 100 may apply forces that tend to guide the surgical tool 58 to move along a portion of the working boundary. In another embodiment, the forces tend to guide the surgical tool 58 to move from one portion of the working boundary to another portion of a working boundary (e.g. from a funnel-shaped portion of the working boundary to a rectangular box-shaped portion of a working boundary).

In yet another embodiment, the surgical system 100 is configured to assist the surgeon in creating the planned holes, cuts, and modifications to the bone by providing haptic feedback to guide the surgical tool from one working boundary to another working boundary. For example, the surgeon may experience forces tending to draw the surgical tool 58 towards working boundary 66 when the user guides the surgical tool 58 towards working boundary 66. When the user subsequently removes the surgical tool 58 from the space surrounded by working boundary 66 and manipulates the haptic device 60 such that the surgical tool 58 approaches a second working boundary (not shown), the surgeon may experience forces pushing away from working boundary 66 and towards the second working boundary.

Haptic feedback as described herein may operate in conjunction with modifications to the working boundaries by the surgical system 100. Although discussed herein as modifications to "working boundaries," it should be understood that the surgical system 100 modifies the virtual boundaries, which correspond to the working boundaries. Some examples of modifications to a working boundary include: 1) reconfiguration of the working boundary (e.g. a change in shape or size), and 2) activating and deactivating the entire working boundary or portions of the working boundary (e.g. converting "open" portions to "active" surfaces and converting "active" surfaces to "open" portions). Modifications to working boundaries, similarly to haptic feedback, may be performed by the surgical system 100 based on a relationship between the surgical tool 58 and one or more working boundaries. Modifications to the working boundaries further assist a user in creating the required holes and cuts during an arthroplasty procedure by facilitating a variety of actions, such as movement of the surgical tool 58 towards a bone and cutting of the bone by the surgical tool 58.

In one embodiment, modifications to the working boundary facilitate movement of the surgical tool 58 towards a bone 10. During a surgical procedure, because the patient's anatomy is tracked by the navigation system, the surgical system 100 moves the entirety of working boundary 66 in correspondence with movement of the patient's anatomy. In addition to this baseline movement, portions of working boundary 66 may be reshaped and/or reconfigured to facilitate movement of the surgical tool 58 towards the bone 10. As one example, the surgical system may tilt funnel-shaped portion 66 *b* of working boundary 66 relative to the rectangular box-shaped portion 66 *a* during the surgical procedure based on a relationship between the surgical tool 58 and the working boundary 66. The working boundary 66 can therefore be dynamically modified during the surgical procedure such that the surgical tool 58 remains within the space surrounded by the portion 66 *b* of working boundary 66 as the surgical tool 58 approaches the bone 10.

In another embodiment, working boundaries or portions of working boundaries are activated and deactivated. Activating and deactivating entire working boundaries may assist a user when the surgical tool 58 is approaching the bone 10. For example, a second working boundary (not shown) may be deactivated during the time when the surgeon is approaching the first working boundary 66 or when the surgical tool 58 is within the space surrounded by the first working boundary 66. Similarly, the first working boundary 66 may be deactivated after the surgeon has completed creation of a first corresponding resection and is ready to create a second resection. In one embodiment, working boundary 66 may be deactivated after surgical tool 58 enters the area within the funnel-portion leading to the second working boundary but is still outside of first funnel-portion 66 *b*. Activating a portion of a working boundary converts a previously open portion (e.g. open top 67) to an active surface of the working boundary. In contrast, deactivating a portion of the working boundary converts a previously active surface (e.g. the end portion 66 *c* of working boundary 66) of the working boundary to an "open" portion.

Activating and deactivating entire working boundaries or their portions may be accomplished dynamically by the surgical system 100 during the surgical procedure. In other words, the surgical system 100 may be programmed to determine, during the surgical procedure, the presence of factors and relationships that trigger activation and deactivation of virtual boundaries or portions of the virtual boundaries. In another embodiment, a user can interact with the surgical system 100 (e.g. by using the input device 52) to denote the start or completion of various stages of the arthroplasty procedure, thereby triggering working boundaries or their portions to activate or deactivate.

In view of the operation and function of the surgical system 100 as described above, the discussion will now turn to methods of preoperatively planning the surgery to be performed via the surgical system 100, followed by a detailed discussion of methods of registering the preoperative plan to the patient's actual bone and also to applicable components of the surgical system 100.

The haptic device 60 may be described as a surgeon-assisted device or tool because the device 60 is manipulated by a surgeon to perform the various resections, drill holes, etc. In certain embodiments, the device 60 may be an autonomous robot, as opposed to surgeon-assisted. That is, a tool path, as opposed to haptic boundaries, may be defined for resecting the bones and drilling holes since an autonomous robot may only operate along a pre-determined tool path such that there is no need for haptic feedback. In certain embodiments, the device 60 may be a cutting device with at least one degree of freedom that operates in conjunction with the navigation system 42. For example, a cutting tool may include a rotating burr with a tracker on the tool. The cutting tool may be freely manipulate-able and handheld by a surgeon. In such a case, the haptic feedback may be limited to the burr ceasing to rotate upon meeting the virtual boundary. As such, the device 60 is to be viewed broadly as encompassing any of the devices described in this application, as well as others.

After the surgical procedure is complete, a postoperative analysis (step 807) may be performed immediately or after a period of time. The postoperative analysis may determine the accuracy of the actual surgical procedure as compared with the planned procedure. That is, the actual implant placement position and orientation may be compared with the values as planned. Factors such as varus-valgus femoral-tibial alignment, extension, internal-external rotation, or any other factors associated with the surgical outcome of the implantation of the arthroplasty implants may be compared with the values as planned.

II. Preoperative Steps of Arthroplasty Procedure

The preoperative steps of an arthroplasty procedure may include the imaging of the patient and the preoperative planning process that may include implant placement, bone resection depth determination, and an anterior shaft notching assessment, among other assessments. The bone resection depth determination includes selecting and positioning three dimensional computer models of candidate femoral and tibial implants relative to three dimensional computer models of the patient's distal femur and proximal tibia to determine a position and orientation of the implants that will achieve a desirable surgical outcome for the arthroplasty procedure. As part of this assessment, the depths of the necessary tibial and femoral resections are calculated, along with the orientations of the planes of those resections.

The anterior shaft notching assessment includes determining whether or not an anterior flange portion of the three dimensional model of the selected femoral implant will intersect the anterior shaft of the three dimensional model of the patient's distal femur when the implant three dimensional model is positioned and oriented relative to the femur three dimensional model as proposed during the bone resection depth determination. Such an intersection of the two models is indicative of notching of the anterior femoral shaft, which must be avoided.

Determining bone resection depth and performing an anterior shaft notching assessment is described in PCT/US2016/034847, filed May 27, 2016, which is hereby incorporated by reference in its entirety.

A. Preoperative Imaging

Figure 4A:
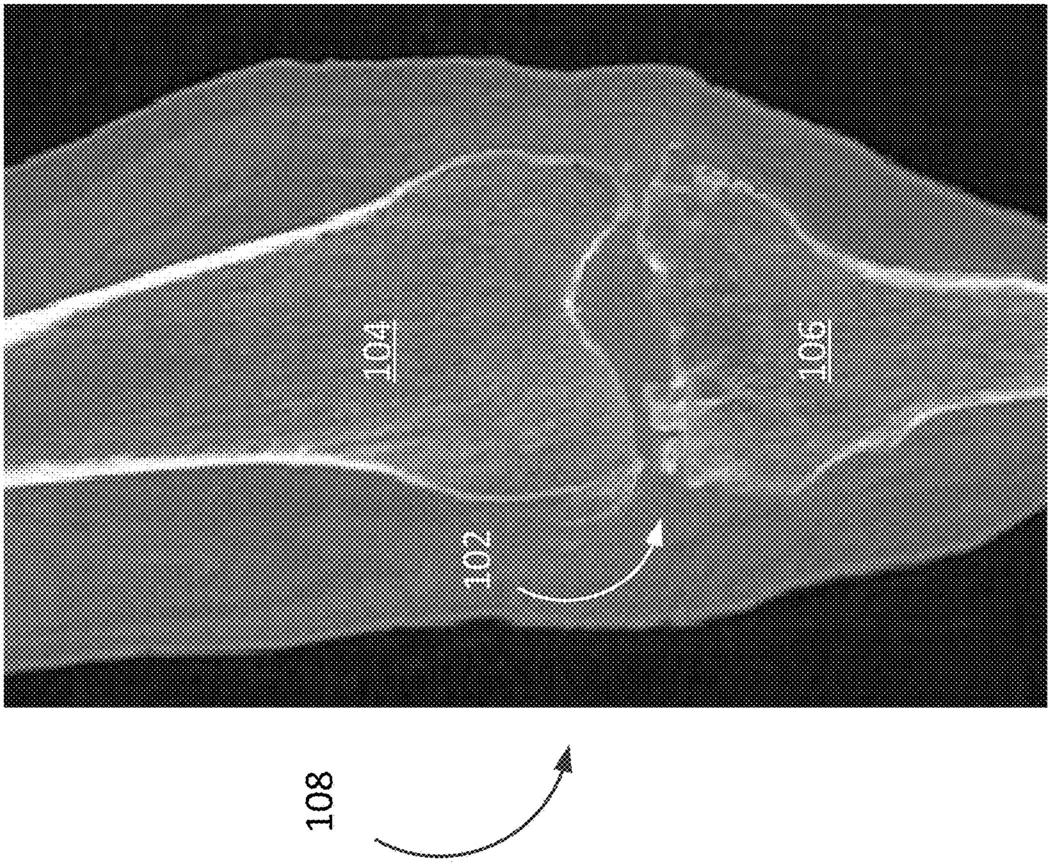
FIG. 4A is a coronal image slice of a knee joint in a degenerated state, prior to performance of the arthroplasty procedure.

In preparation for a surgical procedure (e.g., knee arthroplasty, hip arthroplasty, ankle arthroplasty, shoulder arthroplasty, elbow arthroplasty), a patient may undergo preoperative imaging at an imaging center, for example. The patient may undergo magnetic resonance imaging ("MRI"), a computed tomography ("CT") scan, a radiographic scan ("X-ray"), among other imaging modalities, of the operative joint. As seen in FIG. 4A, which is an example coronal scan of a knee, a patient joint 102 including a femur 104 and a tibia 106 may undergo a CT scan. The CT scan may include a helical scan of the knee joint 102 packaged as a Digital Imaging and Communications in Medicine ("DICOM") file. From the file, the volumetric image of the knee joint 102 is viewable in two-dimensional (2D) image slices or cross-sections (e.g., coronal, sagittal, axial) for case of viewing and planning. The image in FIG. 4A is one such example of a coronal view of the knee joint 102. The preoperative images then undergo a process known as segmentation. In one instance, the segmentation process may be performed on the two-dimensional images by applying a spline over the bone contour lines in each of the 2D images. Then, the splines can be combined to form a three-dimensional (3D) image of the bone. Alternatively, the 2D image slices may be assembled into a 3D volume image, if not already in 3D volumetric form. In this case, as will be discussed subsequently, the segmentation process may be performed on the images 108 as a whole without the need to apply a spline to the 2D image slices.

Figure 4B:
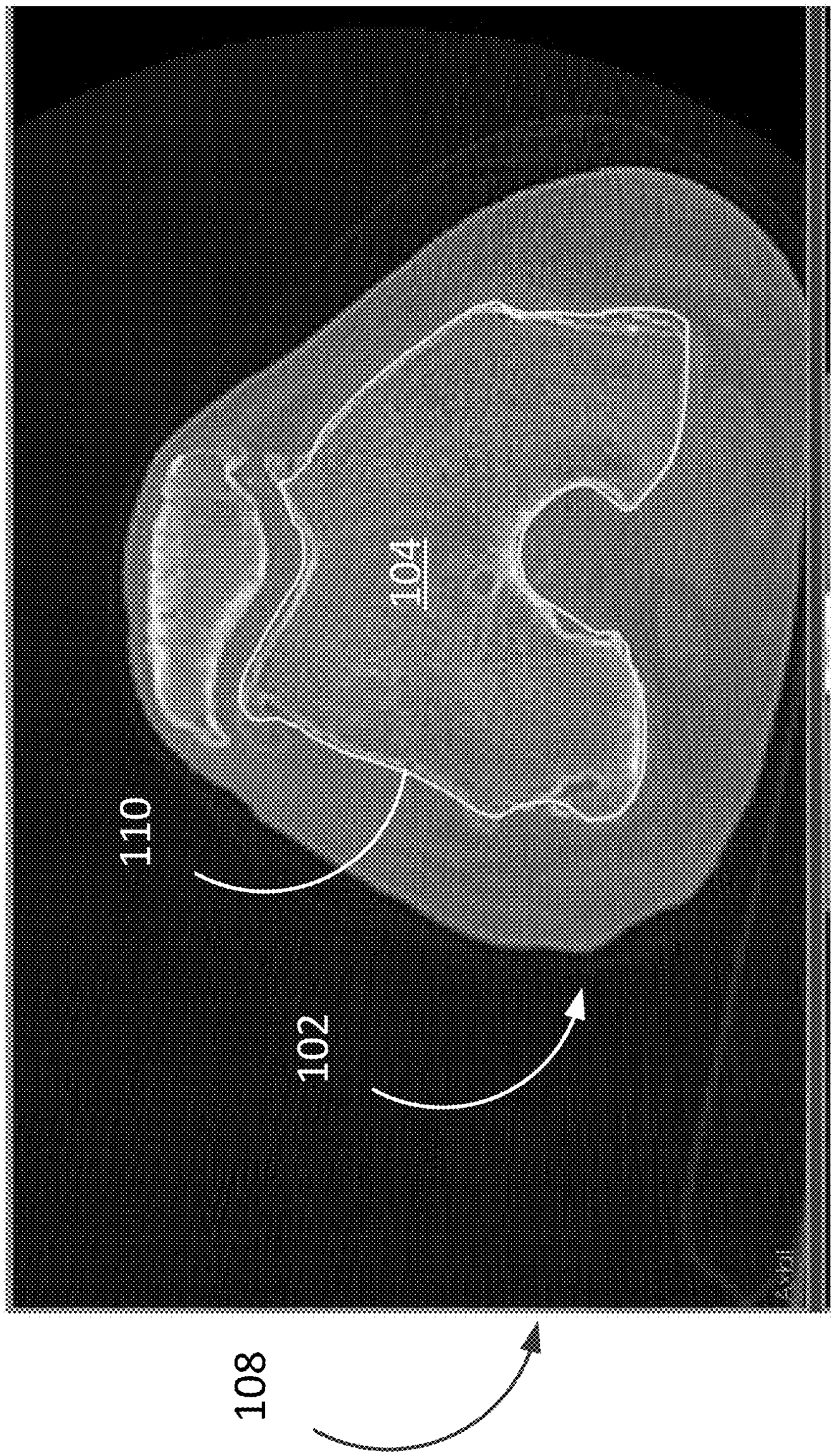
FIGS. 4B-4D are, respectively, axial, sagittal, and coronal images of the knee joint of FIG. 4A with a spline outlining the contours of the femur.
Figure 4C:
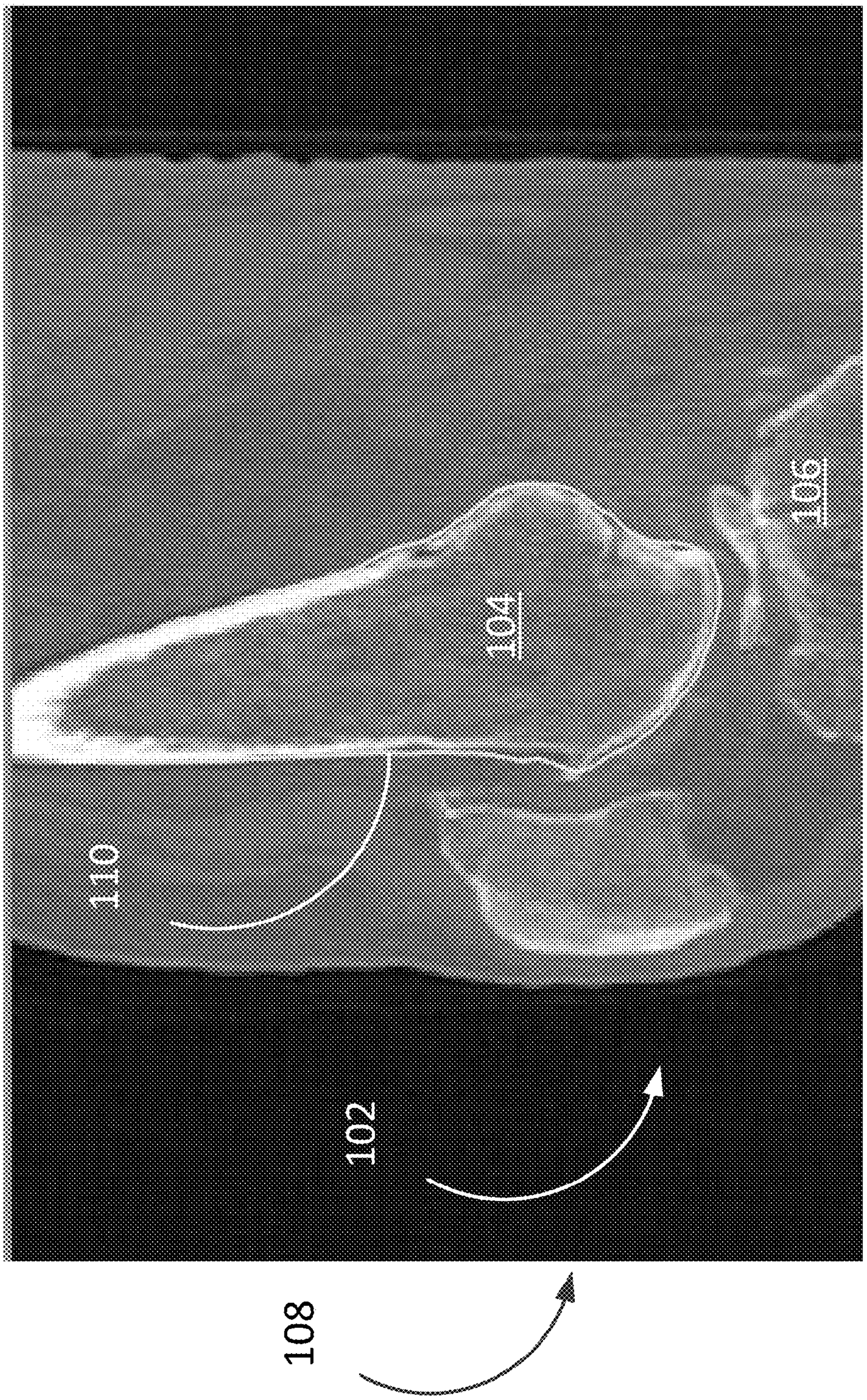
Figure 4D:
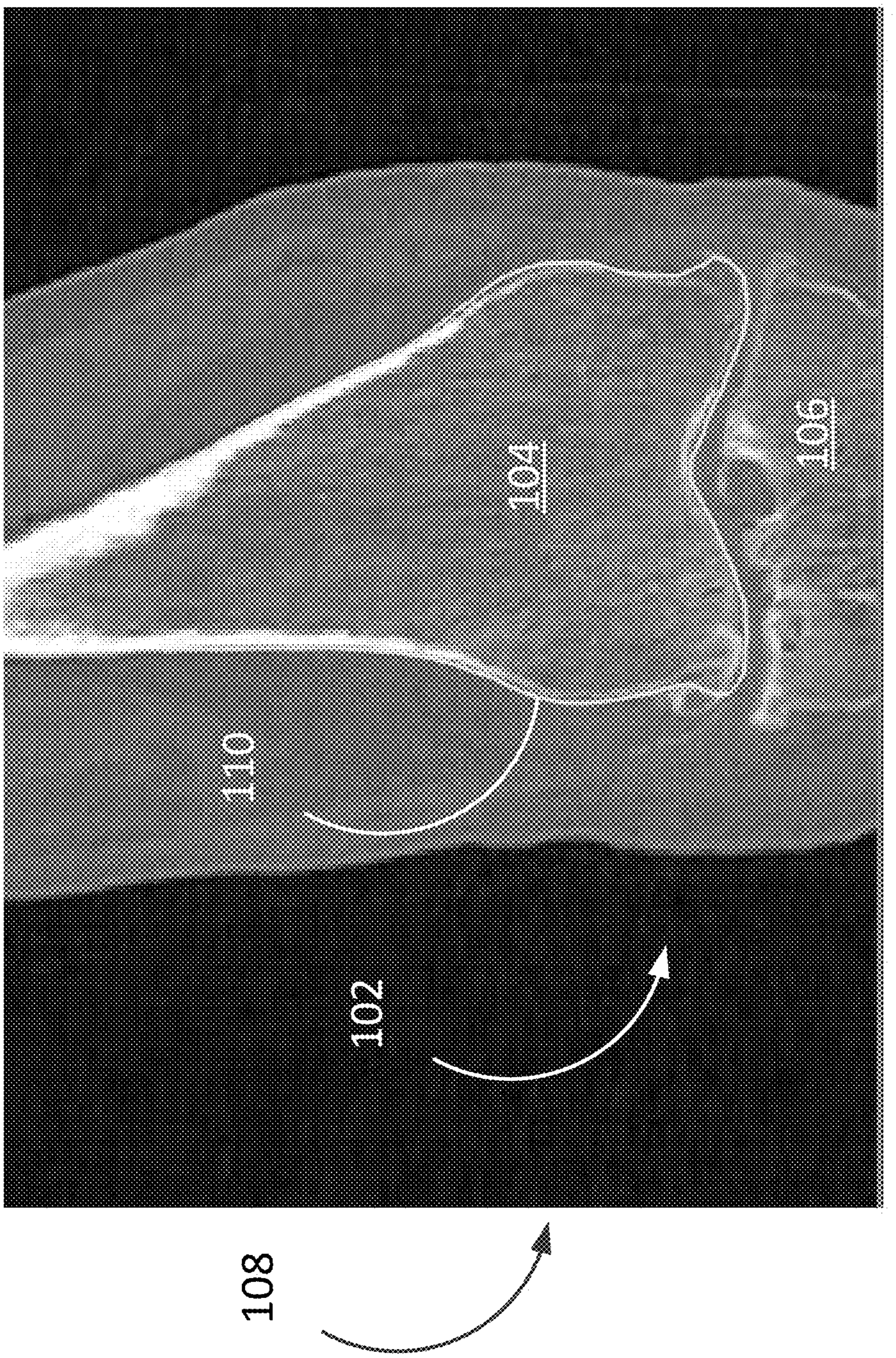

In one instance of a segmentation process, FIGS. 4B, 4C, and 4D illustrate, respectively, an axial image 108 of the femur 104 with a spline 110 on the bone surface of the femur 104, a sagittal image 108 of the joint 102 with a spline 110 on the bone surface of the femur 104, and a coronal image 108 of the joint 102 with a spline 110 on the femur 104. In certain instances, the segmentation process may be a manual process with a person identifying the position of the spline 110 on each two-dimensional image slice 108 to match the contour of the bone. In certain instances, the segmentation process may be automated where the spline 110 is automatically applied to the bone contour line in the image slices 108. And in certain instances, the segmentation process may be a combination of manual and automatic processes.

Figure 4E:
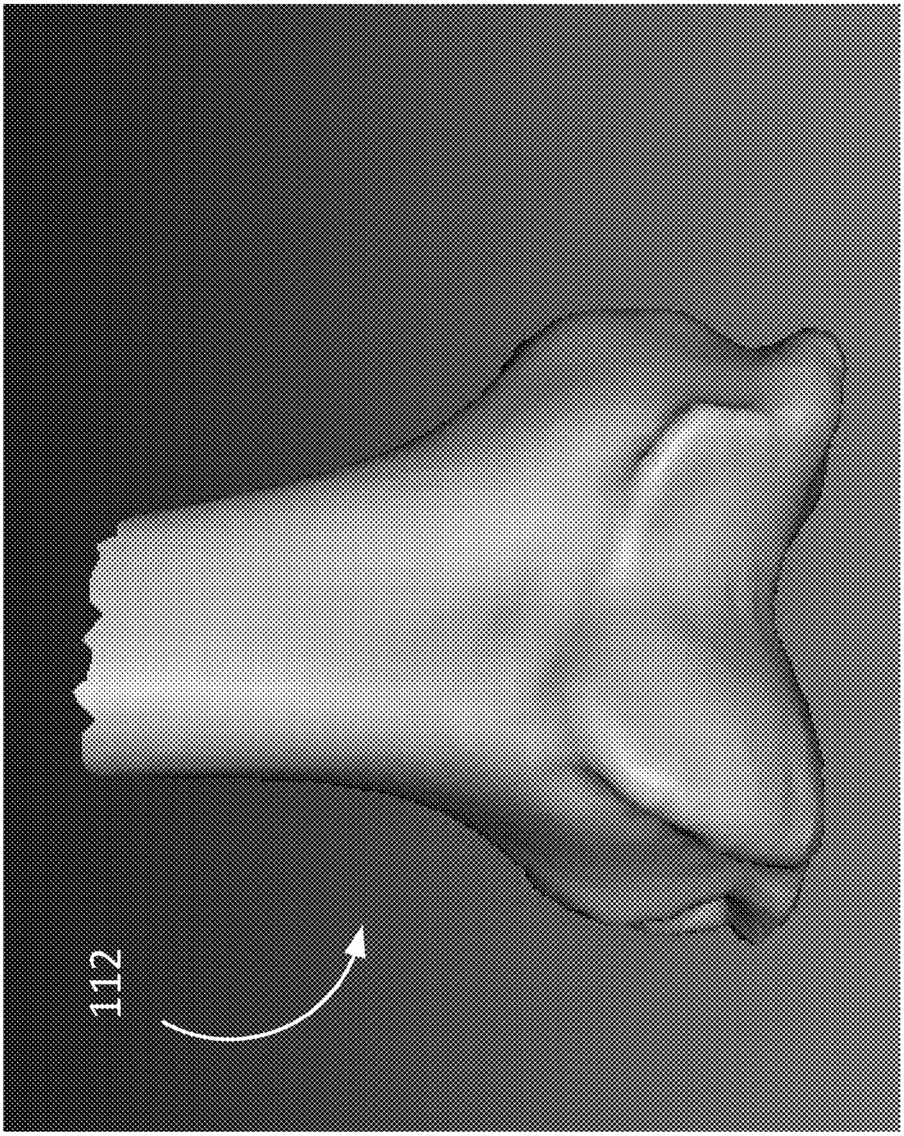
FIG. 4E is an anterior view of a preoperative three-dimensional femur bone model generated from the preoperative segmentation process.

After the application of the splines 110 is complete, the segmented images 108 may be combined in order to generate a 3D bone model of the joint 102, including a 3D femoral model 112, and a 3D tibial model (not shown in the figures). As seen in FIG. 4E, which is an anterior view of the 3D femoral model 112, the model 112 represents the femur 104 in a degenerated state, prior to performance of any surgical procedure to modify the bone. From this model 112, various steps of a preoperative planning process may be performed.

In another instances and as an alternative to generating the 3D bone model 112 from applying splines 110 to 2D images 102, 3D segmentation methods, both manual and automatic, can be applied to the CT image as a whole to obtain the 3D bone models 112 of FIG. 4E. For example, Active Appearance Models (AAM) may be used to segment a variety of anatomical structures including bone and cartilage in various 3D imaging modalities including CT and MRI. Thus, the 3D bone model 112 shown in FIG. 112 may be the result of an AAM segmentation process utilizing the initial volumetric scan data represented, partially, by the 2D image slice 108 in FIG. 4A.

AAM is a computer visual algorithm for matching statistical models of an object shape and appearance (e.g., bone) to a new image. The AAM is constructed from a training set of data and can be morphed or fitted to an image. Other technologies including Random Forests, Graph Cuts, and Deep Learning, may be utilized to generate bone models representative of the patient's anatomy. Background on Active Appearance Models can be found in the following articles, which are incorporated by reference in their entireties: T. F. Cootes, G. J. Edwards and C. J. Taylor. (2001). "Active Appearance Models", IEEE PAMI, Vol. 23, No. 6, pp. 681-685; and Williams, T. G., Vincent, G., Bowes, M., Cootes, T., Balamoody, S., Hutchinson, C., Taylor, C. J. (2010). "Automatic segmentation of bones and inter-image anatomical correspondence by volumetric statistical modelling of knee MRI." IEEE Int. Symp. Biomed. Imaging: Nano Macro, ISBI-Proc. (pp. 432-435).

Figure 4F:
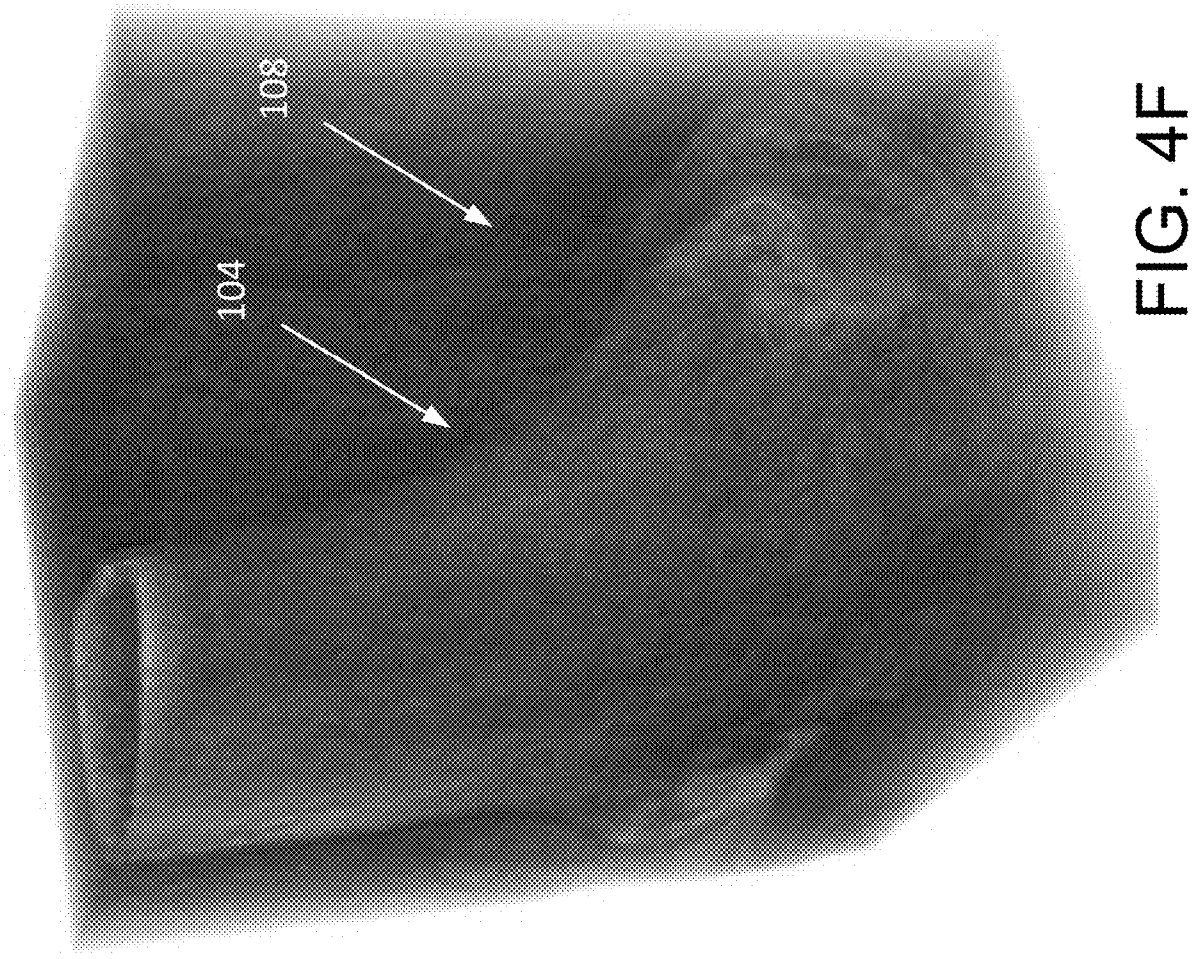
FIG. 4F is an isometric view of a three-dimensional CT image of a femur.
Figure 4G:
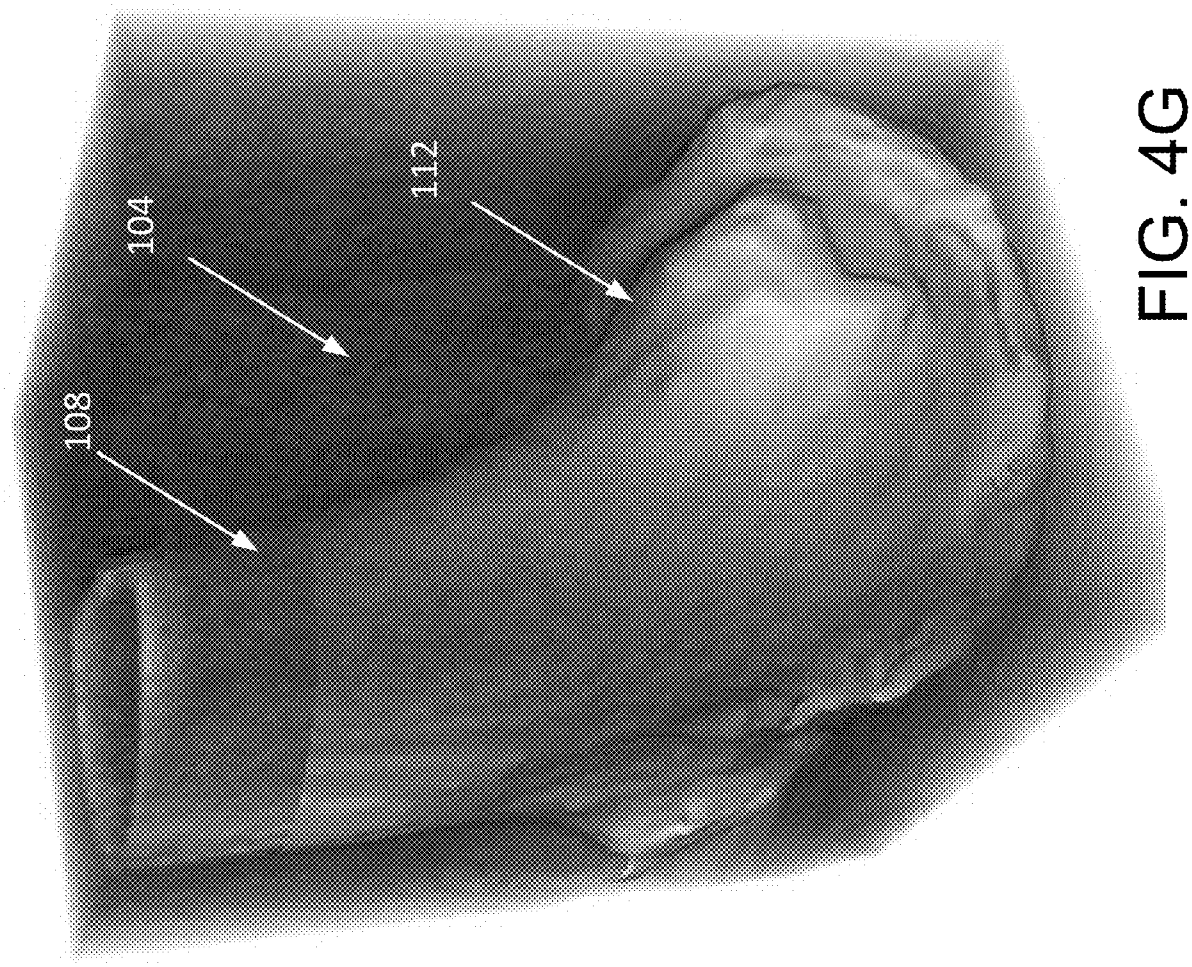
FIG. 4G is the isometric view of the three-dimensional CT image of the femur of FIG. 4F overlaid with a three-dimensional bone model of the femur resultant from appearance modeling of the three-dimensional CT image.

An example of generating a 3D bone model 112 from CT image data 108 via an active appearance model is illustrated in FIGS. 4F and 4G. FIG. 4F is an isometric view of a volumetric CT image 108 of a distal femur 104. As noted previously, CT images 108 are often viewed in two-dimensional reference frames (e.g., coronal, sagittal, axial) for convenience and for observation of certain anatomical details; however, the images 108 are often contained in volumetric form, such as shown in FIG. 4F. FIG. 4G is the same isometric view of the volumetric CT image 108 of the femur 104 from FIG. 4F, but with the 3D bone model 112 generated from a volumetric model, more specifically, an active appearance model algorithm, overlaid thereon. And while the 3D bone model 112 is shown in an isometric view in FIG. 4F, it can be appreciated that the entire distal end of the femur 104 has been modelled. That is, the 3D bone model 112 has been generated based on the three-dimensional nature of the entire distal end of the femur 104.

Figure 4H:
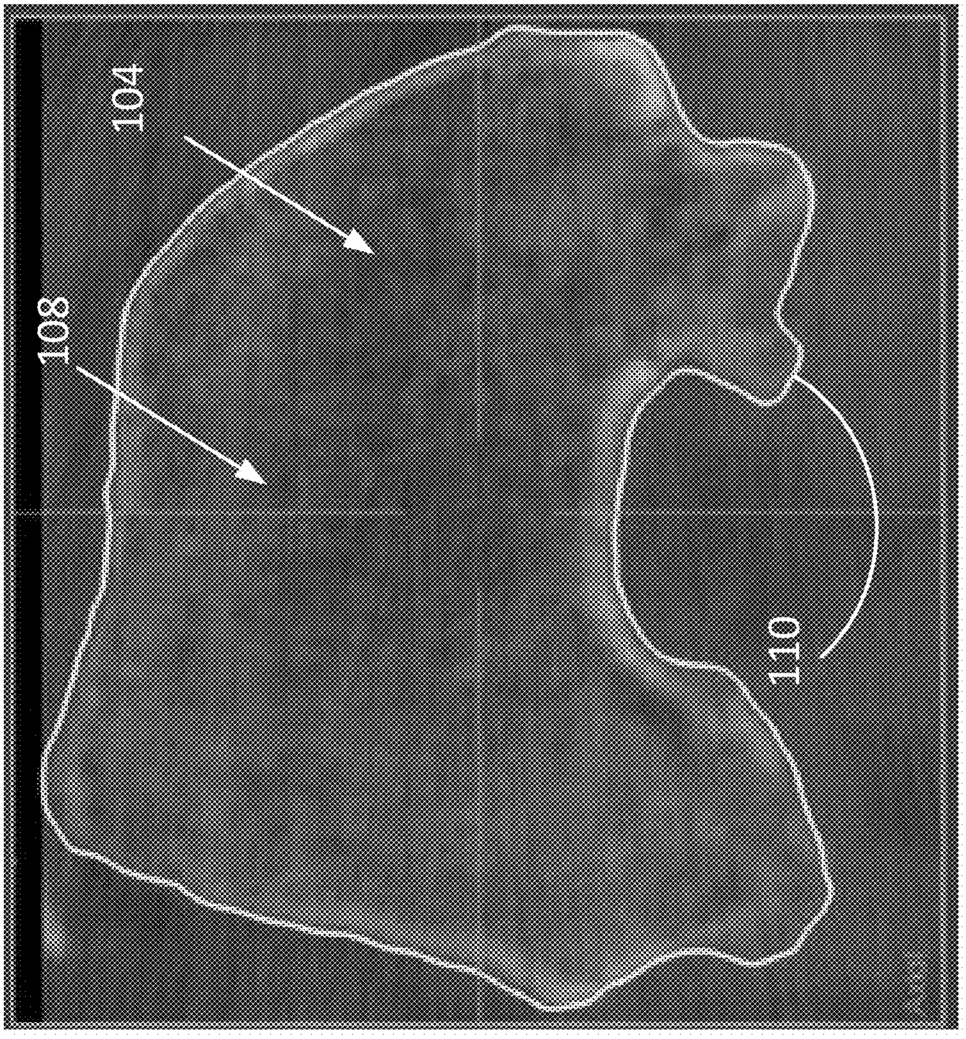
FIGS. 4H-4J are, respectively, axial, sagittal, and coronal images of a volumetric CT image of the femur overlaid with a segmented cross-section line of the 3D bone model.
Figure 4I:
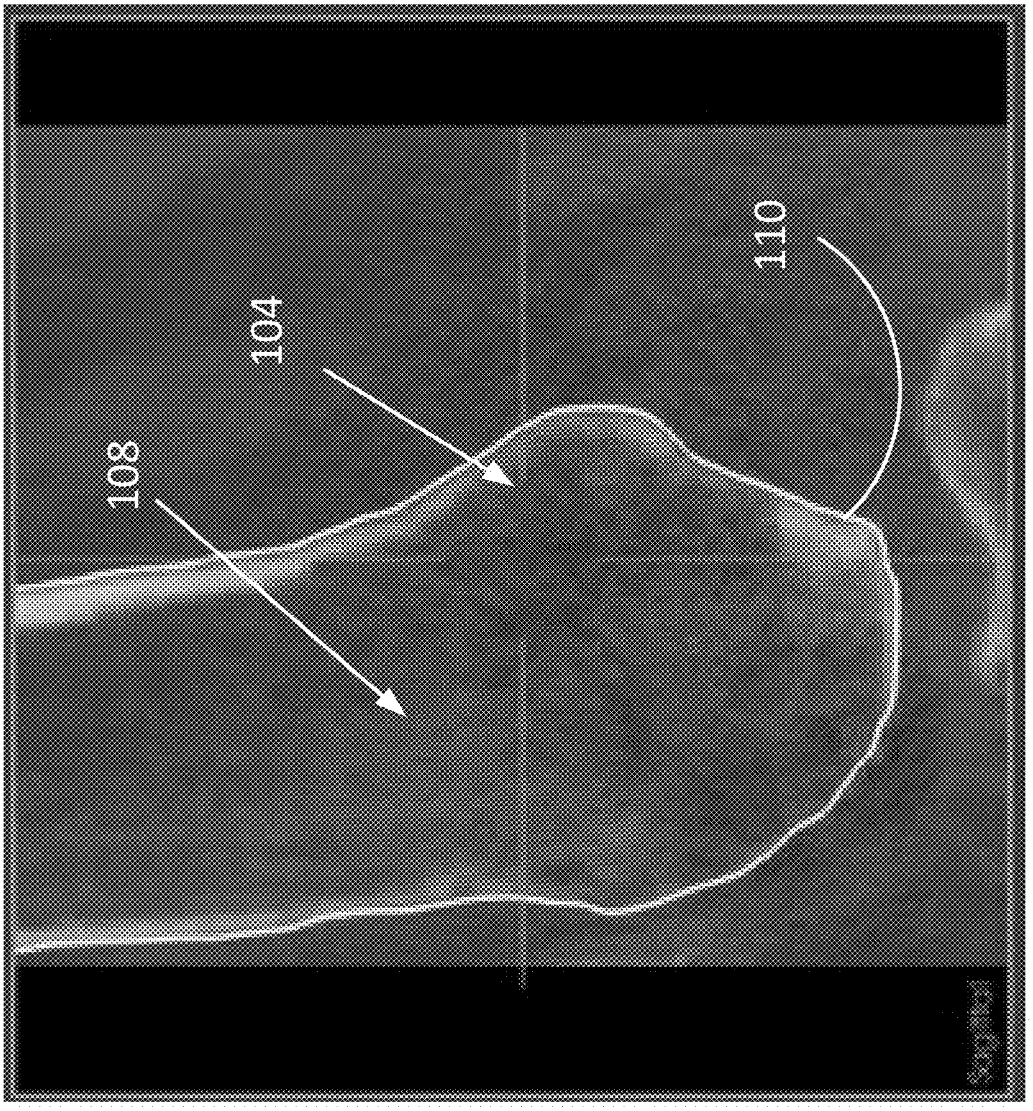
Figure 4J:
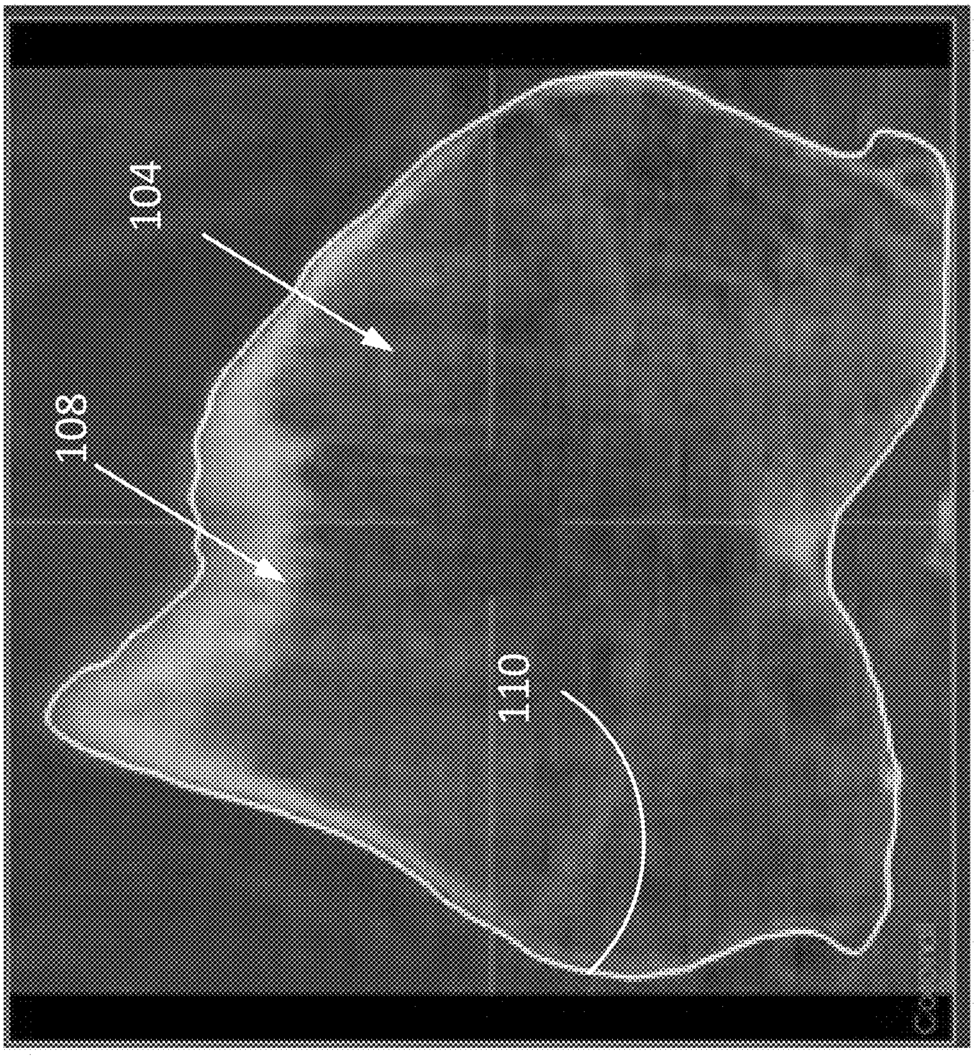

FIGS. 4H-4J respectively illustrate axial, sagittal, and coronal images of the volumetric CT image 108 of the femur 104 overlaid with a segmented cross-section line 110 of the 3D bone model 112 as taken at the particular reference frame (i.e., axial, sagittal, coronal). As noted, the segmented cross-section lines 110 are not splines that are applied in order to generate a 3D bone model. Instead, the 3D bone model 112 is generated using an Active Appearance Model, and the segmented cross-section line 110 is the perimeter of the model 112 overlaid on the CT image data 108. The two-dimensional images shown in FIGS. 4H-4J illustrate how closely the 3D bone model 112 formed via the AAM process matches the bone contours from the CT images.

Accordingly, the bone models 112 discussed herein may be the result of any number of bone model generation processes. In one embodiment, the bone model 112 is the result of applying splines to two-dimensional images of the bone, and combining the splines into a surface or volume model representing the bone. In one embodiment, the bone model 112 is the result of applying a mathematical model (e.g., active appearance modeling) to a volumetric image dataset. In one embodiment, the bone model 112 may be the product of morphing or modifying a generic bone model that is the result of an analysis of the medical images (e.g., CT, MRI, X-ray, etc.) of many (e.g., thousands or tens of thousands) of actual bones with respect to size and shape, and this analysis is used to generate the generic bone model, which is a statistical average of the many actual bones. In another embodiment, a statistical model is derived which describes the statistical distribution of the population, including the variation of size, shape and appearance in the image.

In certain instances, other methods of generating patient models may be employed. For example, patient bone models or portions thereof may be generated intra-operatively via registering a bone or cartilage surface in one or more areas of the bone. Such a process may generate one or more bone surface profiles. Thus, the various methods described herein are intended to encompass three dimensional bone models generated from segmented medical images (e.g., CT, MRI) as well as intra-operative imaging methods, and others.

While the imaging and subsequent steps of the method are described in reference to a knee joint 102, the teachings in the present disclosure are equally applicable to other anatomical regions such as the hip, ankle, shoulder, bone tumors, spinal column, CMF, wrist, and elbow, among others.

B. Preoperative Planning of Implant Selection, Positioning and Orientation of the Implant After the 3D bone model 112 of the patient joint 102 is generated, the remaining parts of the preoperative planning may commence. For instance, the surgeon or the system may select an appropriate implant, and the implant position and orientation may be determined. These selections may determine the appropriate drill holes, cuts, and/or resections to the patient bones in order to fit the chosen implant. Such preoperative planning steps may be found in PCT/US2016/034847, filed May 27, 2016, which is hereby incorporated by reference in its entirety.

III. Surgical Procedure

After the preoperative planning steps are completed, the surgery may commence according to the plan. That is, the surgeon may use the robotic device 60 of the surgical system 100 to perform resections of the patient's bone, and the surgeon may implant an implant to restore the function to the joint. And while the surgery is described as being performed via a robotic device 60, the postoperative analysis in the subsequent section is equally applicable to manually performed surgeries.

IV. Postoperative Analysis

After the surgical procedure is complete, a postoperative analysis may be performed to determine the accuracy of the surgical procedure as compared with the planned outcome.

Figure 5:
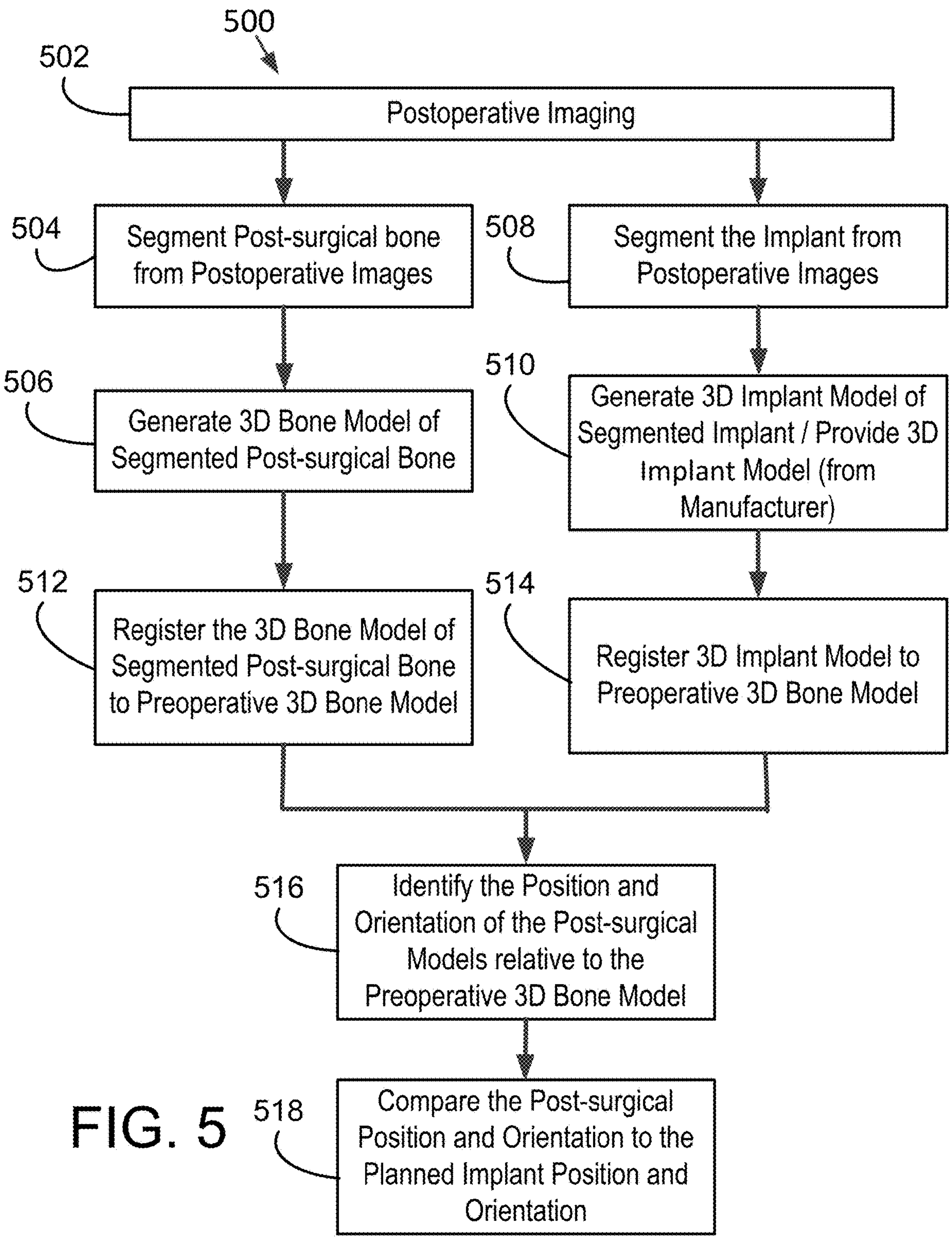
FIG. 5 is a flow chart illustrating postoperative analysis of the arthroplasty procedure.

To begin, reference is made to FIG. 5, which is a flowchart illustrating exemplary steps of the postoperative analysis method 500. At step 502 of the method 500, the patient may undergo postoperative imaging. The patient may, for example, undergo a CT scan, MRI scan, or X-ray, among other types of imaging scans of the operative area of the body.

In general, the postoperative imaging will show the prosthesis implanted on the patient bone. As with the preoperative image scan, the postoperative image scan may be in the form of a DICOM file where individual 2D image scans or slices can be viewed along various reference planes (e.g., coronal, sagittal, axial).

Conventionally, it may be difficult for a surgeon to ascertain the postoperative alignment of an implant relative to the bone in a postoperative CT scan, for example, because the metal artifacts associated with the metal implant tend to obscure the alignment of the implant relative to the bone. This leads to challenges of determining the actual implant placement relative to bone. Thus, the method 500 described herein describes a method of postoperative analysis of implant placement that obviates the issue with artifacts in CT scans. The method 500 also obviates the need for enhanced radiation thereby reducing metal artifacts. Additionally, it may also be difficult for a surgeon to ascertain the postoperative alignment of an implant relative to the bone in a postoperative CT scan because many of the anatomical landmarks used for planning the surgery are no longer present after surgery (i.e., the landmarks have been removed). The method of registration of post-operative bone to pre-operative bone described below helps to overcome these difficulties.

Figure 6A:
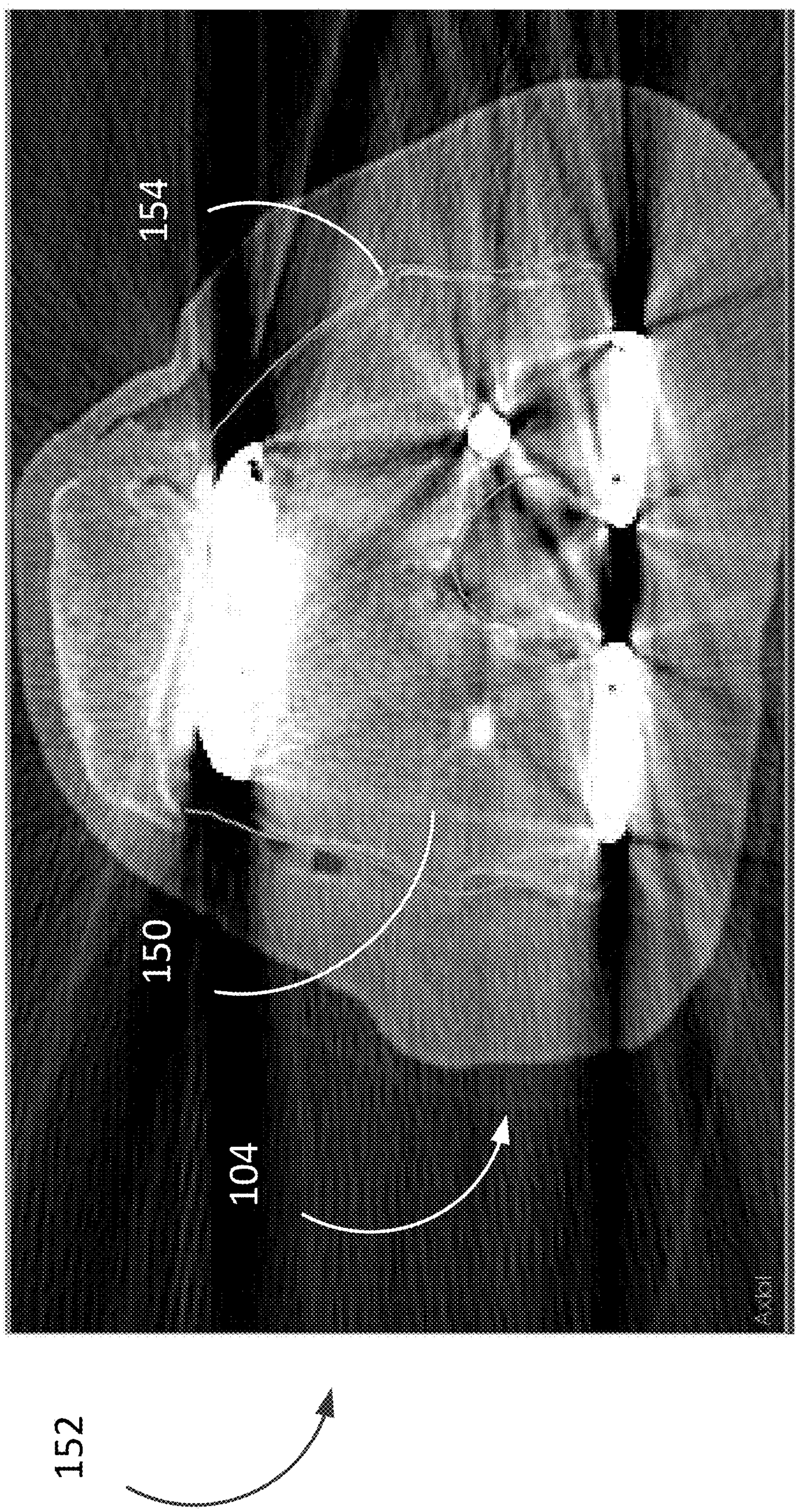
FIGS. 6A-6C are, respectively, axial, sagittal, and coronal images of the knee joint generated postoperatively with a segmented cross-section line of a postoperative three-dimensional bone-remainder model overlaid thereon.
Figure 6B:
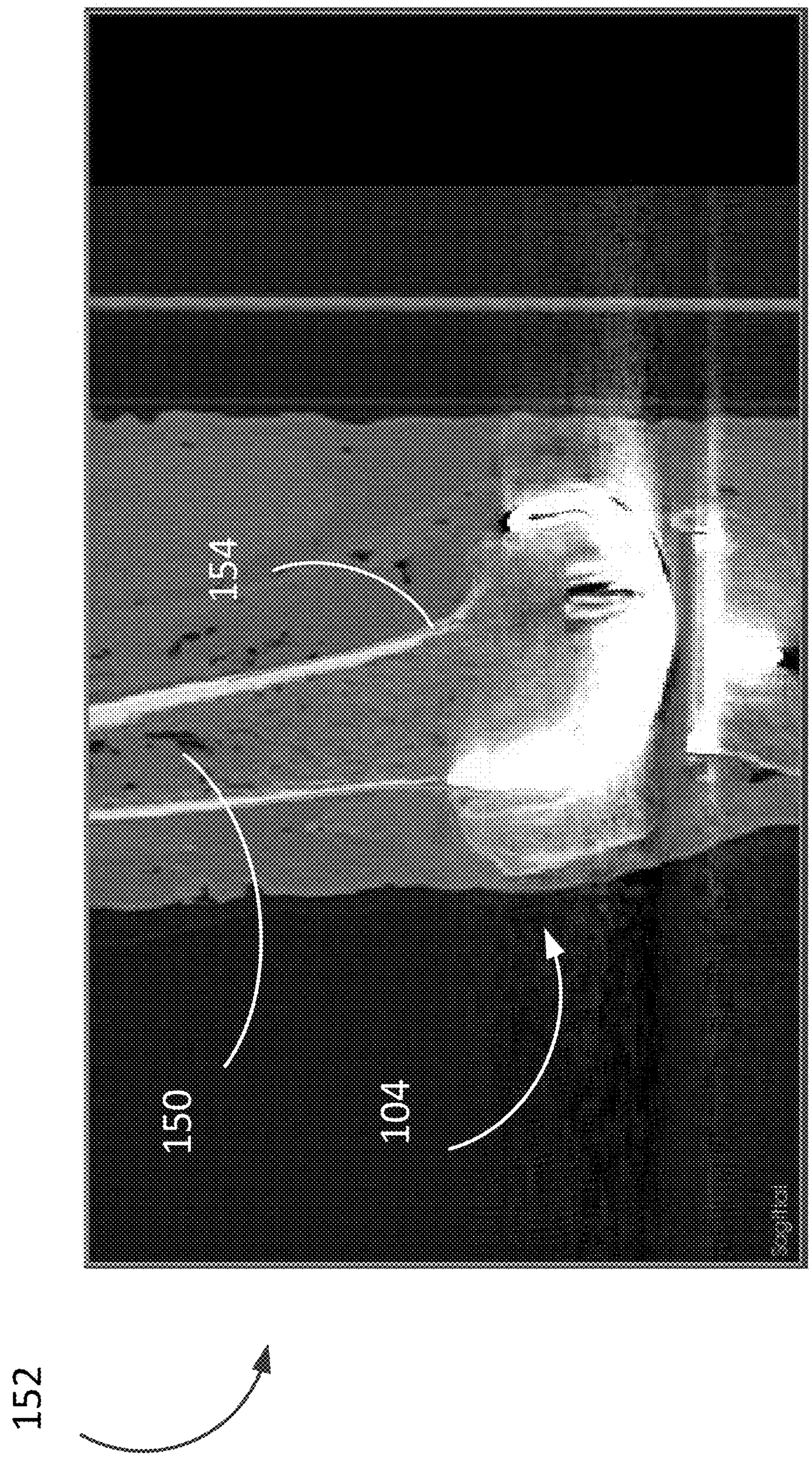
Figure 6C:
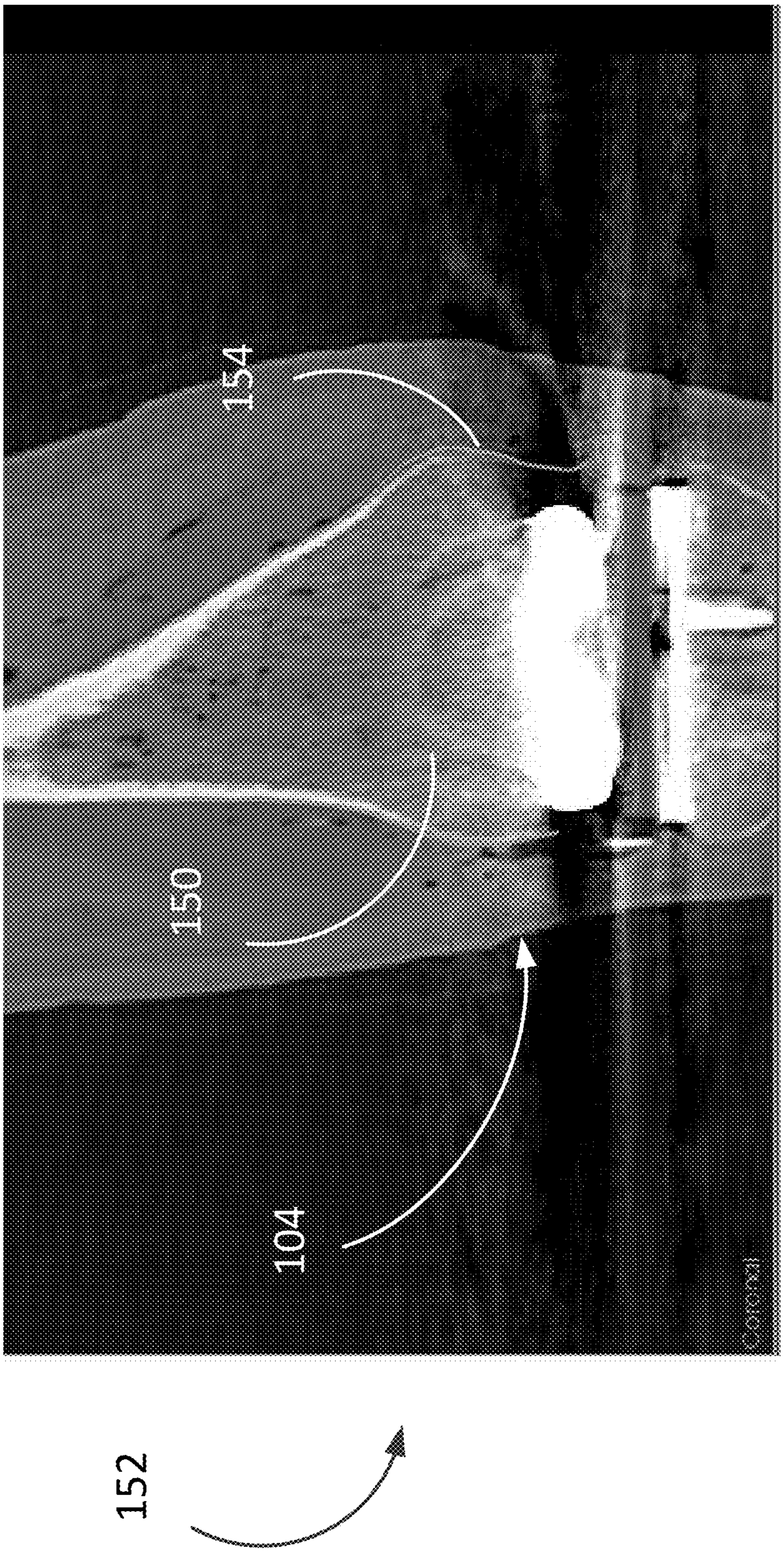

At step 504 of FIG. 5, and as seen in FIGS. 6A-6D, the post-surgical bone 150 may be segmented in the postoperative images 152 (also called post-surgical images). That is, the post-surgical bone 150 may be singled-out from the combined bone-implant from the post-surgical images. FIGS. 6A-6C illustrate, respectively, an axial view of the postoperative images 152 showing the bone 150 overlaid with a segmented cross-section line 154 of the 3D bone-remainder model 158 at a particular position in the axial plane, a sagittal view of the postoperative images 152 showing the bone 150 overlaid with a segmented cross-section line 154 of the 3D bone-remainder model 158 at a particular position in the sagittal plane, and a coronal view of the postoperative images 152 showing the bone 150 overlaid with a segmented cross-section line 154 of the 3D bone-remainder model 158 at a particular position in the coronal plane.

As seen in the figures, the bone and implant are shown in the postoperative images 152, but only the bone is segmented. Segmentation of the bone is seen by the segmented cross-section lines 154, which overlay portions of the bone, not the implant 156. In order to generate the segmented cross-section lines 154, the postoperative bone 150 may be segmented via an active appearance modeling algorithm that sizes a statistical or mathematical model to the post-operative image 152 of the bone in a 3D manner. The segmented cross-section lines 154 in FIGS. 6A-6C represent the results of the segmentation as applied to axial, sagittal, and coronal views of the postoperative images 152.

After segmenting the bone 150 in the postoperative images 152, the method 500 may include, at step 506 of FIG. 5, generating a 3D bone-remainder model 158 (also referred to as a 3D bone model) of the segmented post-surgical bone. The 3D bone-remainder model 158 of the segmented post-surgical bone can be seen in FIG. 6D, which also illustrates a void space 160 where the implant would be. In the context of segmentation with a 3D mathematical model (e.g., generic bone model, statistical bone model, AAM), the 3D mathematical bone model may be morphed or fitted to a shape of the 3D bone model 158 by fitting the surface of the 3D mathematical bone model to the surface of the images of the bone 150. In such an example, steps 504, 506 of segmentation and generation of the bone model may be considered a single step where the 3D bone-remainder model 158 is generated from an AAM process. In this case, the images in FIGS. 6A-6C show the relationship between the bone-remainder model 158 and the postoperative bone 150 in the postoperative images 152 in three two-dimensional reference frames (axial, sagittal, coronal) that were generated after generation of the bone-remainder model 158. And while step 504 describes "segmenting" the post-surgical bone, other methods may be employed that identify and extract the bone from the postoperative images 152.

Figure 7A:
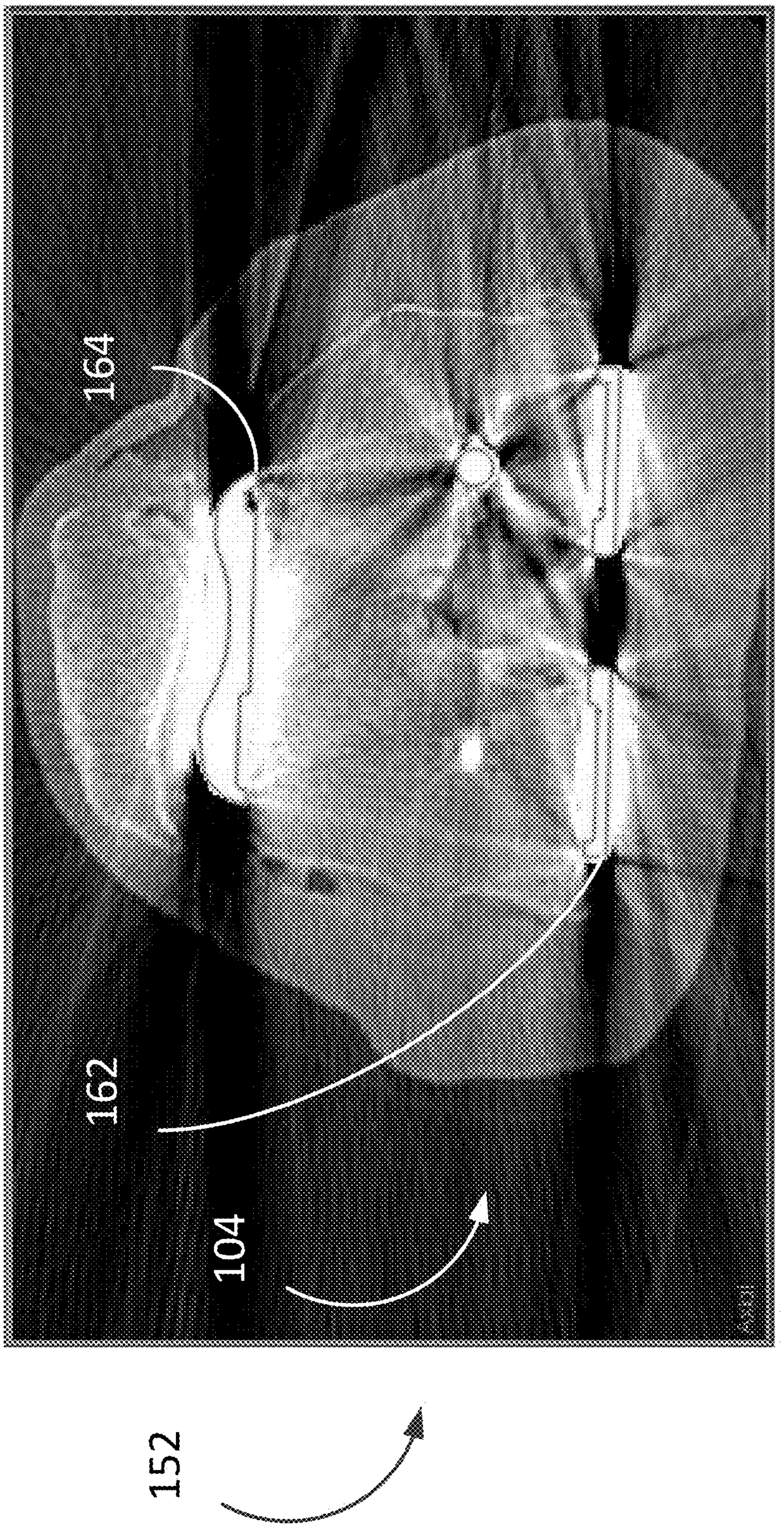
FIGS. 7A-7C are, respectively, axial, sagittal, and coronal images of the knee joint generated postoperatively with a segmented cross-section line of a three-dimensional implant model overlaid thereon.
Figure 7B:
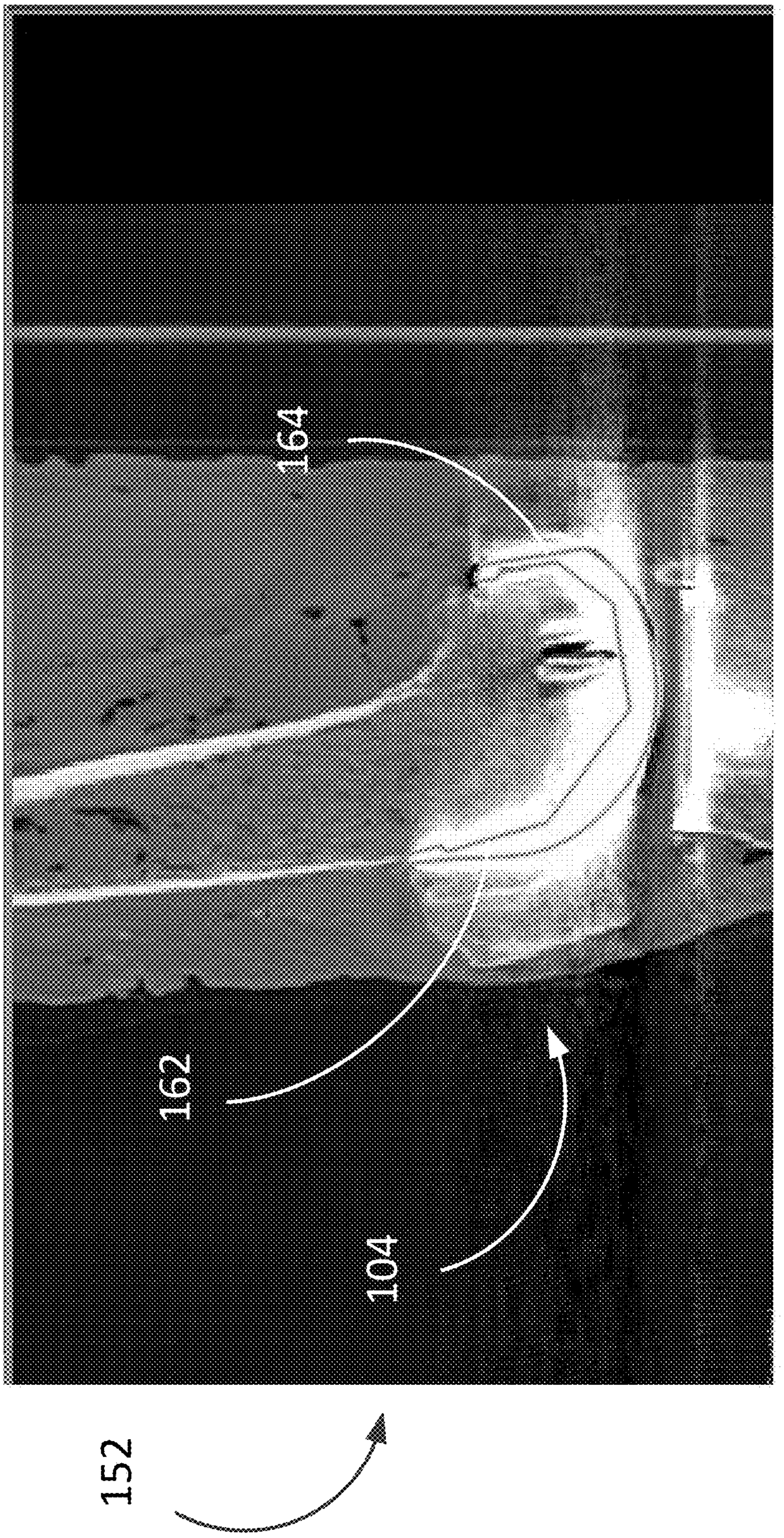
Figure 7C:
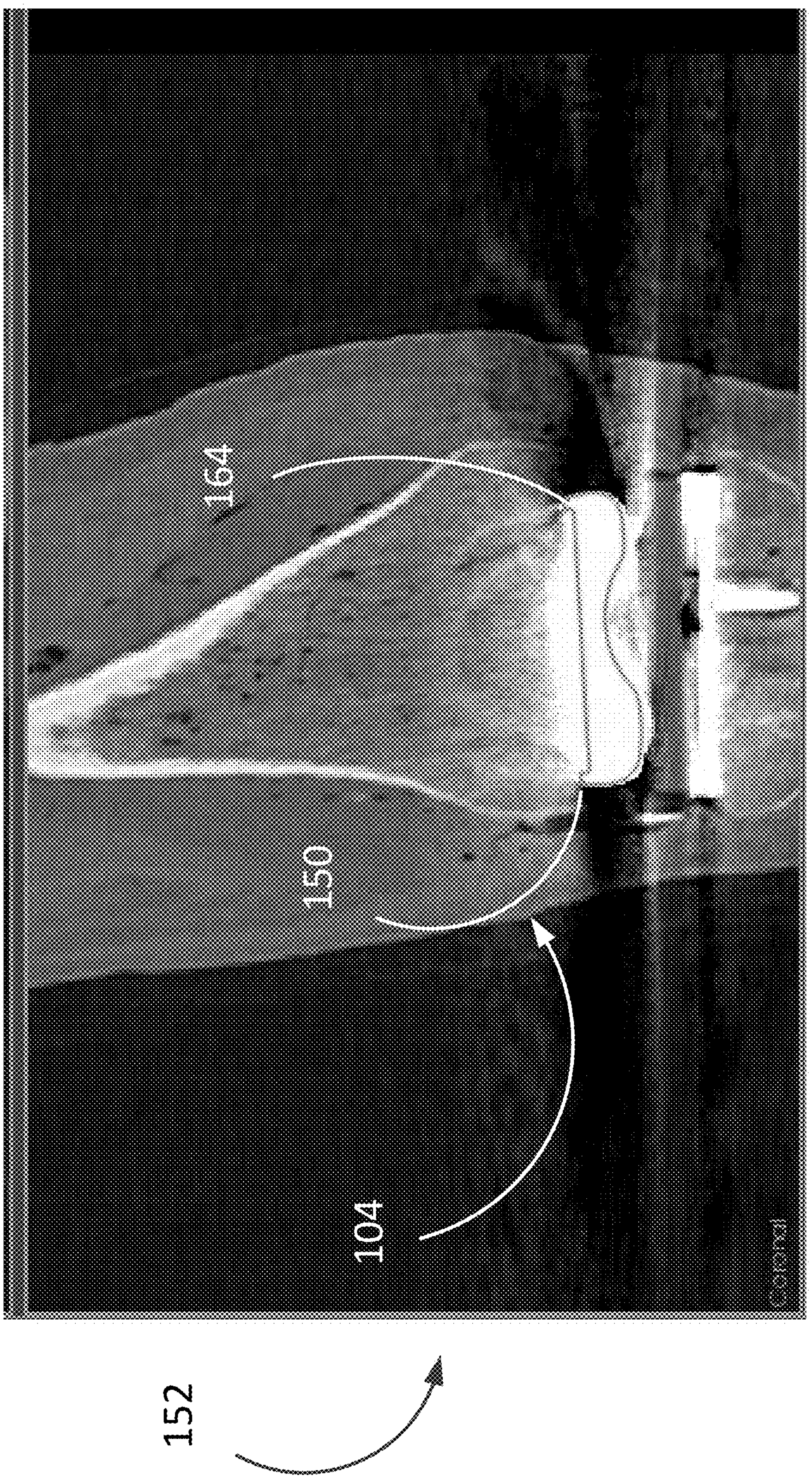
Figure 7D:
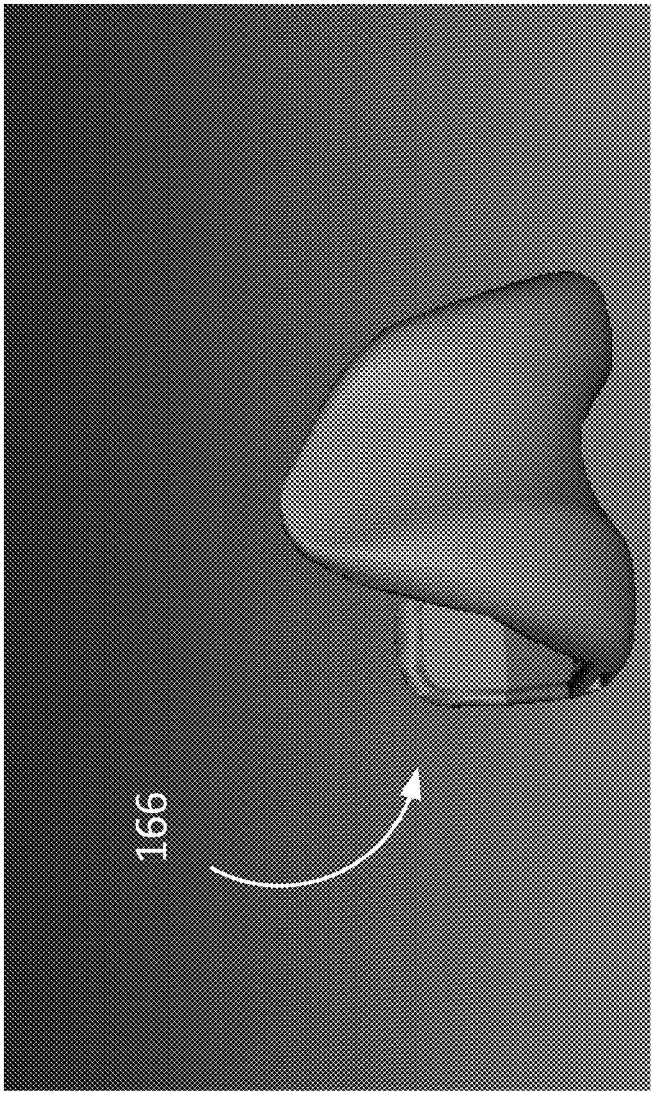
FIG. 7D is an anterior view of a three-dimensional implant model.

Turning back to FIG. 5, following the postoperative imaging step 502, the method 500 may include segmenting the implant 162 from the postoperative images 152, at step 508. FIGS. 7A-7C, illustrate, respectively, an axial view of the postoperative images 152 overlaid with a segmented cross-section line 164 of the 3D implant model 166 outlining the contour of the implant 162 at a particular position in the axial plane, a sagittal view of the postoperative images 152 overlaid with the segmented cross-section line 164 of the 3D implant model 166 outlining the contour of the implant 162 at a particular position in the sagittal plane, and a coronal view of the postoperative images 152 overlaid with the segmented cross-section line 164 of the 3D implant model 166 outlining the contour of the implant 162 at a particular position in the coronal plane. FIG. 7D illustrates the implant model 166 from which the segmented cross-section lines 164 (of FIGS. 7A-7C) were derived.

In step 508 and in FIGS. 7A-7C, the bone and the implant are shown in the images 152, but only the implant 162 is segmented. That is, the contours of the implant 162 are identified and represented by the segmented cross-section lines 164, which is overlaid on the postoperative images 152. As described with reference to step 504, segmentation of the implant may be performed via a 3D mathematical model that is morphed or fitted to the image of the implant in the postoperative images. The method 500 may also include, at step 510 of FIG. 5, generating a 3D implant model 166. In the example of using a 3D volumetric model that is modified to fit the image of the implant in the postoperative images 152, the steps 508, 510 of segmenting the implant and generating a 3D implant model 166 may be considered a single step where the 3D implant model 166 is generated from an AAM process. In this case, the images in FIGS. 7A-7C show the relationship between the implant model 166 and the postoperative bone in the postoperative images 152 in three two-dimensional reference frames (axial, sagittal, coronal) that were generated after generation of the implant model 166 of FIG. 7D.

As an alternative to generating an implant model 166 from the postoperative images 152, a 3D implant model 166 may be provided from the manufacturer and used to build a 3D segmentation model with the same technologies used for segmenting bone (e.g. AAM, Random Forests, Graph Cuts, Deep Learning). This is described in more detail in the subsequent sections of this application. From steps 504 and 508 of FIG. 5, the position and orientation of the implant 162, as implanted, is known relative to the bone remainder 104. As described with reference to the preoperative imaging, the step 510 of generating a 3D implant model 166 may involve a generic or statistical implant model that is modified or best fit to the image. And while step 508 describes "segmenting" the implant, other methods may be employed that identify and extract the implant from the postoperative images 152.

Figure 8A:
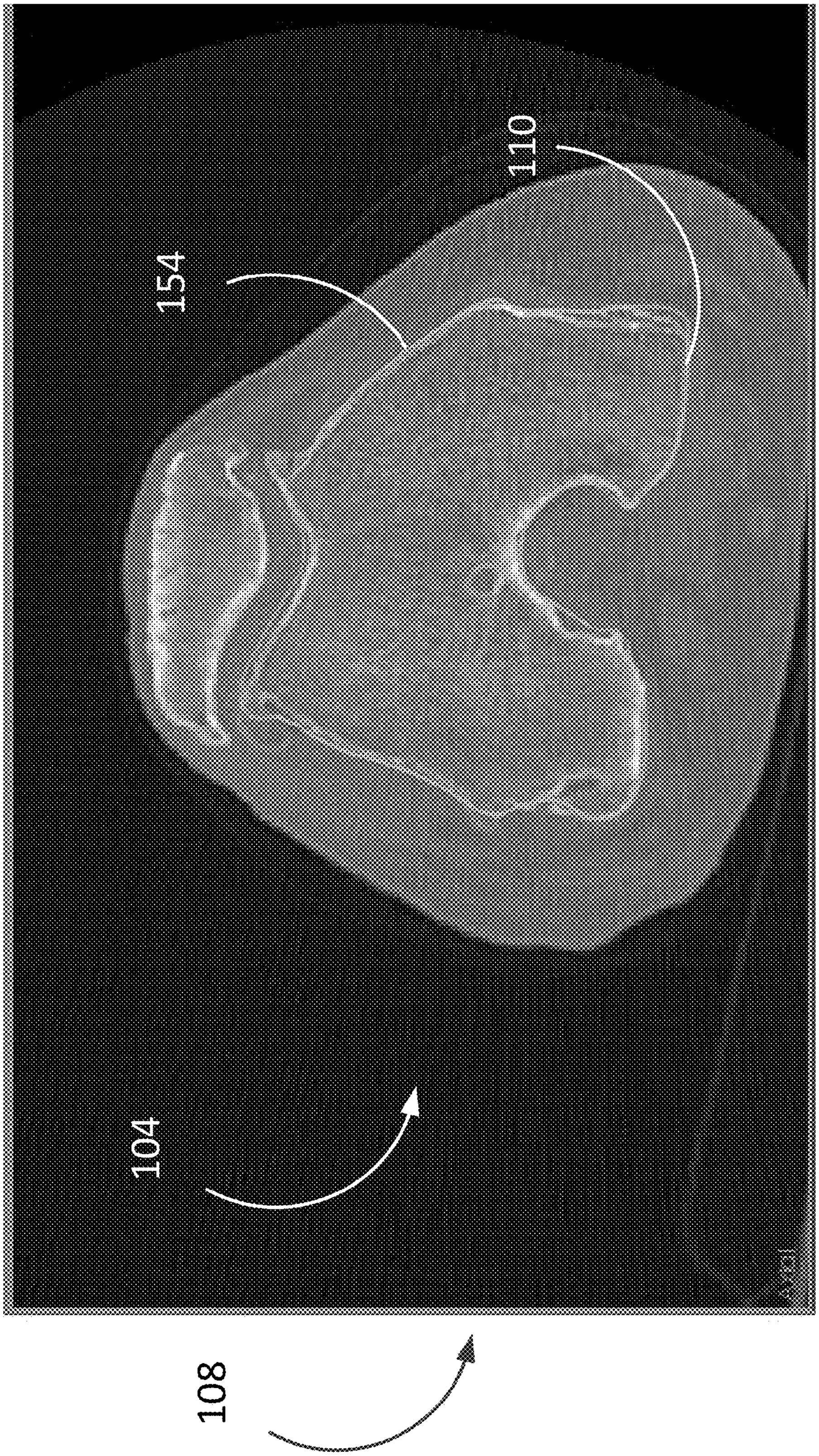
FIGS. 8A-8C are, respectively, axial, sagittal, and coronal images of a preoperative knee joint overlaid with segmented cross-section lines from the preoperative three-dimensional bone model and the postoperative three-dimensional bone-remainder model, respectively.
Figure 8B:
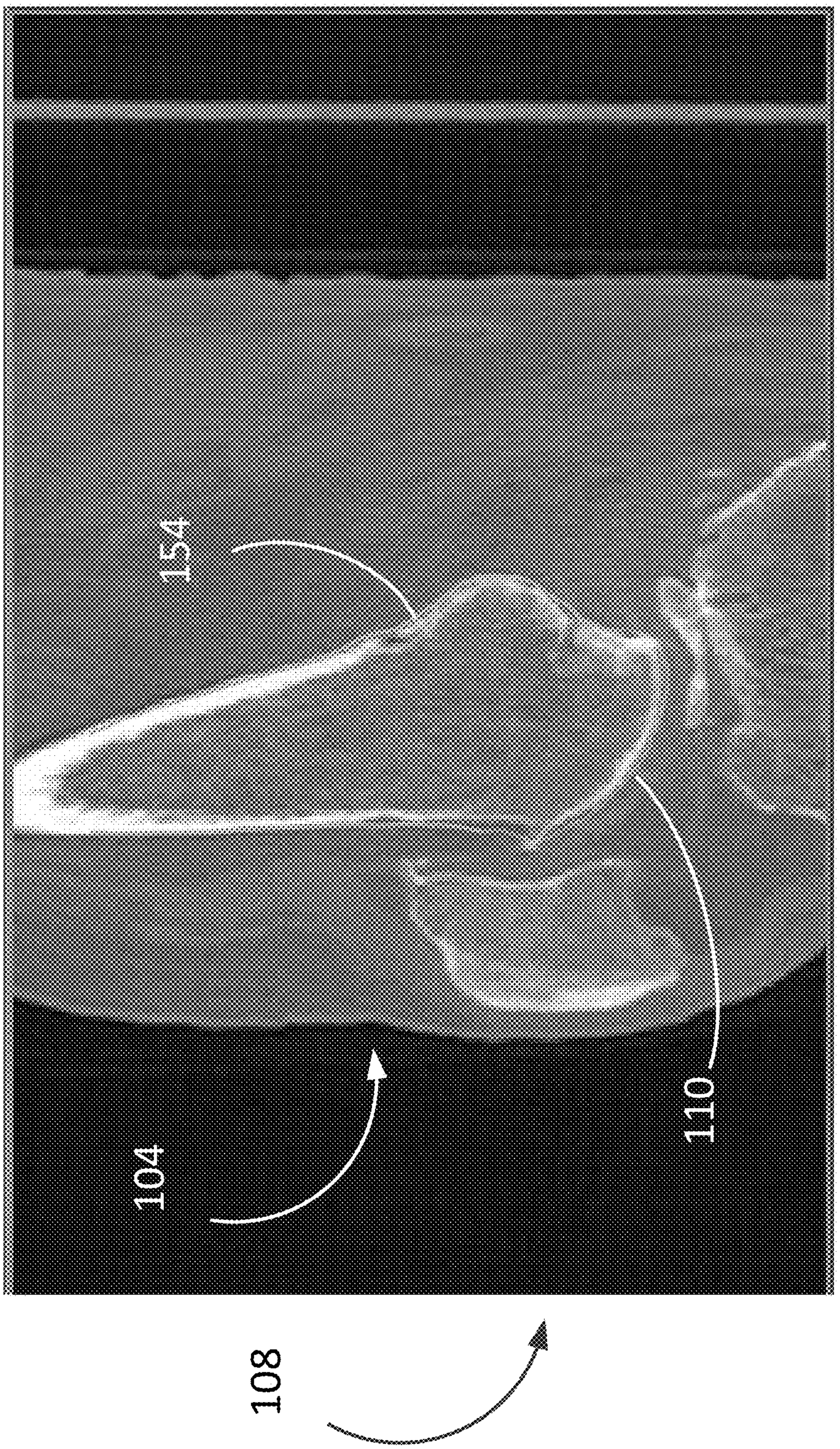
Figure 8C:
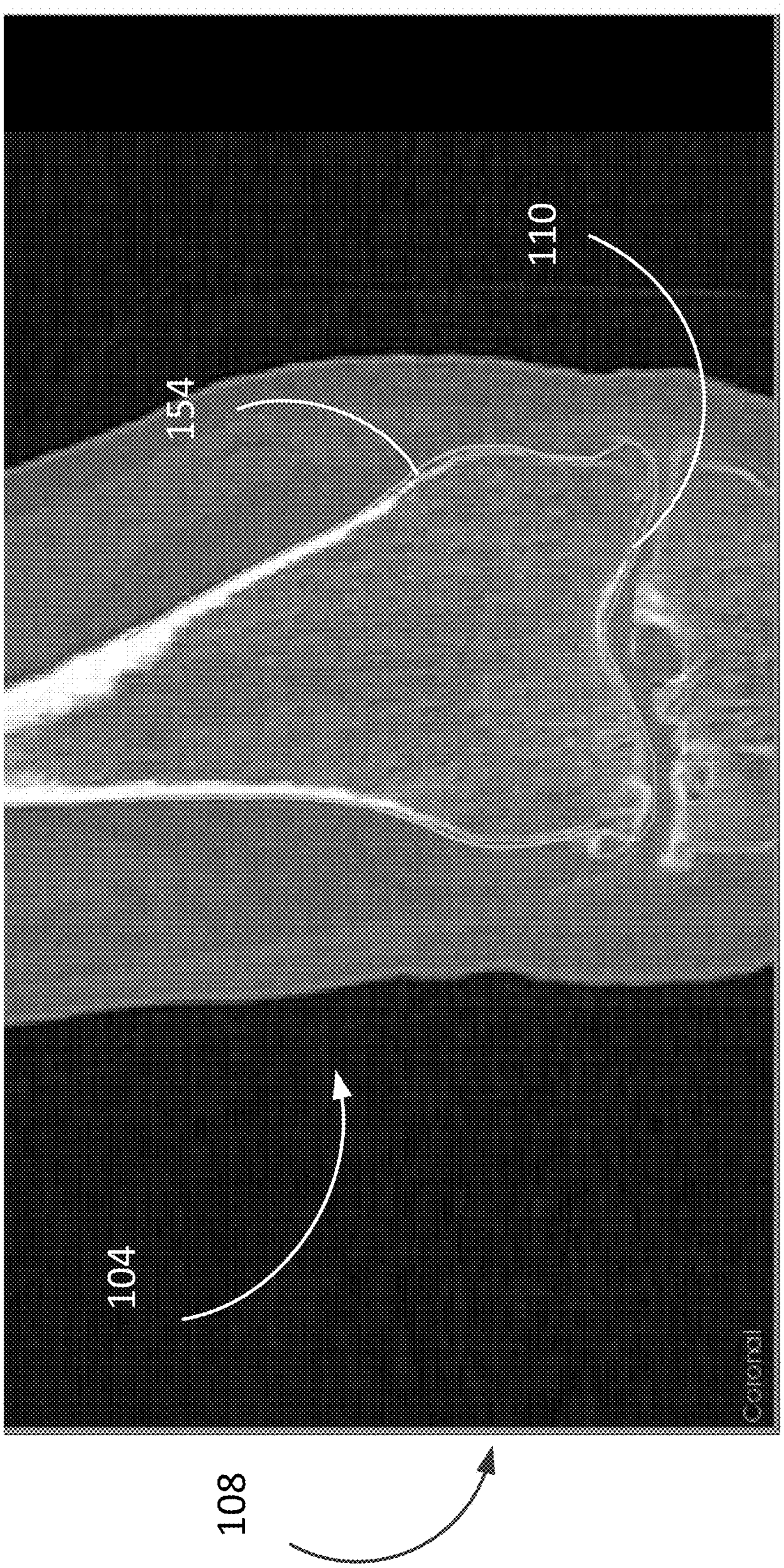
Figure 8D:
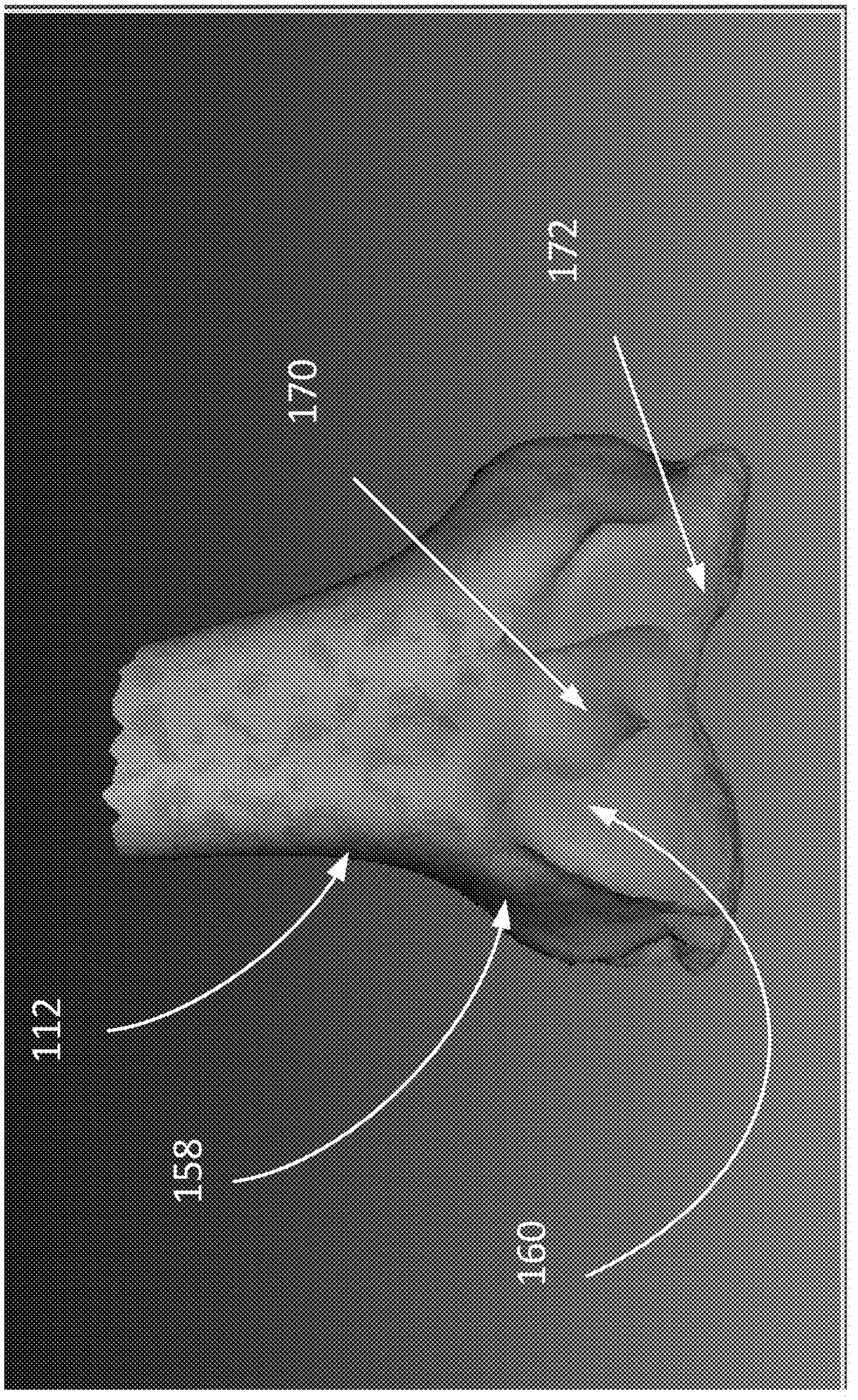
FIG. 8D is an anterior view of the postoperative three-dimensional bone-remainder model registered to the preoperative three-dimensional bone model.

Turning to FIG. 5, the method 500 may include registering the 3D bone-remainder model 158 generated from the post-surgical bone to the preoperative bone model 112, at step 512. And, the method 500 may include registering the 3D implant model 166 to the preoperative bone model 112 according to its position and orientation relative to the bone-remainder, at step 514. FIGS. 8A-8C illustrate, respectively, axial, sagittal, and coronal views of the preoperative femur 104 in the preoperative images 108 overlaid with segmented cross-section lines 110, 154 of the preoperative 3D bone model 112 and the postoperative 3D bone-remainder model 158, respectively. As seen in FIGS. 8A-8C, the segmented cross-section line 110 of the preoperative 3D bone model 112 fully bounds the distal femur 104, whereas the segmented cross-section line 154 of the postoperative 3D bone-remainder model 158 does not extend across the anterior (underneath the patella), distal, and posterior portions of the femur 104 as those portions were removed during the surgery. FIG. 8D illustrates the postoperative 3D bone-remainder model 158 registered to the preoperative 3D bone model 112. It can be seen that the models 158, 112 are near seamlessly overlaid with each other, except for the trochlear groove 170 and femoral condyles 172 of the preoperative 3D bone model 112, which are visible through the void 160 left in the postoperative 3D bone model 158. It is noted that the overlaid segmented cross-section lines 110, 154 of the preoperative 3D bone model 112 and the postoperative 3D bone-remainder model 158 in FIGS. 8A-8C are the result of the registration of the bone models 112, 158 shown in FIG. 8D. The images in FIGS. 8A-8C are intended to show the relationship between the bone models 112, 158 at exemplary reference frames (axial, sagittal, coronal).

From the positional relationship of the models 112, 158 in FIG. 8D, the portions of the bone that were removed during surgery can be determined. This information can be compared with the planned bone removal. In a certain instance, the preoperative plan may be registered to the combined models 112, 158 as well to determine how accurately the actual surgery comported with the planned surgery. In certain instances, the preoperative plan may be part of the preoperative bone model 112.

Figure 9A:
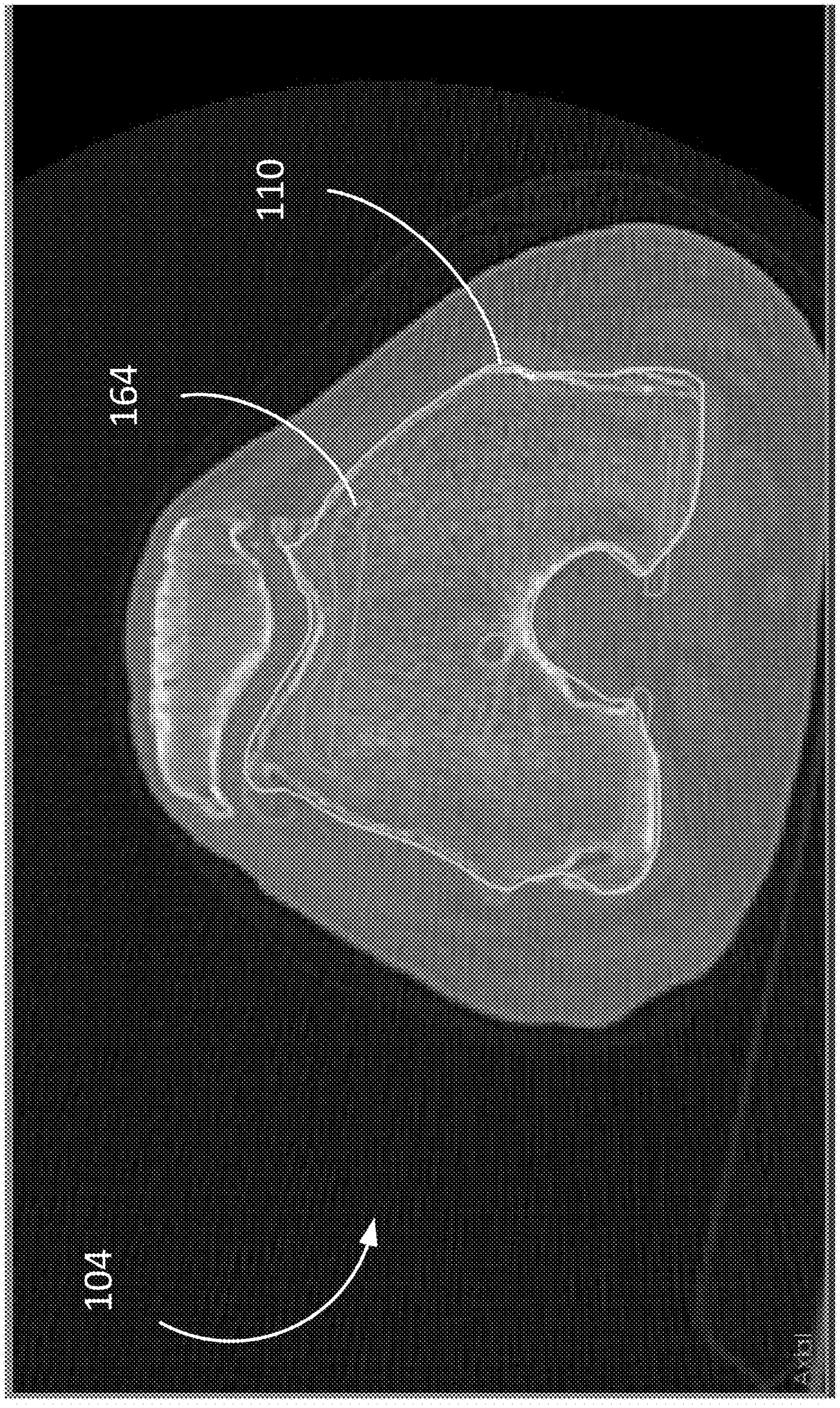
FIGS. 9A-9C are, respectively, axial, sagittal, and coronal images of a knee joint overlaid with segmented cross-sectional lines from the preoperative three-dimensional bone model and the three-dimensional implant model.
Figure 9B:
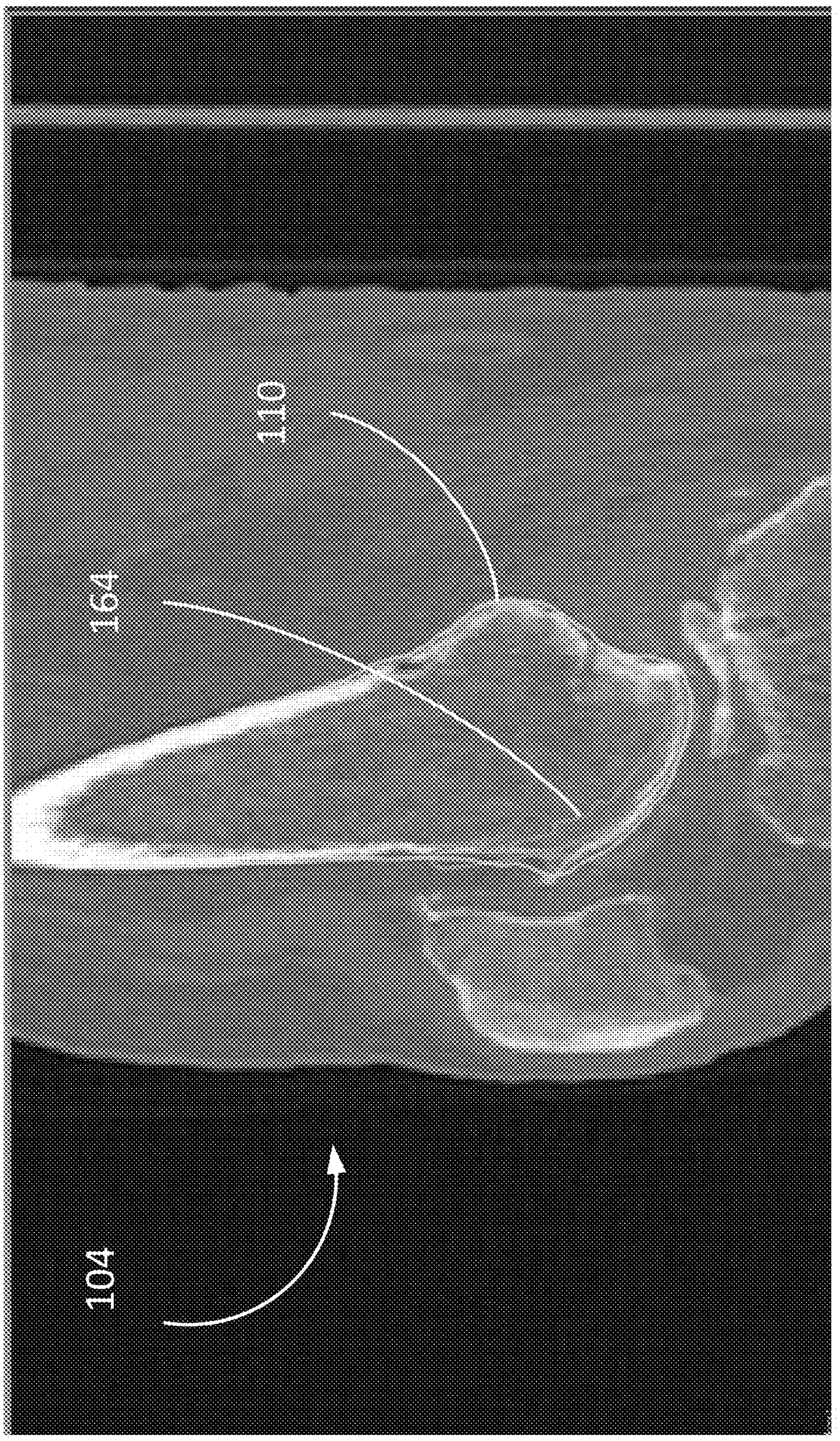
Figure 9C:
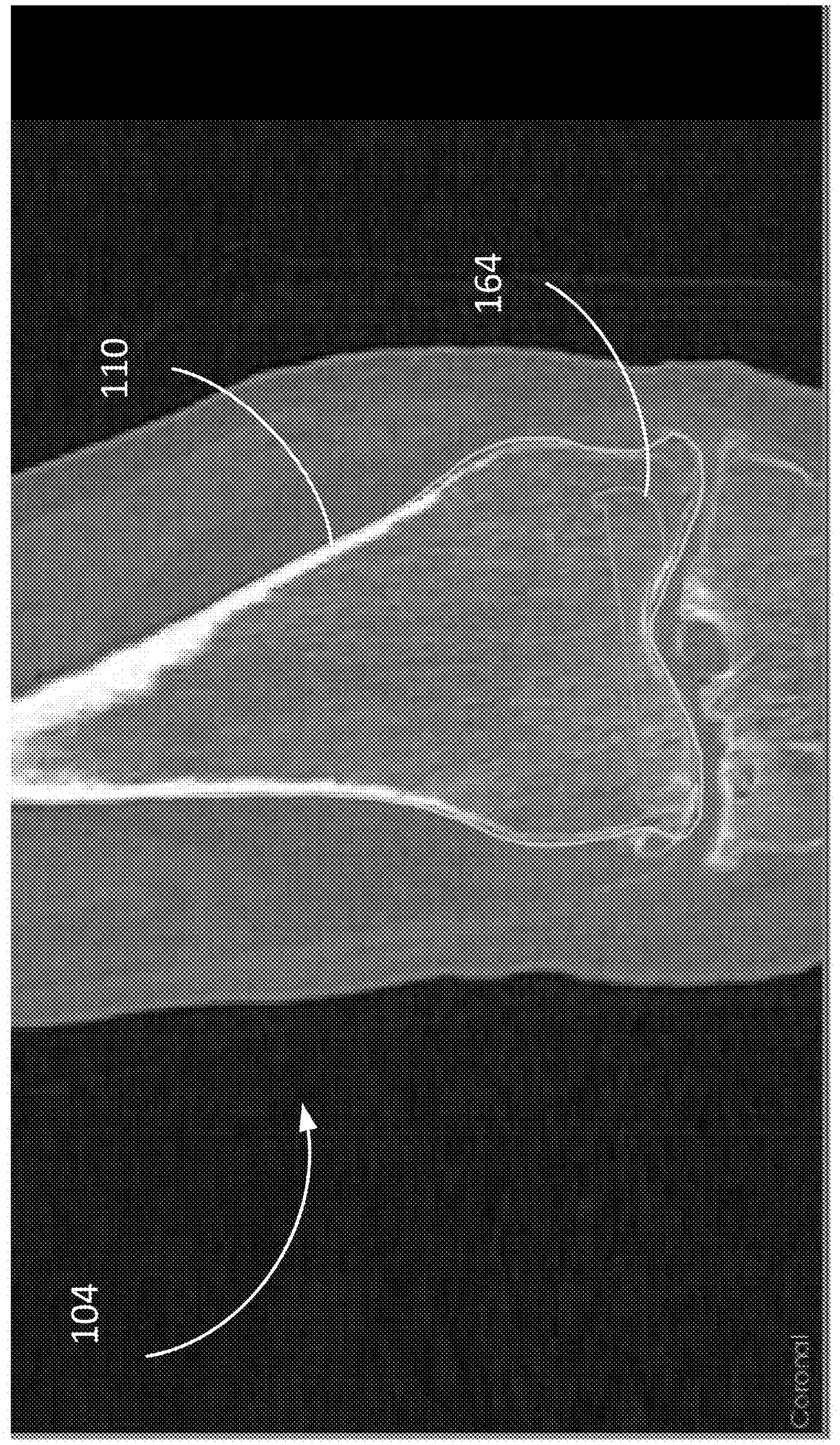
Figure 9D:
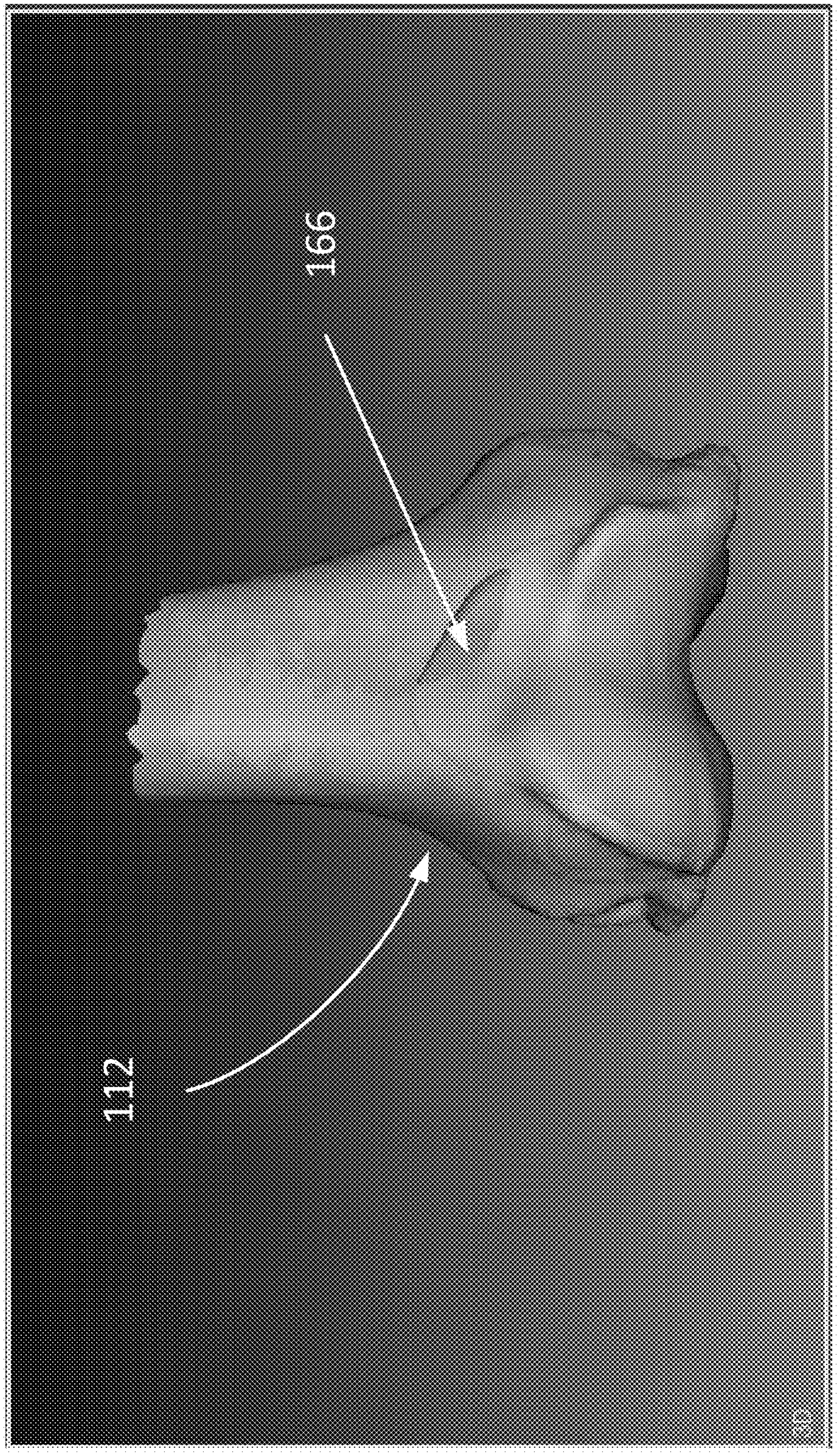
FIG. 9D is an anterior view of the three-dimensional implant model registered to the preoperative three-dimensional bone model.

FIGS. 9A-9C illustrate, respectively, axial, sagittal, and coronal views of the preoperative femur 104 overlaid with segmented cross-section lines 110, 164 of the preoperative 3D bone model 112 and the 3D implant model 166, respectively. FIG. 9D illustrates the 3D implant model 166 registered to the preoperative 3D bone model 112. Registration transforms the 3D implant model 166 to the preoperative 3D bone model 112, as seen in FIG. 9D, in the position and orientation it (3D implant model 166) was in relative to the postoperative 3D bone model 158. Thus, the position and orientation of the 3D implant model 166 relative to the preoperative 3D bone model 158 indicates how the implant was surgically implanted on the bone. This information can be used to determine the accuracy of the actual surgical implantation of the implant relative to the planned implantation position and orientation of the implant. In a certain instance, the preoperative plan may be registered to the combined models 112, 166 to determine the accuracy of the implant placement relative to the planned placement. In certain instances, the preoperative plan may be part of the preoperative bone model 112.

Turning back to FIG. 5, the method 500 may include identifying the position and orientation of the post-surgical models 166, 158 relative to the preoperative 3D bone model 112, at step 516. As stated prior, registering the 3D implant model 166 to the preoperative 3D bone model 112, as seen in FIG. 9D, transforms the 3D implant model 166 according to its position and orientation as it was actually, surgically implanted on the bone since its position and orientation relative to the postoperative 3D bone model 158 is known.

The preoperative 3D bone model 112 may include various planned resections, and drill holes, among other bone modifications associated with it. The resections and drill holes include a position (coordinate locations) relative to the 3D bone model 112 and an orientation (rotational orientation) as well to match the implant. And, the 3D implant model 166 includes surfaces designed to abut certain surfaces of the bone. For instance, the 3D implant model 166 may include posts and interior surfaces designed to abut the resected surfaces of the bone. Thus, when the 3D implant model 166 is overlaid on the preoperative 3D bone model 112, the inner surfaces and posts of the implant model 166 may be identified, at step 516 of the method 500 of FIG. 5, and then compared with the planned resection planes and drill holes on the preoperative 3D bone model 112, as indicated at step 518 of the method 500 of FIG. 5.

The comparison step 518 may indicate a positional and angular difference between, for example, a planned drill hole or resection plane associated with the preoperative 3D bone model 112 and an implant post location on the implant model 166 or a plane corresponding to an actual resection plane as indicated by a planar surface on the interior surface of the implant model 166. The comparison step 518 may also indicate changes in the joint line and posterior condyle offset, among other factors for comparison.

The comparison step 518 may indicate, generally, the differences between the planned bone modifications, and the actual bone modifications, as well as the differences between the planned implant placement and the actual implant placement.

V. Exemplary Bones and Procedures for Planning and Postoperative Analysis

While the previous sections describe preoperative imaging and planning, performance of surgery, and the postoperative analysis of the surgery with respect to a knee joint, the methods are also applicable to other procedures (i.e., besides total knee arthroplasty) and other parts of the body including without limitation partial-knee arthroplasty procedures, and the various types of procedures on the hip, ankle, shoulder, elbow, and wrist. Accordingly, the following sections will describe the systems and methods with respect to a partial knee arthroplasty and a total hip arthroplasty

A. Partial Knee Arthroplasty

Figure 10A:
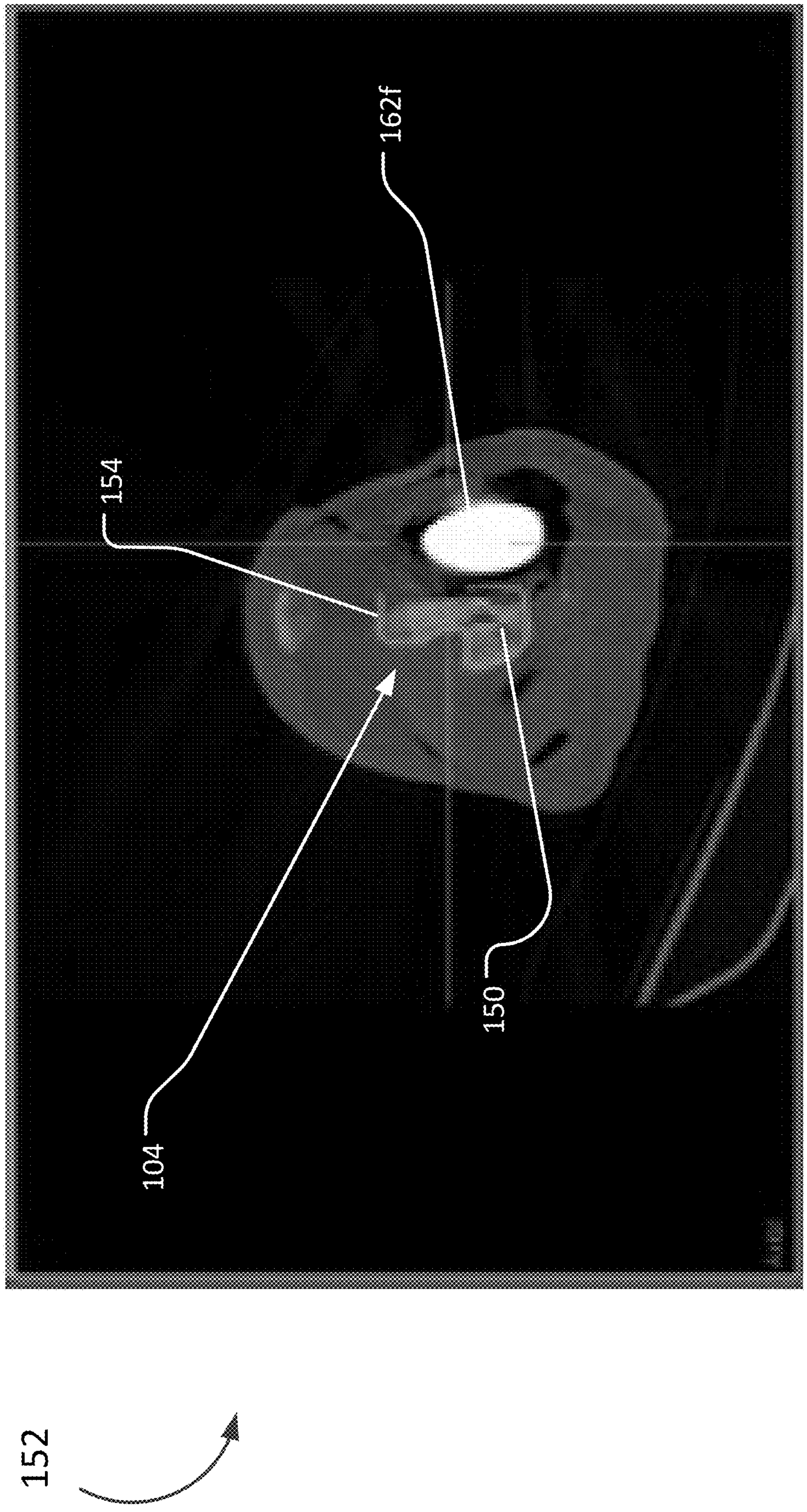
FIGS. 10A-10C are, respectively, axial, sagittal, and coronal images of a knee joint with a partial-knee implant positioned thereon overlaid with a segmented cross-section line of a postoperative three-dimensional bone-remainder model.

FIGS. 10A-12D depict steps in the method of imaging and analyzing the accuracy of a partial-knee arthroplasty (PKA). In particular, FIGS. 10A-10C depict, respectively, axial, sagittal, and coronal images of the knee joint generated postoperatively with a segmented cross-section line 154 of the 3D bone models of the femur and tibia 158*f*, 158*t* overlaid on the postoperative images of the femur 104 and tibia 106. The steps of imaging and analyzing the placement of the femoral and tibial implants 162*f*, 162*t* may follow the steps outlined in FIG. 5.

At step 502 of the method 500 of FIG. 5, the patient may undergo postoperative imaging. The patient may, for example, undergo a CT scan, MRI scan, or X-ray, among other types of imaging scans. In general, the postoperative imaging will show the prosthesis 162*f*, 162*t* implanted on the patient bone 150. As with the preoperative image scan, the postoperative image scan may be in the form of a DICOM file where individual 2D image scans or slices can be viewed along various reference planes (e.g., coronal, sagittal, axial).

Conventionally, it may be difficult for a surgeon to ascertain the postoperative alignment of an implant relative to the bone in a postoperative CT scan, for example, because the metal artifacts associated with the metal implant tend to obscure the alignment of the implant relative to the bone. Thus, the method 500 described herein describes a method of postoperative analysis of implant placement that obviates the issue with artifacts in CT scans. The method 500 also obviates the need for enhanced radiation thereby reducing metal artifacts. Conventionally, it may also be difficult for a surgeon to ascertain the postoperative alignment of an implant relative to the bone in a postoperative CT scan, because many of the anatomical landmarks used for planning are no longer present after surgery. The method of registration of post-operative bone to pre-operative bone described above helps to overcome this difficulty.

Figure 10B:
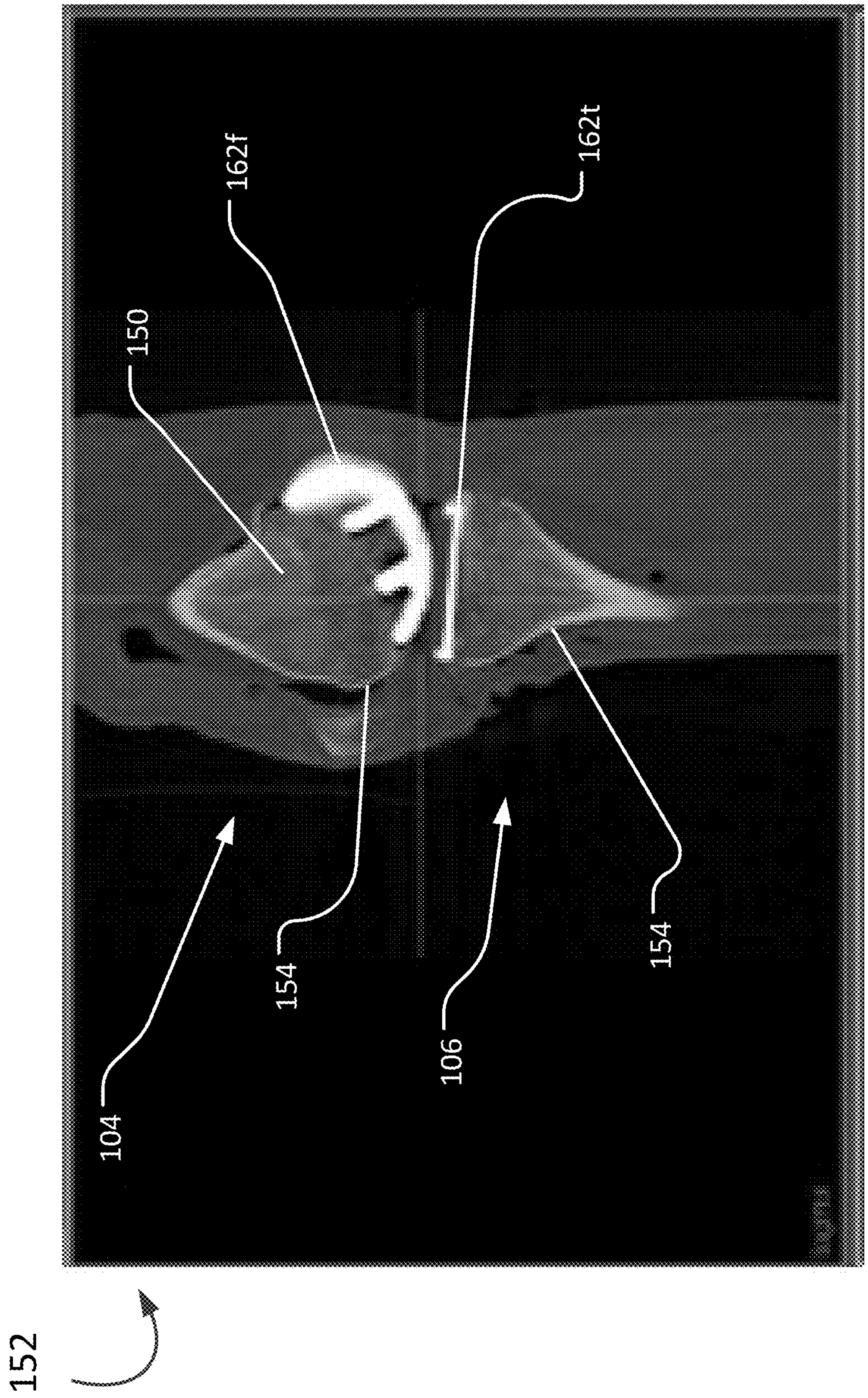
Figure 10C:
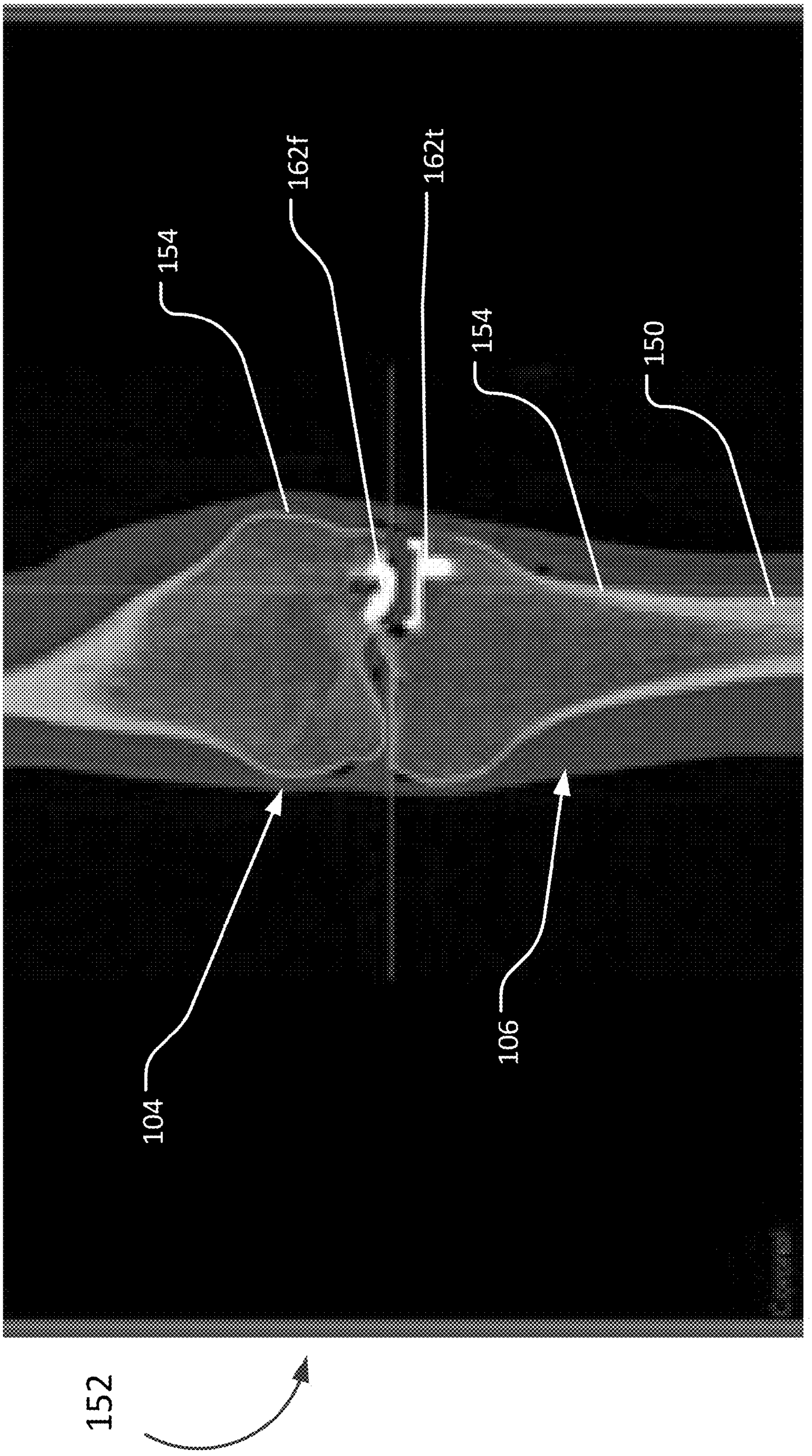

At step 504 of FIG. 5, and as seen in FIGS. 10A-10D, the post-surgical bone 150 may be segmented in the postoperative images 152 (also called post-surgical images). FIGS. 10A-10C illustrate, respectively, an axial view of the postoperative images 152 with a segmented cross-section line 154 of the 3D bone models 158*f*, 158*t* overlaying the bone 150, a sagittal view of the postoperative images 152 with the segmented cross-section line 154 of the 3D bone models 158*f*, 158*t* overlaying the bone 150, and a coronal view of the postoperative images 152 with the segmented cross-section line 154 of the 3D bone models 158*f*, 158*t* overlaying the bone 150. As seen in the figures, the bone 150 is segmented as evident by the segmented cross-section line 154 bounding the bone, not the implants 162*f*, 162*t*. That is, the segmented cross-section line 154 extends along the bones 150 up until the implant 162*f*, 162*t* where the segmented cross-section line 154 stops. The method 500 may also include, at step 506 of FIG. 5, generating a 3D bone model 158*f*, 158*t* of the segmented post-surgical bones of the femur 104 and tibia 106. As described in the previous sections, the steps of segmentation and generation of a bone model may be combined into a single step such as when utilizing an AAM process.

Figure 10D:
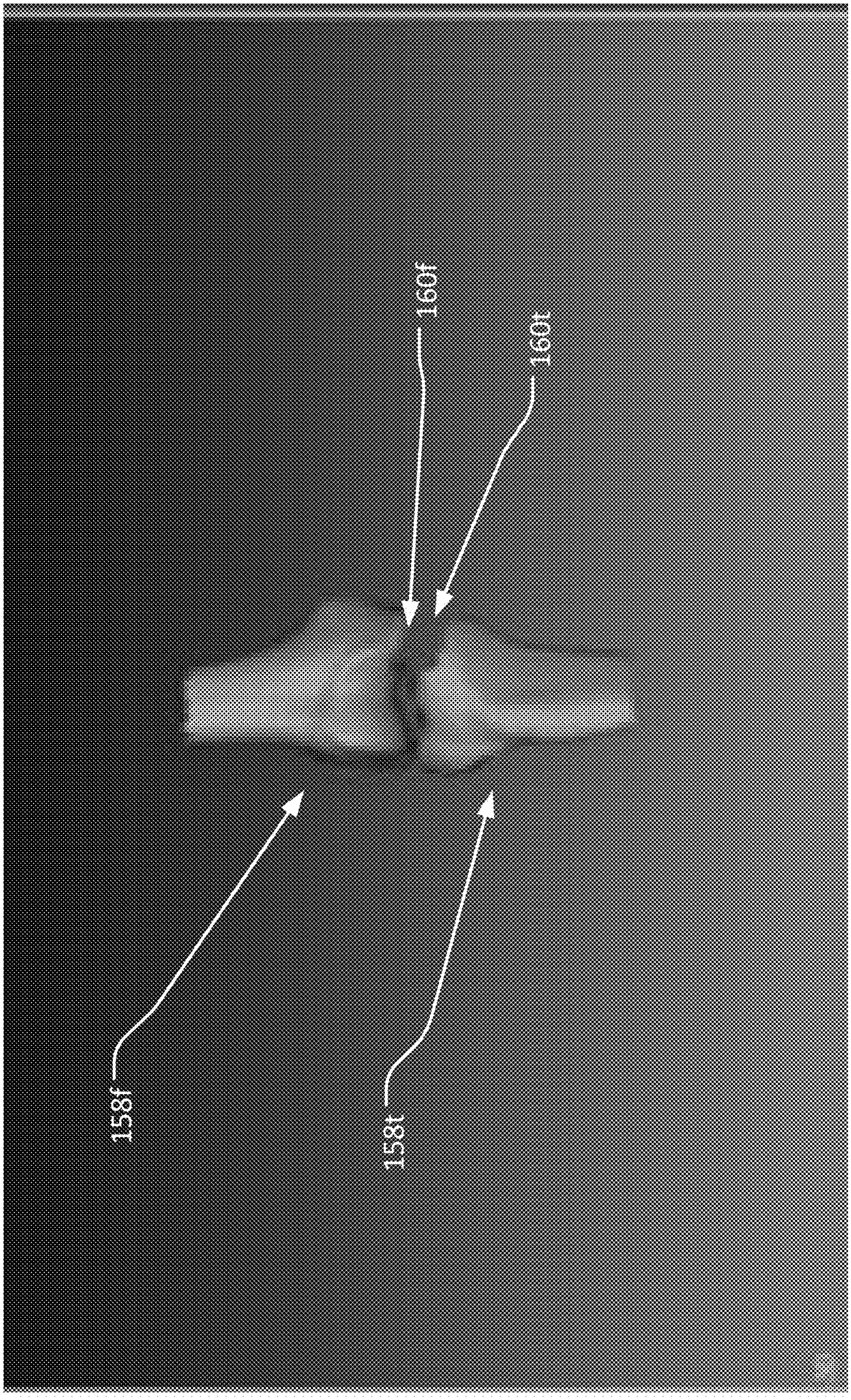
FIG. 10D is an anterior view of a postoperative three-dimensional femur and tibia bone-remainder model generated from the postoperative segmentation process.

As seen in FIG. 10D, which is a front view of the 3D bone model 158*f*, 158*t* of the segmented post-surgical bone, there is a void space 160*f*, 160*t* where the implants for a partial-knee arthroplasty would be. In one instance, the medial femoral condyle and medial tibial plateau may be defined by a void space 160*f*, 160*t* where the implant 162*f*, 162*t* was positioned. An in another instance, the lateral femoral condyle and lateral tibial plateau may be defined by a void space 160*f*, 160*t* where the implant 162*f*, 162*t* was positioned.

As described with reference to the preoperative imaging, the step 506 of generating a 3D bone model 158*f*, 158*t* may involve a generic or statistic bone model that is modified or best fit to the patient's bone. And while step 504 describes "segmenting" the post-surgical bone, other methods may be employed that identify and extract the bone from the postoperative images 152 without specifically applying a spline 154 to the bone contours 150.

Figure 11A:
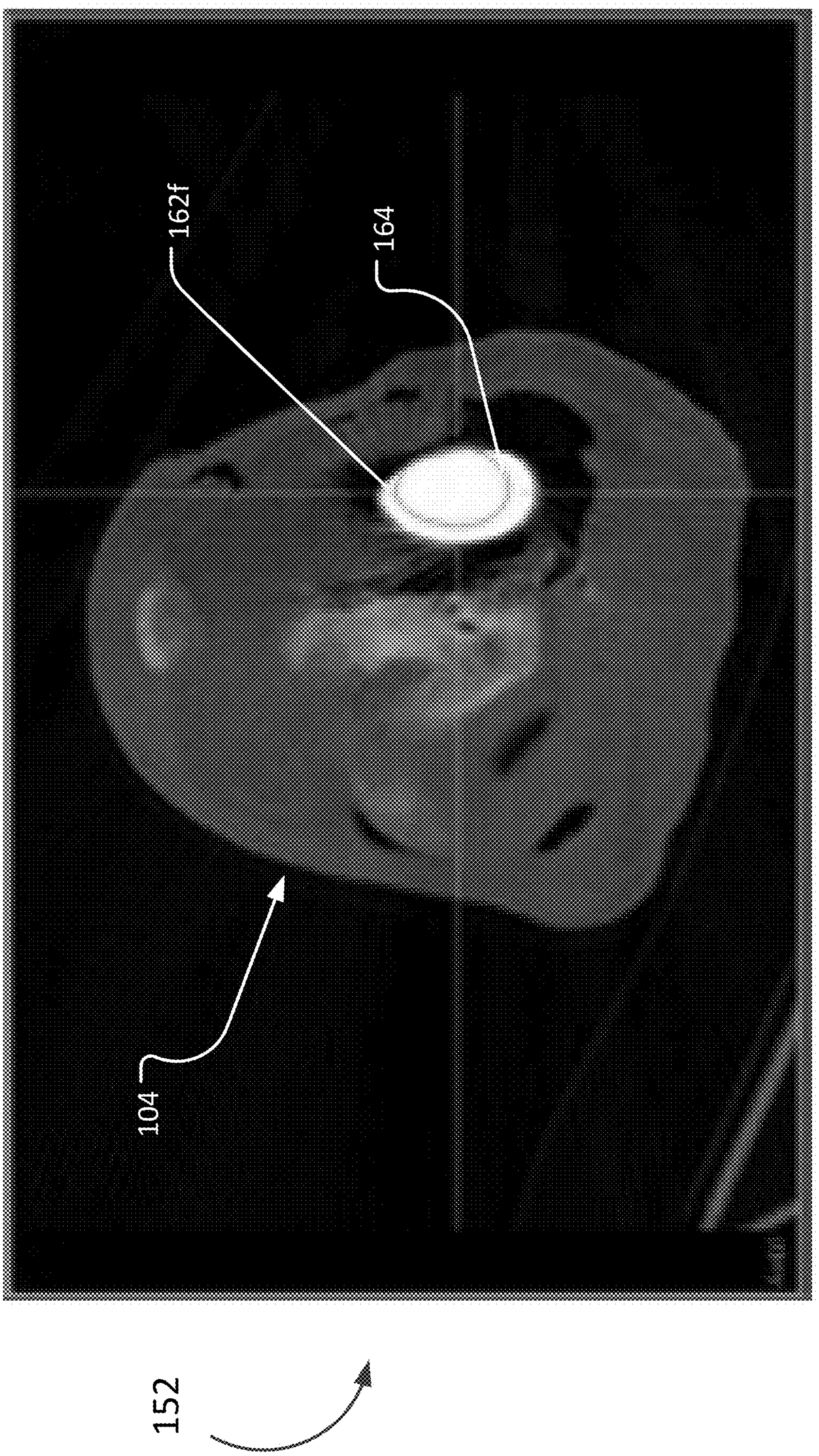
FIGS. 11A-11C are, respectively, axial, sagittal, and coronal images of the knee joint with a partial-knee implant positioned thereon overlaid with a segmented cross-section line of a three-dimensional implant model.
Figure 11B:
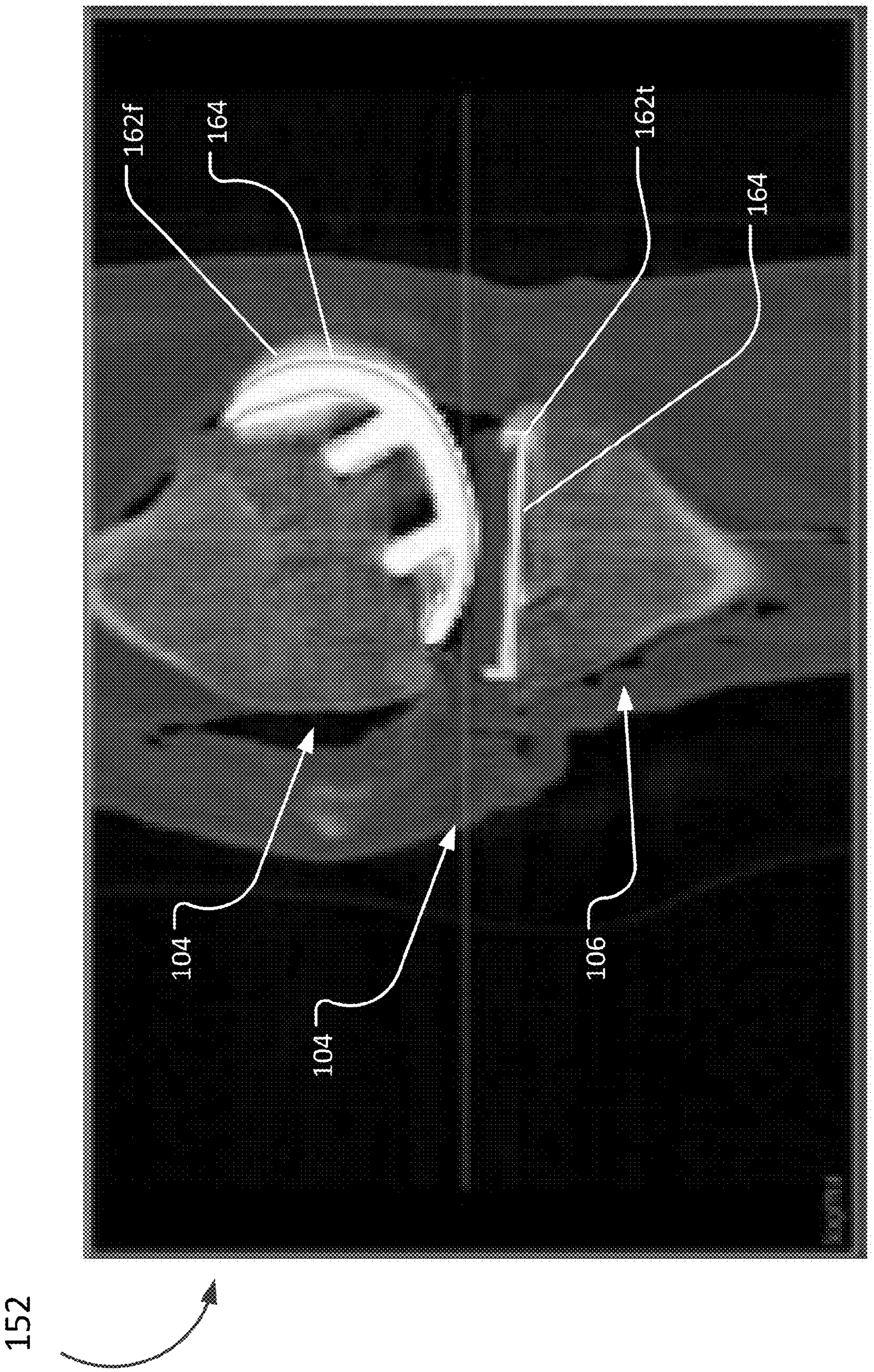
Figure 11C:
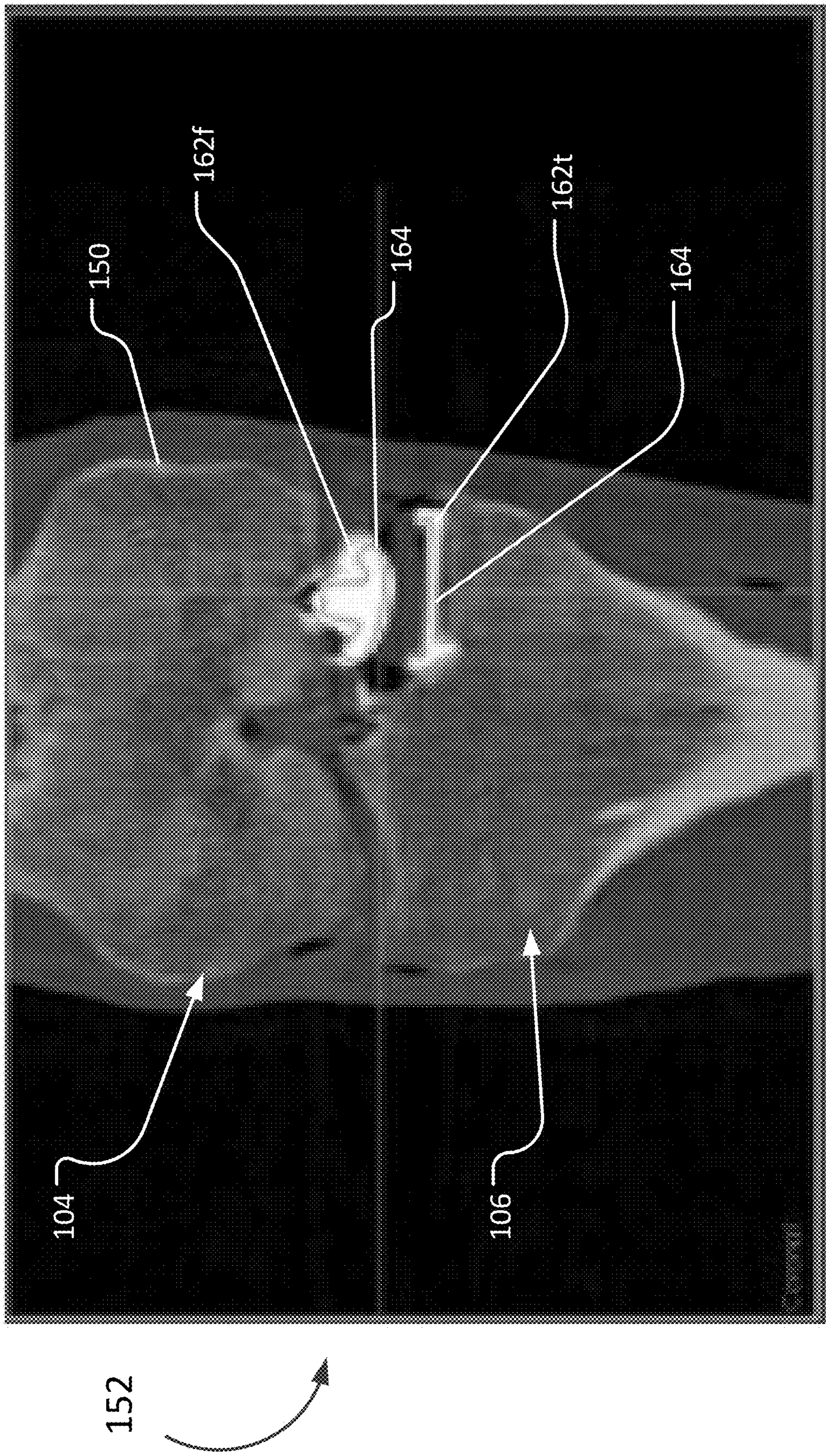
Figure 11D:
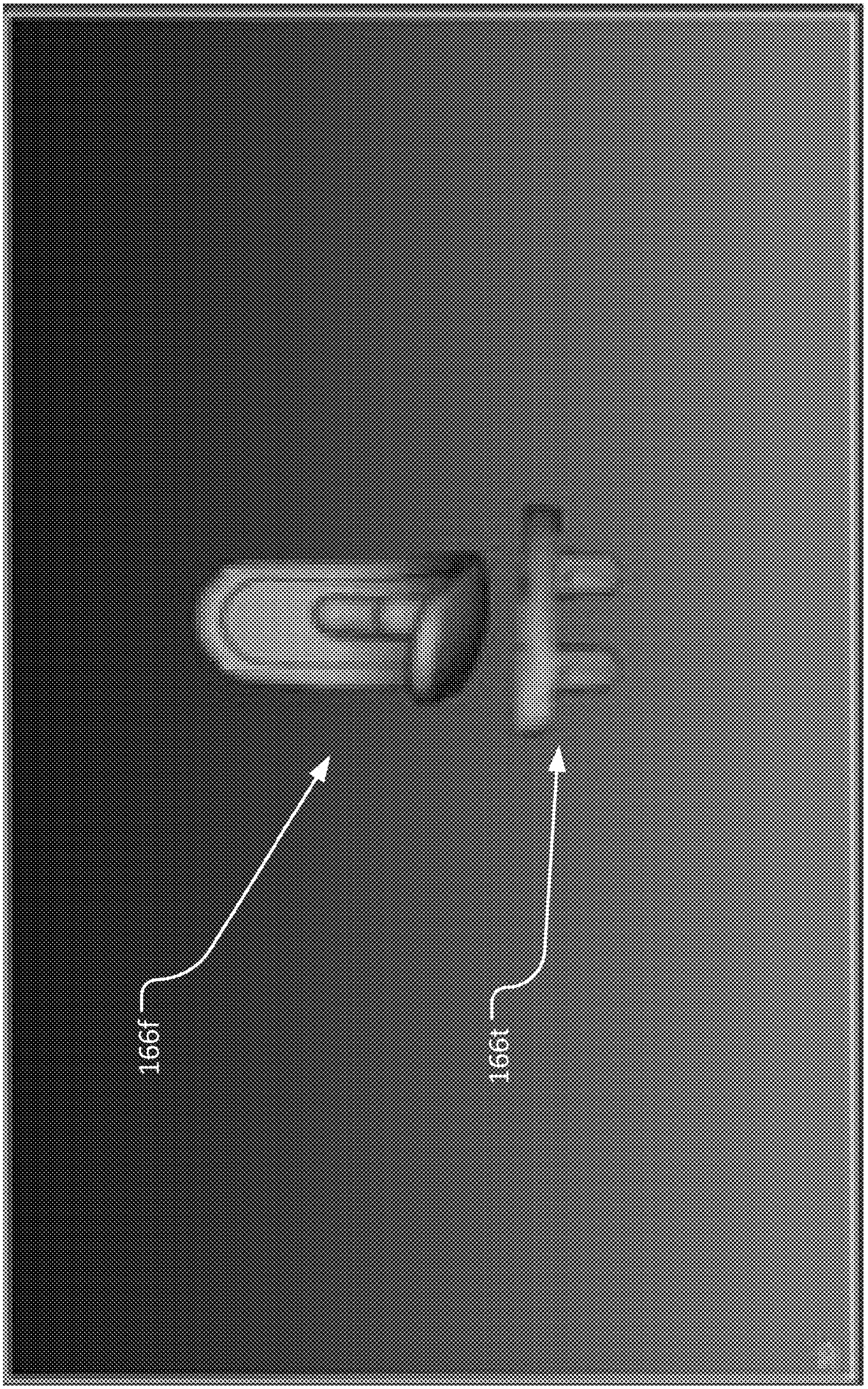
FIG. 11D is an anterior view of a three-dimensional implant model.

Turning back to FIG. 5, following the postoperative imaging step 502, the method 500 may include segmenting the implant 162*f*, 162*t* from the postoperative images 152, at step 508. FIGS. 11A-11C, illustrate, respectively, an axial view of the postoperative images 152 overlaid with a segmented cross-section line 164 of the 3D implant model 166*f*, 166*t* generally positioned over the contour of the implant 162*f*, a sagittal view of the postoperative images 152 overlaid with a segmented cross-section line 164 of the 3D implant model 166*f*, 166*t* generally positioned over the contour of the implant 162*f*, 162*t*, and a coronal view of the postoperative images 152 overlaid with a segmented cross-section line 164 of the 3D implant model 166*f*, 166*t* generally positioned over the contour of the implant 162*f*, 162*t*. In this step 508, the bone is not segmented, only the implant 162*f*, 162*t* is segmented. That is, the implant 162 in each of the postoperative images 152 is segmented and identified by the segmented cross-section line 164 overlaid on the image. It can be appreciated in FIGS. 11A-11C, among others, that the boundary between the implant and bone in the CT images is blurred and thus difficult to ascertain because of the high contrast associated with the metal implant. For at least this reason, it may be difficult to accurately apply splines to the images, and then generate a 3D model based on the splines. Segmenting the images utilizing a mathematical modeling algorithm (e.g., AAM) can eliminate much of the errors and uncertainties with applying splines.

The method 500 may also include, at step 510 of FIG. 5, generating a 3D implant model 166*f*, 166*t* (e.g., a femoral implant model 166*f*, and a tibial implant model 166*t*). Alternatively, a 3D implant model 166 may be provided from the manufacturer and used to build a 3D segmentation model with the same technologies used for segmenting bone (e.g. AAM, Random Forests, Graph Cuts, Deep Learning). This is described in more detail in the subsequent sections. From steps 504 and 508 of FIG. 5, the position and orientation of the implant 162*f*, 162*t*, as implanted, is known relative to the bone remainder. As described with reference to the preoperative imaging, the step 510 of generating a 3D implant model 166*f*, 166*t* may involve a generic or statistic implant model that is modified or best fit to the image. And while step 508 describes "segmenting" the implant, other methods may be employed that identify and extract the implant from the postoperative images 152.

Figure 12A:
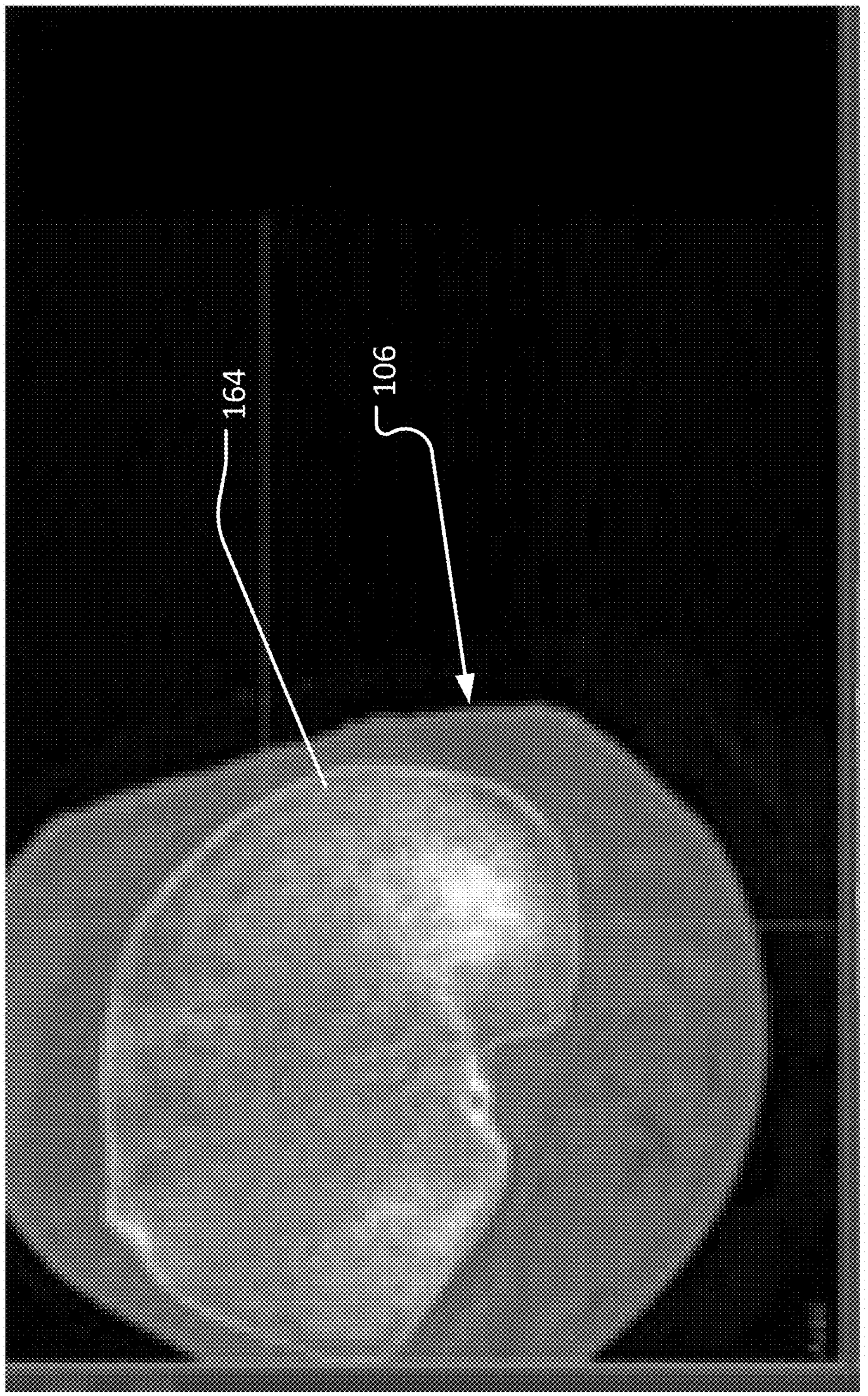
FIGS. 12A-12C are, respectively, an axial, a sagittal, and a coronal view of preoperative images of the knee joint overlaid with the segmented cross-section line of the three-dimensional implant model in a position and orientation of the implant as actually implanted on the bone.
Figure 12B:
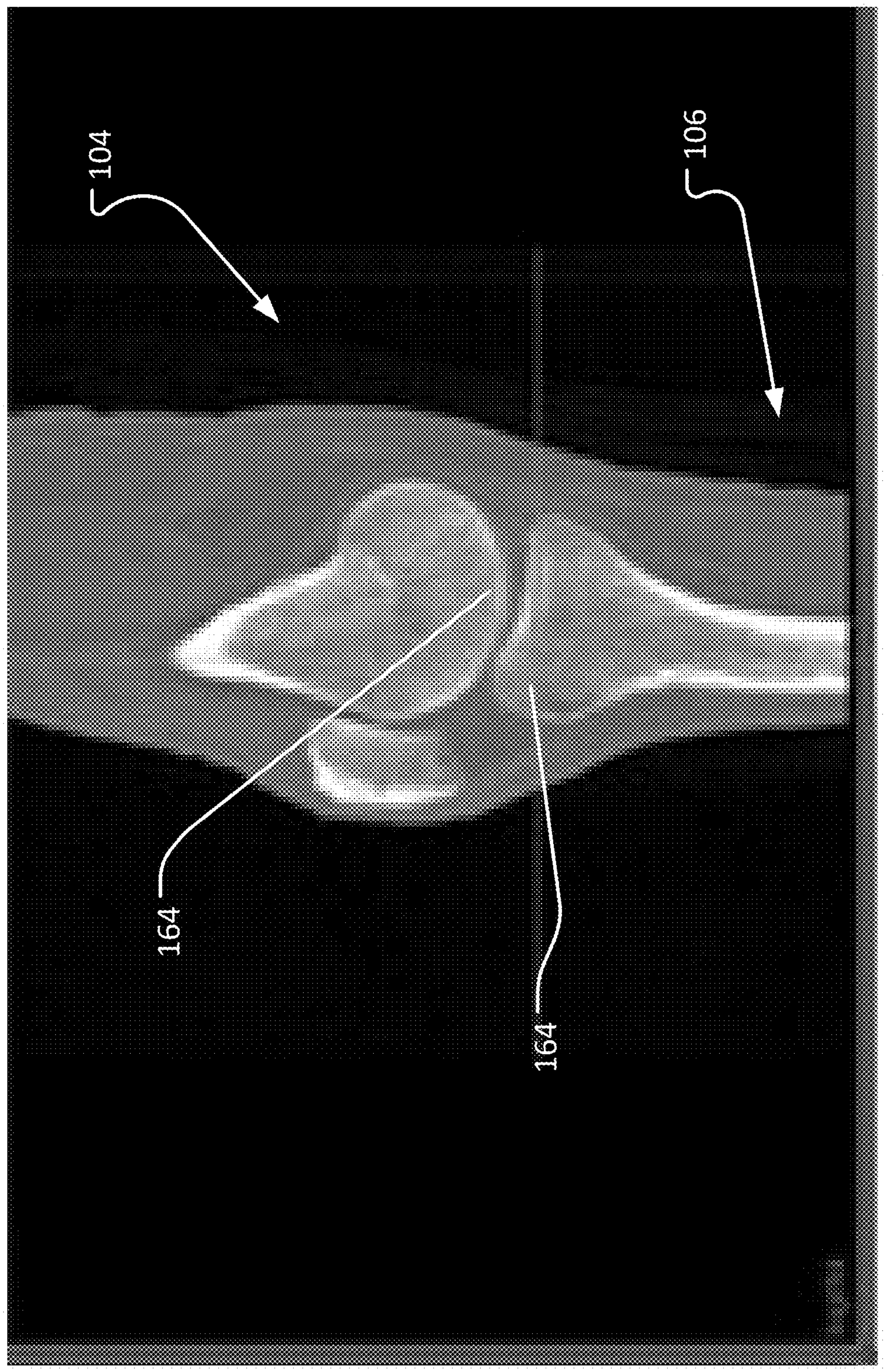
Figure 12C:
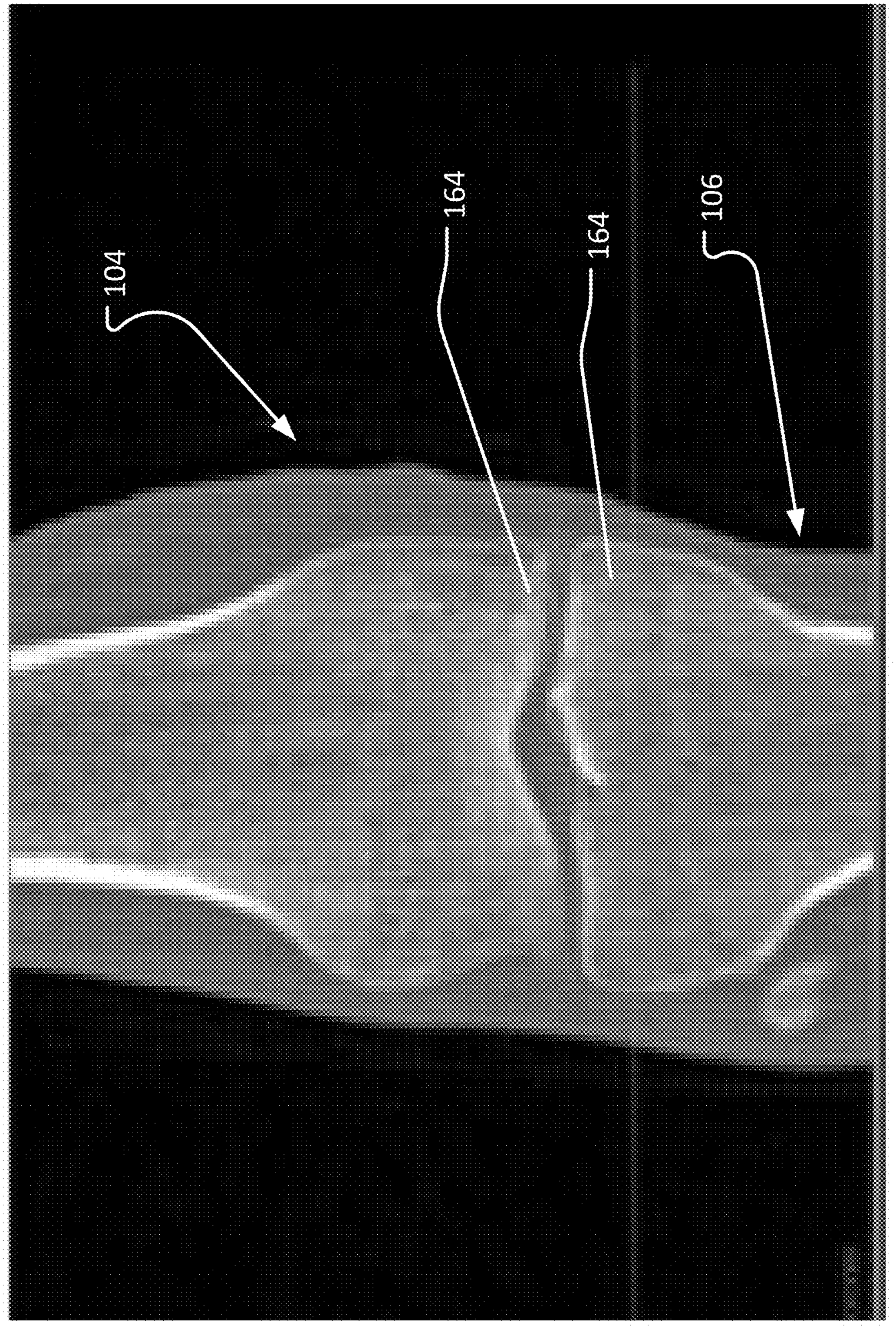
Figure 12D:
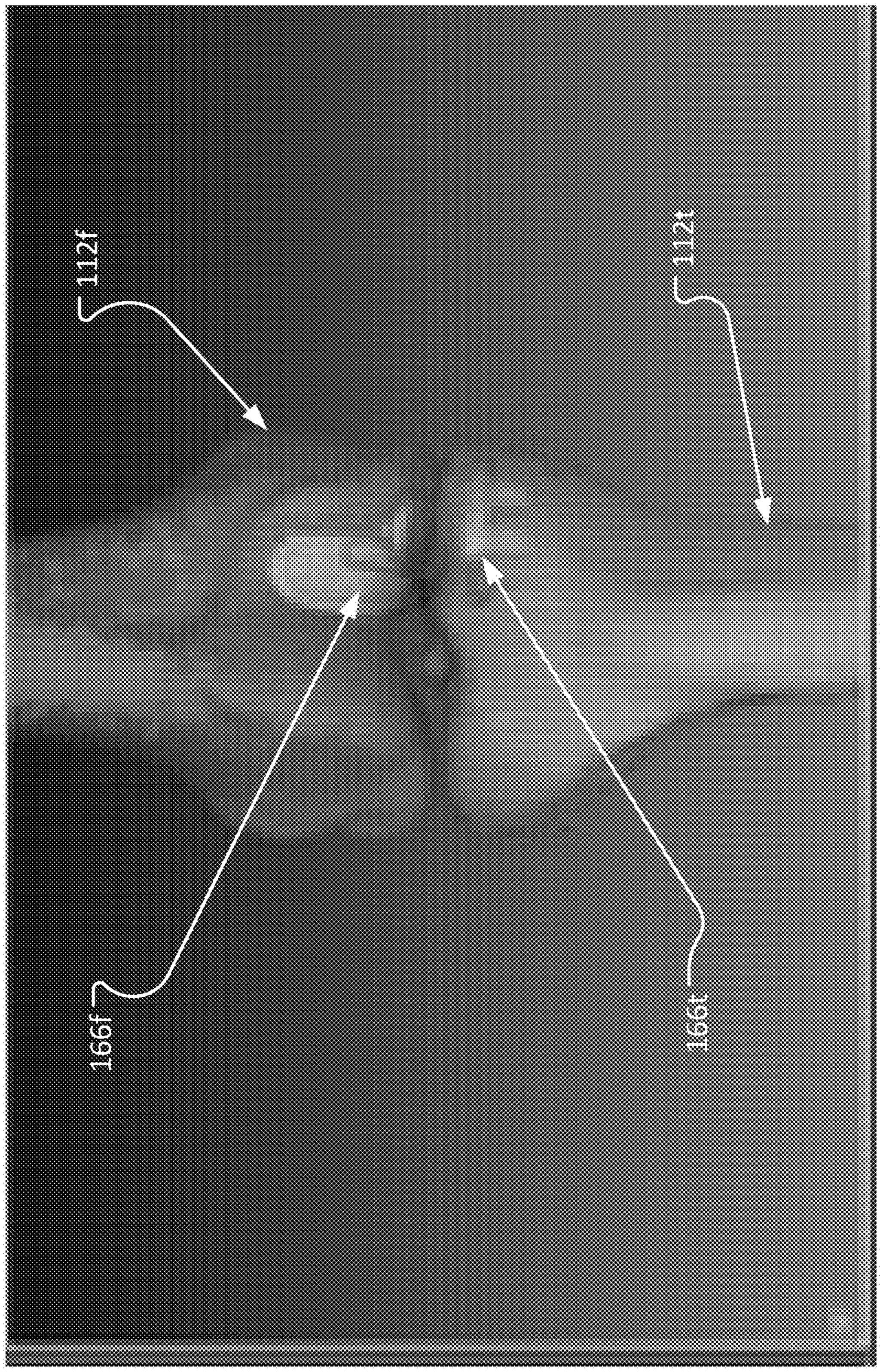
FIG. 12D is an anterior view of a preoperative three-dimensional bone model of the patient's knee overlaid with the three-dimensional implant model in a position and orientation of the implant as actually implanted on the bone.

Turning to FIG. 5, the method 500 may include registering the 3D bone model 158*f*, 158*t* generated from the post-surgical bone to a preoperative bone model 112*f*, 112*t*, at step 512. The method 500 may include registering the 3D implant models 166*f*, 166*t* to the preoperative bone models 112*f*, 112*t* according to its position and orientation relative to the bone remainder, at step 514. FIGS. 12A-12C illustrate, respectively, axial, sagittal, and coronal views of preoperative images of the femur and tibia 104, 106 overlaid with segmented cross-section lines 164 of the 3D implant models 166*f*, 166*t*. And FIG. 12D illustrates the preoperative bone models 112*f*, 112*t* overlaid with the 3D implant models 166*f*, 166*t* according to the position and orientation of actual implanted implant. It is noted there is no figure showing the postoperative 3D bone models 158*f*, 158*t* registered to the preoperative 3D bone model 112*t* prior to the preoperative bone models being overlaid with the 3D implant models 116*f*, 166*t*, but such a step may be included in the method.

The position and orientation of the implant as it was implanted is known by the relation of the implant to the bone in the postoperative images 152. The postoperative bone and implant may be segmented, separately, in steps 504, 508 of FIG. 5. The 3D bone models of the preoperative bone and the postoperative bone may be registered relative to each other by point-to-point least-squares fitting, iterative closest point (ICP), point-to-surface distance minimization, or any known method. And since the position and orientation of the implant model relative to the postoperative bone model is known, the position and orientation of the implant model may be overlaid relative to the preoperative bone model to show how the implant was actually implanted relative to an unresected or pre-surgical bone model (step 516 of FIG. 5). From this point, a comparison can be made of the post-surgical position and orientation of the implant relative to the planned implant position and orientation, at step 518.

The results of the comparison of the post-surgical position and orientation of the implant relative to the preoperatively planned position and orientation of the implant can be used for a variety of purposes including determining whether or not a follow-up procedure is needed (e.g., revision surgery), to diagnose potential problems (e.g., certain types of wear on the implant), and/or to improve the planning process.

B. Hip Arthroplasty

In addition to postoperatively determining the accuracy of knee implant placement via the methods described in this application, the methods may be used on other joints of the body including the hip, ankle, shoulder, elbow, and ankle. This section describes measuring the accuracy of a hip arthroplasty procedure.

Figure 13A:
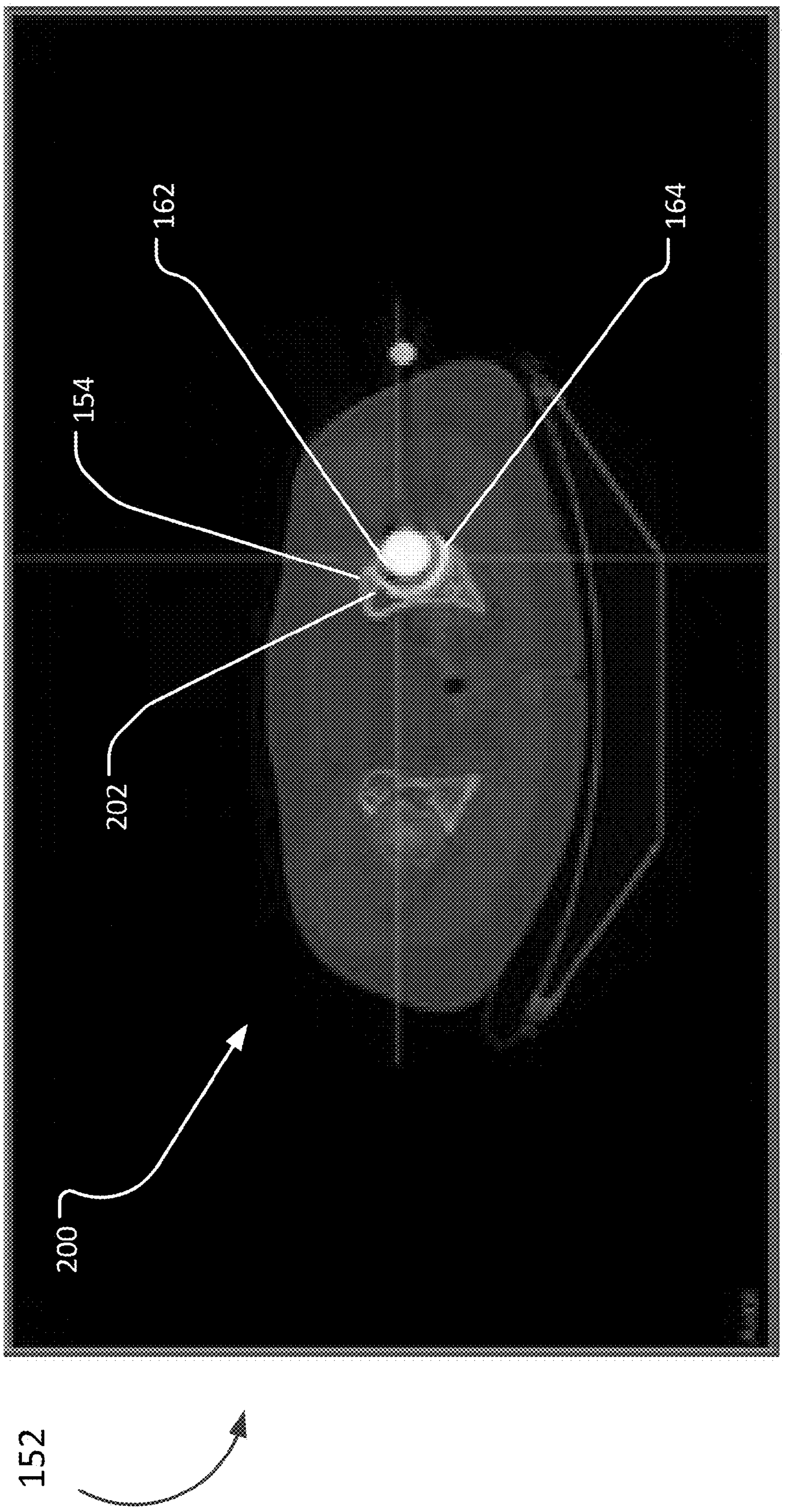
FIGS. 13A-13C are, respectively, an axial, a sagittal, and a coronal view of a pelvic region of a patient showing segmented cross-section lines of the three-dimensional implant model and bone model.
Figure 13B:
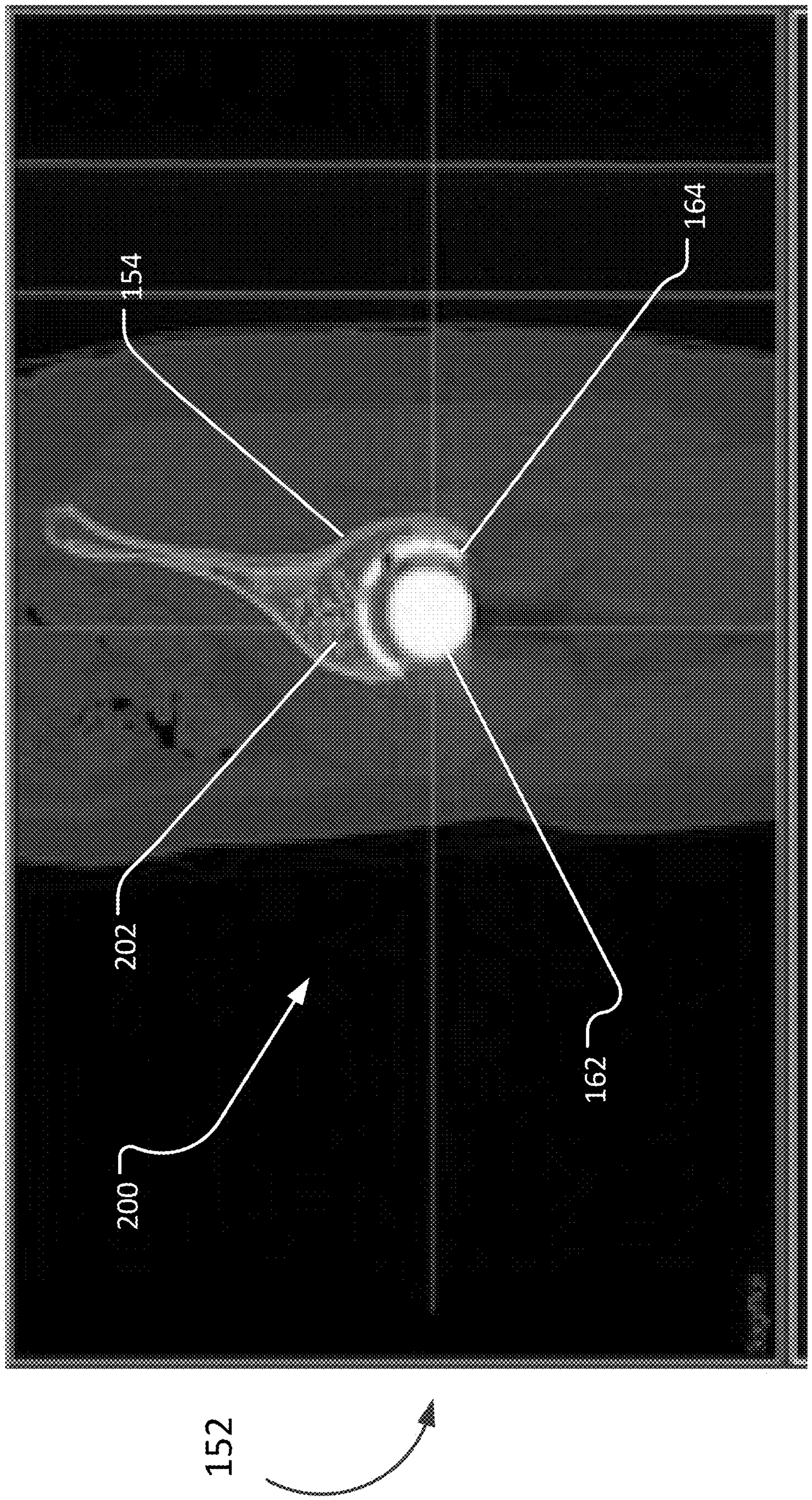
Figure 13C:
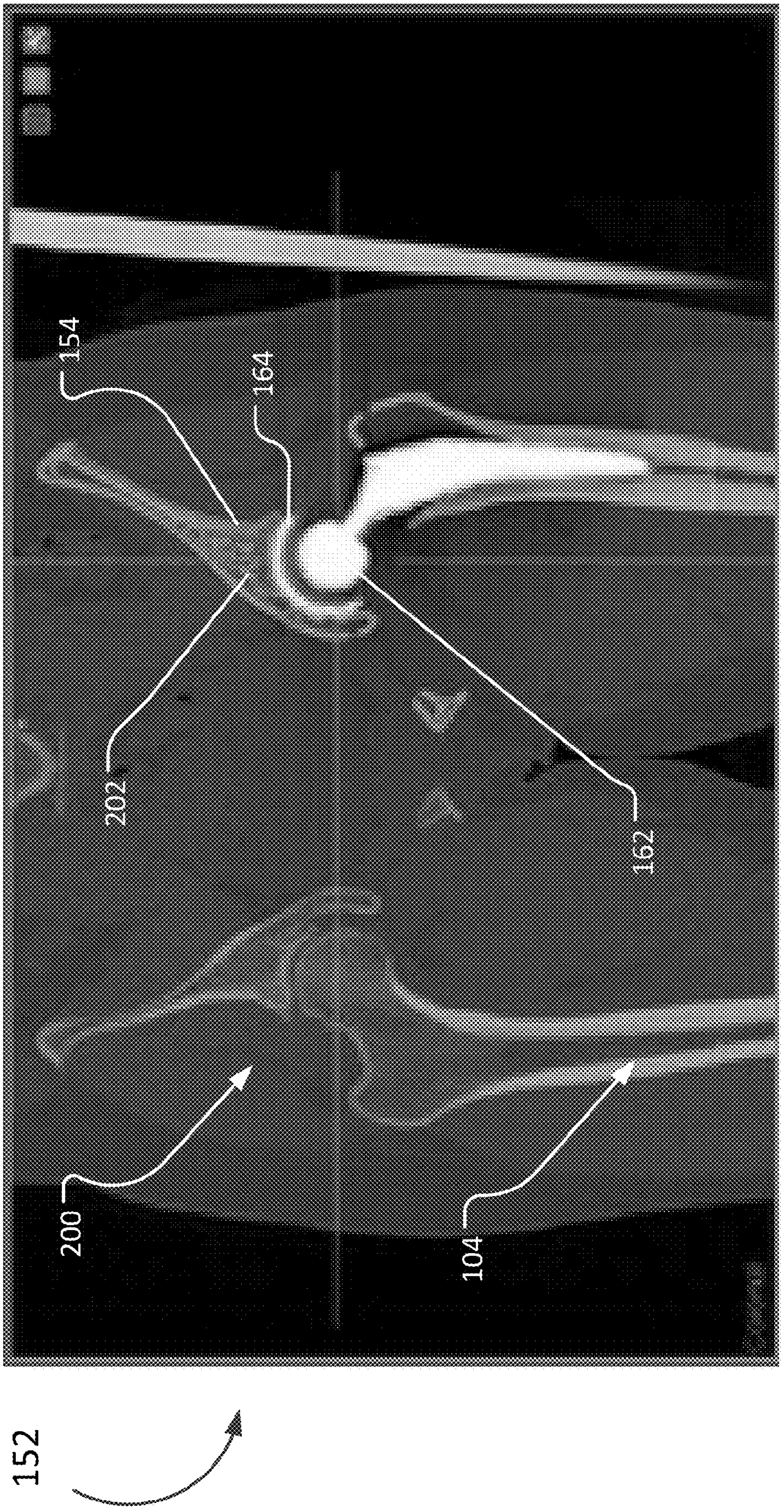
Figure 13D:
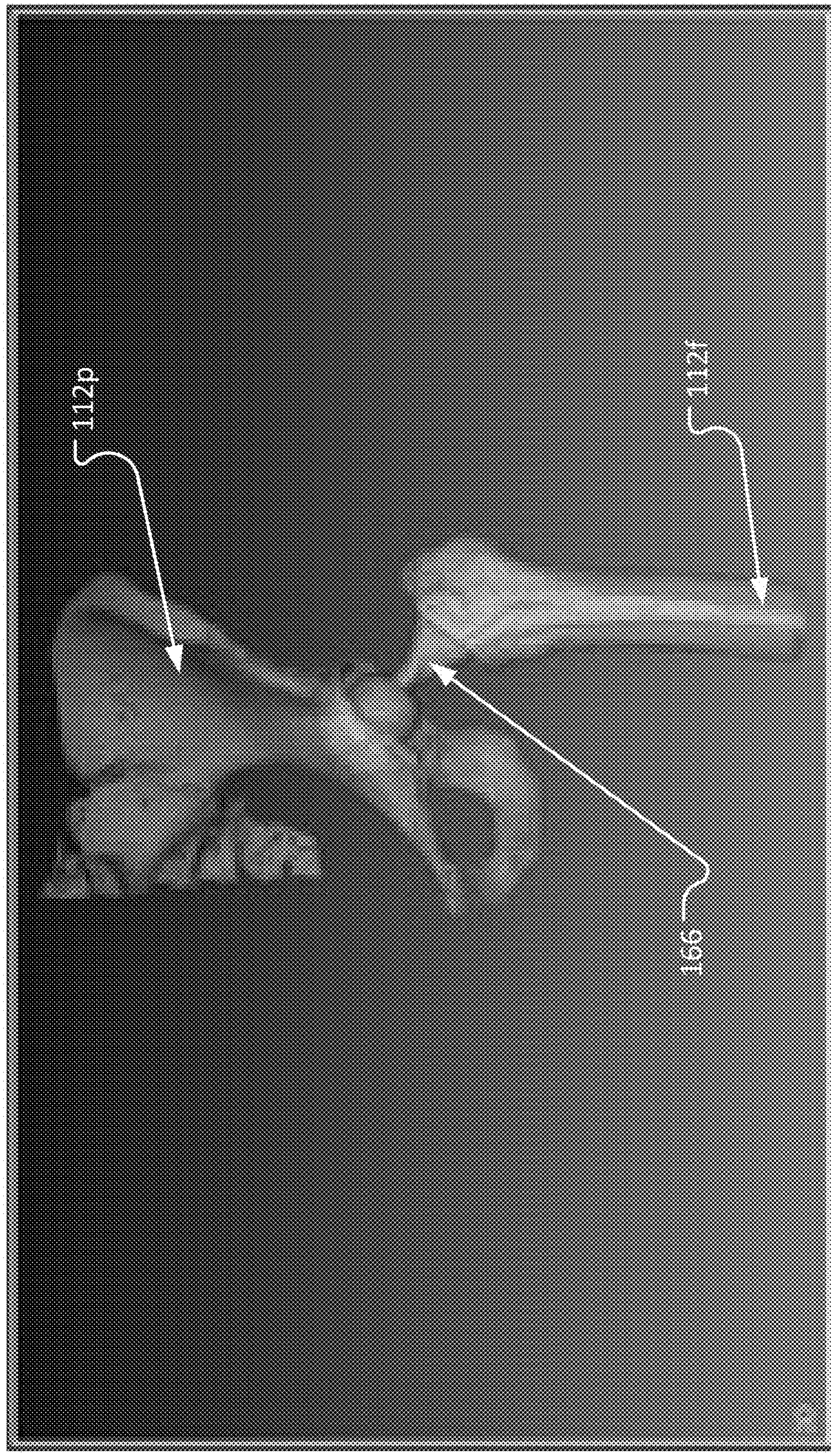
FIG. 13D is an anterior view of a preoperative three-dimensional bone model of the patient's pelvic region and femur overlaid with the three-dimensional implant model in a position and orientation of the implant as actually implanted on the bones.

FIGS. 13A-13C are, respectively, an axial view, a sagittal view, and a coronal view of a postoperative image 152 of a pelvic region 200 including an ilium 202 and a femur 104 with an implant 162 implanted in the ilium 202 and proximal femur 104. The posteroperative images 152 are overlaid with a segmented cross-section line 154 of a 3D bone model 112*p*, 112*f* of the pelvis region 200 and a segmented cross-section line 164 of a 3D implant model 166. FIG. 13D is a coronal view of the 3D implant model 166 positioned relative to the 3D preoperative bone model 112 (including a 3D pelvic model 112*p* and a 3D femur model 112*f*). It is noted that while the femur of the 3D bone model 112*f* is resected in FIG. 13D, the postoperative analysis is performed with the implant placement registered to the preoperative 3D bone model 112*f*.

The method or process for postoperative analysis of implant placement versus planned placement can be provided by the steps shown in FIG. 5. At step 502, the patient may undergo postoperative imaging (e.g., CT, MRI, X-ray). From there, the postoperative bone 104, 200 may be segmented from the postoperative images 152, at step 504. And, the implant 162 may be segmented from the postoperative images 152, at step 508. At step 506, a 3D bone model of the segmented postoperative bone 104, 200 may be generated. It is noted that steps 504 and 506 may be considered a single step. For example, when using an appearance model, the process of "segmentation" is the generation of a model.

On the implant side of the method 500, at step 510, a 3D implant model 166 may be generated from the segmentation of the implant at step 508. Additionally or alternatively, the 3D implant model 166 may be generated or acquired from the manufacturer of the implant 162. At step 512, the 3D bone model of the segmented postoperative bone 104, 200 may be registered to a preoperative 3D bone model 112. At step 514, the 3D implant model 166 may be registered to the preoperative 3D bone model 112. At this point, the position and orientation of the 3D implant model 166 may be identified relative to the preoperative 3D bone model 112, at step 516. And, the post-surgical position and orientation of the 3D implant model 166 may be compared to the position and orientation of the implant as preoperatively planned, at step 518.

Based on the comparison at step 518, a recommendation may be made for an additional surgical procedure such as, for example, a revision surgery. A revision surgery may be recommended if the post-surgical position and orientation of the 3D implant model 166 relative to the preoperative 3D bone model 112 deviated from the preoperatively planned implant position and orientation by a certain margin. Additionally or alternatively, the information from steps 516 and 518 may be used to enhance the segmentation process within the method 500.

VI. Exemplary Method of Planning and Postoperative Analysis

Figure 14:
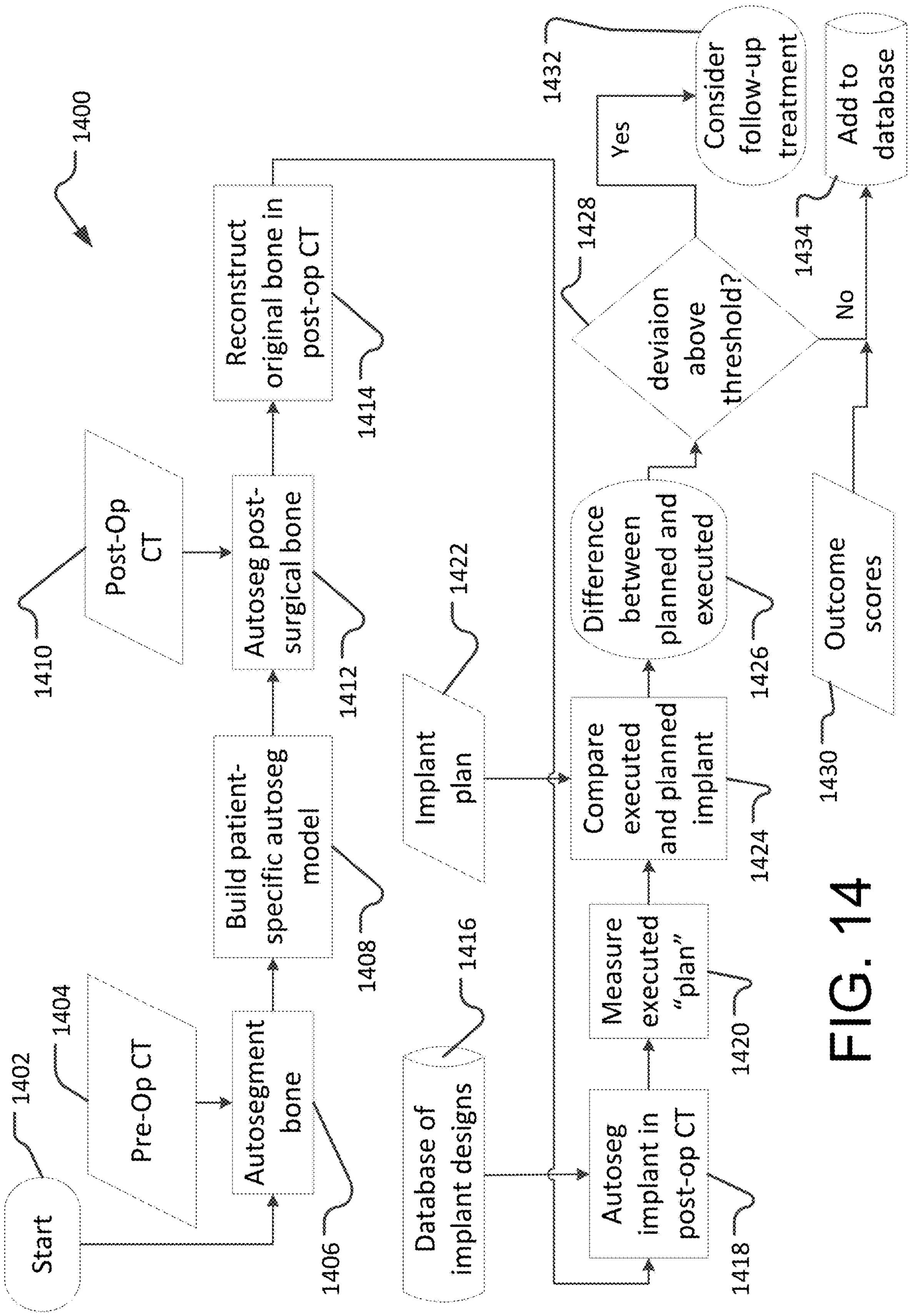
FIG. 14 is an exemplary method of analyzing postoperative implant placement versus planned implant placement.

FIG. 14 illustrates an exemplary flow diagram of a method 1400 of analyzing a surgical procedure. In particular, the method 1400 may be described as: a method 1400 of determining accuracy of a surgical procedure; a method 1400 of postoperative analysis of a surgical procedure; and a method of measuring surgical outcomes, among other descriptions.

The method 1400 of FIG. 14 may be applicable to all procedures described herein, among others. It is noted that the method 1400 may contain fewer or more than all steps shown in FIG. 14. The method 1400 shown in FIG. 14 is merely exemplary of an instance of postoperative analysis of a surgical procedure.

The method 1400 contains a series of steps or operations that begins at step 1402 with a patient preparing to undergo a surgical procedure. As part of the preparation, the patient may undergo a preoperative medical image scan (e.g., CT scan) at step 1404. From the medical image scan, one or more bones of interest associated with the surgical procedure may be segmented, at step 1406 (i.e., the segmentation may be automated, semi-automated, or manually performed by a user operating the computer). This step may include generating a a preoperative 3D bone model. Segmentation of the medical images may be the application of splines to the bone contour lines of 2D slices of the medical images as shown and described herein. Additionally or alternatively, the term segmentation may refer to morphing or otherwise fitting an active appearance model, a generic model, or a statistical bone model to the preoperative medical image scan so as to end up with a 3D bone model approximating the shape of the patient's bone(s).

Next, step 1408 may include building a patient-specific autosegmentation model based on the segmentation of the bone, as further described in Section VII.C. Preoperative planning of the surgical procedure may take place at this time. For example, a particular implant type and size may be chosen, and the planned position and orientation of the implant relative to the 3D bone model may be determined. The planned position and orientation of the implant may be determined to correct a varus or valgus deformity or to correct degeneration of a bone, among other conditions. After implant planning is complete, the surgery may be performed to correct the patient's condition.

Steps 1410 and beyond occur post surgery. Step 1410 includes undergoing a postoperative medical image scan on the portion of the body subject to operation. Step 1412 may include autosegmenting the postoperative bone from the postoperative image scan. This step isolates the postoperative bone from the implant within the imaging coordinate system. Step 1414 may include reconstructing the original bone in the postoperative medical images. For example, a statistical model trained on preoperative bones may be fitted to the remaining postoperative bone to provide an estimate or reconstruction of the regions removed in the previous surgery. Thus, the reconstructed bone in step 1414 represents the bone prior to surgery. Step 1418 may include autosegmenting the implant from the postoperative medical scans. This step may involve the searching and selecting an implant size and type from a database of implant designs, step 1416. Step 1418 isolates the implant from the bone within the imaging coordinate system.

Step 1420 measures the executed plan. Measuring the executed plan may entail steps 512, 514, and 516 of the method 500 of FIG. 5. The next step 1424 may include comparing the position and orientation of the implant as executed versus as planned. This step may pull the preoperative plan containing the specific information related to implant planning from a storage location, at step 1422. Step 1426 may include determining the differences between the position and orientation of the implant as executed versus as planned. The differences may be expressed as a measurement of: distance that is different along various axes (e.g., medial-lateral, anterior-posterior, distal-proximal); and rotation angles along the various axes. Step 1428 may compare the differences with certain thresholds. If the thresholds deviate beyond an allowable threshold, step 1432 may indicate that a follow-up treatment may be needed.

A follow-up treatment may be a revision surgery to correct the deviation of the executed surgery with what was planned. If the thresholds are within permissible parameters, the values may be added to a database at step 1434. The database may include the accuracy and outcomes of the procedures, which may be used to develop evidence-based planning algorithms for future use. Outcome scores (e.g., PROMs, function), at step 1430, may be determined from the parameters at step 1426, and may be stored in the database at step 1434. Various different outcome and functional measures may be recorded, for example Forgotten Joint Score (FJS), EQ-5D, Oxford Knee Score, Range of Motion (RoM), and these can be stored in the database for each patient alongside the preoperative surgical plan and the postoperative assessment of the implant positioning. Analysis of such a database may be performed to identify which surgical plans, or classes of plans, lead to positive or negative patient outcomes, and similarly to assess the impact of implant positioning accuracy on clinical outcomes.

VII. Image Analysis

A. Autosegmentation Technology

The methods described herein to generate the pre-operative 3D bone models 112 and/or the post-surgical 3D bone model 158 and/or the segmented 3D implant model 166 may be generated via a range of image processing and modelling technologies including, but not limited to, statistical modelling of shape, texture and appearance, and active appearance models, as well as manual or automatic segmentation employing 2D splines within each 2D slice of a CT or MR image, which are subsequently combined into a 3D surface. In certain instances, the models 112, 158, 166 (among others) may be fully 3-dimensional, and may use a 3D surface or volumetric model of anatomy to search a 3D volumetric image.

Appearance models, such as Active Appearance Models, combine information about the shape of the subject anatomy with its appearance as image features within the image. Many different image features may be included in the models, including but not limited to intensity, gradient, linear and non-linear transformations, and local filtering, which are computed at multiple scales and over multiple resolution derived images. These appearance models are statistical in nature because they are trained on a large set of images and thus model the variation of anatomical shape and image features across the target population. This enables them to find the most likely shape, size and pose of the subject anatomy in each new image, in which form they are referred to as Active Appearance Models (AAM). Other technologies used for automatic segmentation include Random Forests, Graph Cuts, and Deep Learning, for example. As described herein, the use of the term statistical model may include the use of an AAM, among the other types of segmentation and autosegmentation described herein. Additional information regarding Active Appearance Models can be found at the following locations, which are hereby incorporated by reference in their entireties: T. F. Cootes, G. J. Edwards and C. J. Taylor. (2001). "Active Appearance Models", IEEE PAMI, Vol. 23, No. 6, pp. 681-685; and Williams, T. G., Vincent, G., Bowes, M., Cootes, T., Balamoody, S., Hutchinson, C., Taylor, C. J. (2010). "Automatic segmentation of bones and inter-image anatomical correspondence by volumetric statistical modelling of knee MRI." IEEE Int. Symp. Biomed. Imaging: Nano Macro, ISBI-Proc. (pp. 432-435).

B. Labeling within Images of Implants and Imaging Artifacts

Reference is made here to CT images as an example, but similar techniques can be applied to other imaging modalities including X-ray, MRI, and ultrasound, among others.

The voxel intensities in CT images are measured in Hounsfield units, and these have known ranges for medical images. For example: air=−1000, water-based soft-tissues=0; cortical bone=+1000, and metal=+3000. In practice, these values are not exact because the various materials exhibit a distribution of intensities, and because any particular CT scanner may not be precisely calibrated. In certain instances, the use of a phantom can be used to determine the precise calibration of an image scanner, but that may not be necessary for the technology described here. Approximate calibration of the CT image to the Hounsfield scale may be sufficient, because the modelling algorithms are robust to significant variation of intensities in the image.

Various image processing techniques, including but not limited to thresholding, can be applied to assign, to each voxel in a medical image, a likelihood that it corresponds to air, soft tissue, bone, or implant, for example. This class of problem is often referred to as pixel or voxel classification which can be addressed by various technologies such as intensity thresholding, Random Forests, Graph Cuts and Deep Learning, for example.

For example, using intensity thresholding each voxel can be classified, independently from its neighbours, according to its intensity value. For example, if the voxel intensity exceeds 2,500 then that voxel is classified as implant. Voxels with intensities of about 0 may be classified as soft-tissue. And voxels with intensities of about +1,000 may be classified as bone. The aformentioned intensity levels are exemplary, and may change without limitation.

Figure 15:
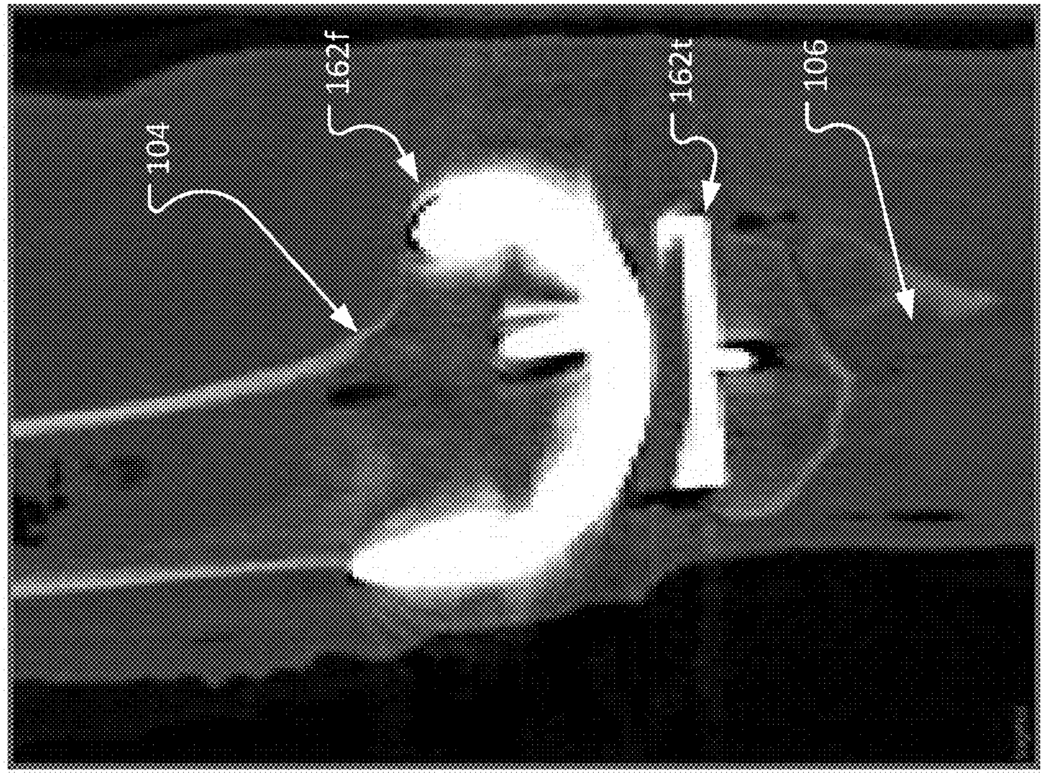
FIG. 15 is a sagittal view of a postoperative image of a femur and tibia with an implanted femoral component and tibial component.

Whichever classification method is employed, one or more classification images can be derived from the original image, as illustrated by FIGS. 15-18. FIG. 15 is a sagittal view of a postoperative CT scan showing a femur 104 and tibia 106 with an implanted femoral component **162*f* and a tibial component 162*t*. As seen in the figure, the implant components 162*f*, 162*t* are nearly a solid white color as compared with the greyscale bone surrounding the implant components 162*f*, 162*t***. Using intensity thresholding, each voxel in the image can be classified based on an intensity value. As an example, voxel intensities greater than 2,500 are classified as "implant", and voxel intensities less than 2,500 and about 1,000 are classified as "bone." Voxels having an intensity of about 0 are classified as soft tissue.

Figure 16:
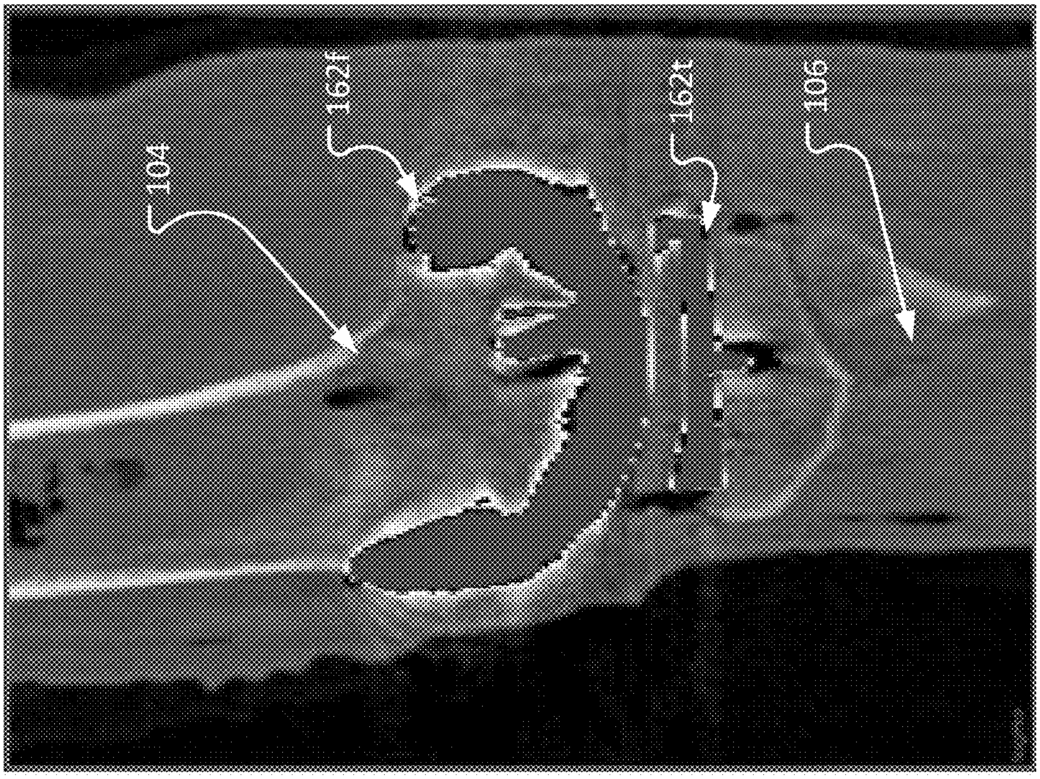
FIG. 16 is the same image as FIG. 15, except the voxels having intensities over 2500, which correspond to the implant, are colored.

Moving to FIG. 16, which shows the same sagittal view of a postoperative CT scan of the femur 104 and tibia 106, the voxels of the image with a voxel intensity of 2,500 or greater are colored in red, indicating the location of an implant. It is noted that while FIG. 16 only shows a single sagittal view illustrating the identification of certain "implant" voxels, the identification and labeling of voxels can be done for the entire CT image in three-dimensions, which will yield identifications of "implant", "bone", and "soft tissue" throughout all voxels of the CT image.

Figure 18:
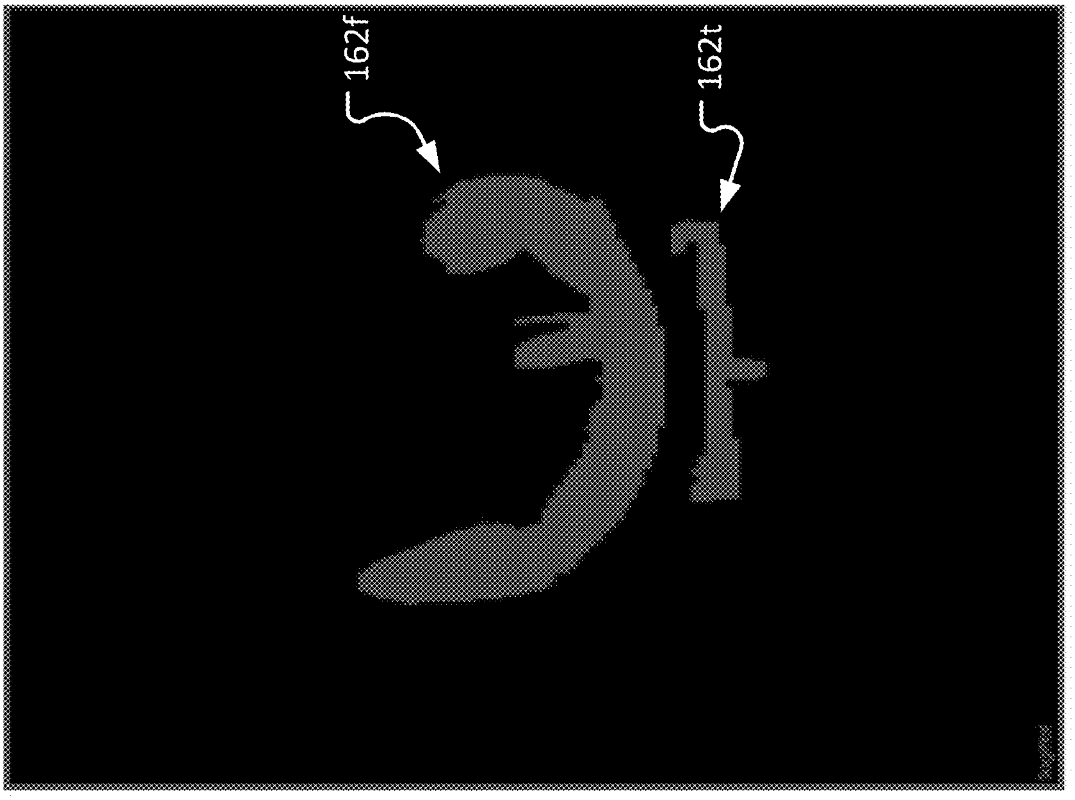
FIG. 18 is a sagittal view of the implant indicated by voxels having intensities over 2500.
Figure 17:
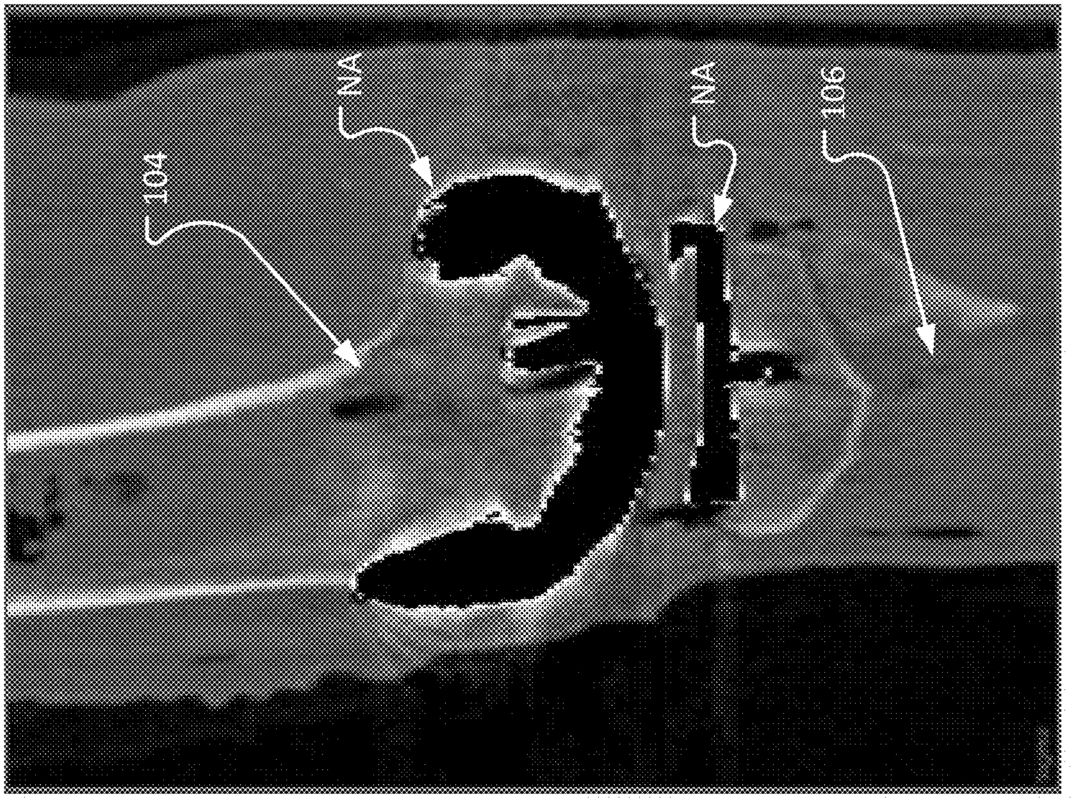
FIG. 17 is the same image as FIG. 16, except the voxels having intensities over 2500 are removed or suppressed from the image.

Next, FIG. 17 illustrates the same sagittal view of a postoperative CT image of the femur 104 and tibia 106, but with the voxels classified as "implant" have been suppressed or removed from the image. As seen in the figure, the voxels shown in red in FIG. 16, are now completely black or void of color, indicating their removal from the image. Again, while FIG. 17 illustrates only a sagittal image view of the CT image, it can be appreciated that the entire CT image has the "implant" voxels removed. The removed "implant" voxels are shown in FIG. 18, in a sagittal view. The aforementioned process of assigning voxels as "bone", "implant", and "soft tissue" based on voxel intensities can be utilized to facilitate the automatic segmentation of bone and implants in post-operative images, which traditionally has been challenging due to several factors including: missing anatomy (e.g. resected bone); the presence of implants; the presence of voids due to surgery; and the presence of imaging artefacts due to metal in the imaging volume.

C. Autosegmentation of Anatomy in Post-Operative Images

This section uses the term "bone" as an example, but the modelling and segmentation algorithms are equally applicable to other anatomical structures, such as cartilage for example. The autosegmentation process described in this section may be applicable to the generation of the post-surgical bone model 158 shown in FIG. 6D.

The challenging factors listed in the preceding section may also be present in the autosegmentation of post-operative images where there exist bone, implants, and (possible) artefacts within the medical images. For example, the absence of bone where bone would be expected by the model (e.g., statistical model), or the presence of an implant or artefacts which would not be expected by the model may be challenging for traditional models and methods of segmentation. Appearance models, as described and employed herein, may be used to overcome these challenges. Following the approach described in the preceding section, voxels within the medical images which are labelled as implant, surgical void or imaging artefact are then tagged as Not Available or NA, as seen in FIG. 16. An appearance model may be used which ignores all such NA voxels in its computations whilst attempting to fit as usual to all other voxels. Thus, the appearance model may operate on an image, such as shown in FIG. 17, where certain voxels associated with the implant are ignored from the computation. Such models may be designated NA-aware or NAA.

Figure 6D:
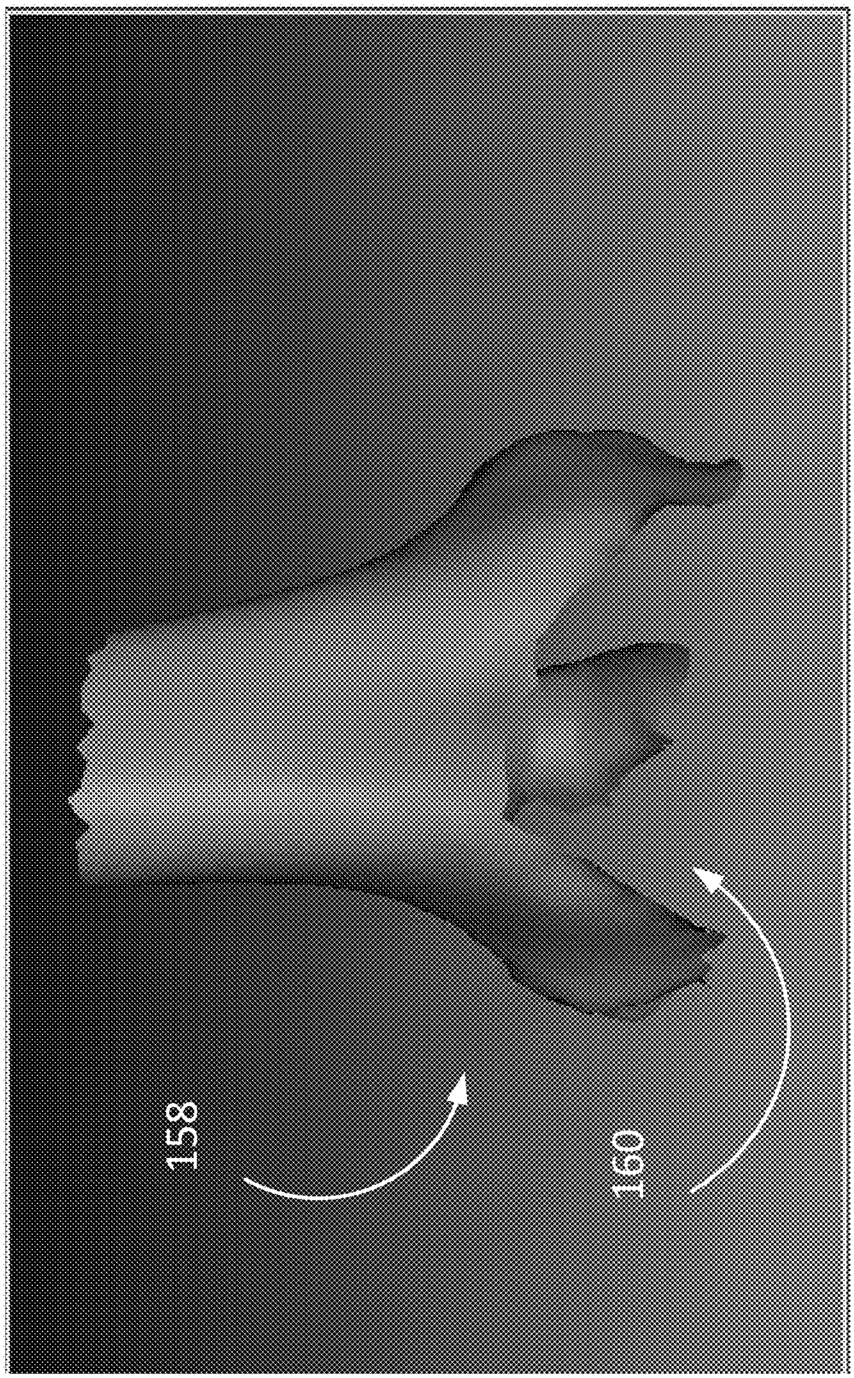
FIG. 6D is an anterior view of a postoperative three-dimensional bone-remainder model generated from the postoperative segmentation process.

The appearance model may be further modified in the particular case where the type of surgical procedure and class of implant is known, for example in accuracy measurements of patients. For example, if the patient has undergone a Total Knee Arthroplasty (TKA) with a Triathlon femoral component implanted, then the region of bone resected from the distal femur can be estimated from knowledge of similar procedures and the known dimensions of the Triathlon implant. For example, FIG. 6D shows the post-surgical bone model 158 generated from an autosegmentation process where the implant was known. The known implant can be used in the autosegmentation process as there may be a database of similar procedures performed using the same implant; thus, it can be estimated how the post-surgical bone is likely to appear. This prior knowledge can be incorporated into the statistical model explicitly during the training stage, or can be applied ad hoc by selecting a subset region of an existing appearance model, or by other modifications of the model algorithm. In all cases, the use of NAA models as described in the preceding paragraph means that this estimate of bone resection need not be particularly accurate; the NAA model can automatically segment the available bone quite accurately even when there are large deviations between the estimated and actual bone resections.

There may be enhancement to the autosegmentation algorithm for cases where the pre-operative CT image is available. In this case, the autosegmentation of the pre-operative bone is used to construct another variant of the appearance model used in the post-surgical autosegmentation process. In this case, it may be assumed that the patient's bone has not changed shape substantially from the time of the pre-operative image to the post-operative image. In this case, we can improve the autosegmentation of patient bone in the post-operative image by constructing a patient-specific autosegmentation model which is trained on that patient's pre-operative anatomy shape only. Such models may be designated as single-example (SE) models. Because this model is patient-specific, and combined with the enhancements of the preceding paragraphs, this model can autosegment the post-operative image with greater accuracy and robustness.

D. Autosegmentation of Implants in Post-Operative Images

The autosegmentation processes described in this section may be applicable to the generation of the implant model 166 shown in FIG. 7D. Appearance models may be used to autosegment the implants in the post-operative image. In the situation where there is a large training set of implant images, a population statistical model can be built in the same way as for the anatomy. When there are insufficient implant training images, a single-example SE model approach, as described in the preceding section, can be utilized. If the precise implant is known, because the surgery has just been performed for example, then a SE model may be constructed from an implant of specific type and size. If we do not know the implant type, then a succession of SE models from a database of known implants (i.e., including those from other manufacturers where the implant design is available) can be employed and the best result may be selected. In all cases, the image labelling procedure described in section VII.B. may be employed to enable the model to target the implant voxels whilst ignoring voxels which correspond to patient anatomy or background.

VIII. Exemplary Computing System

Figure 19:
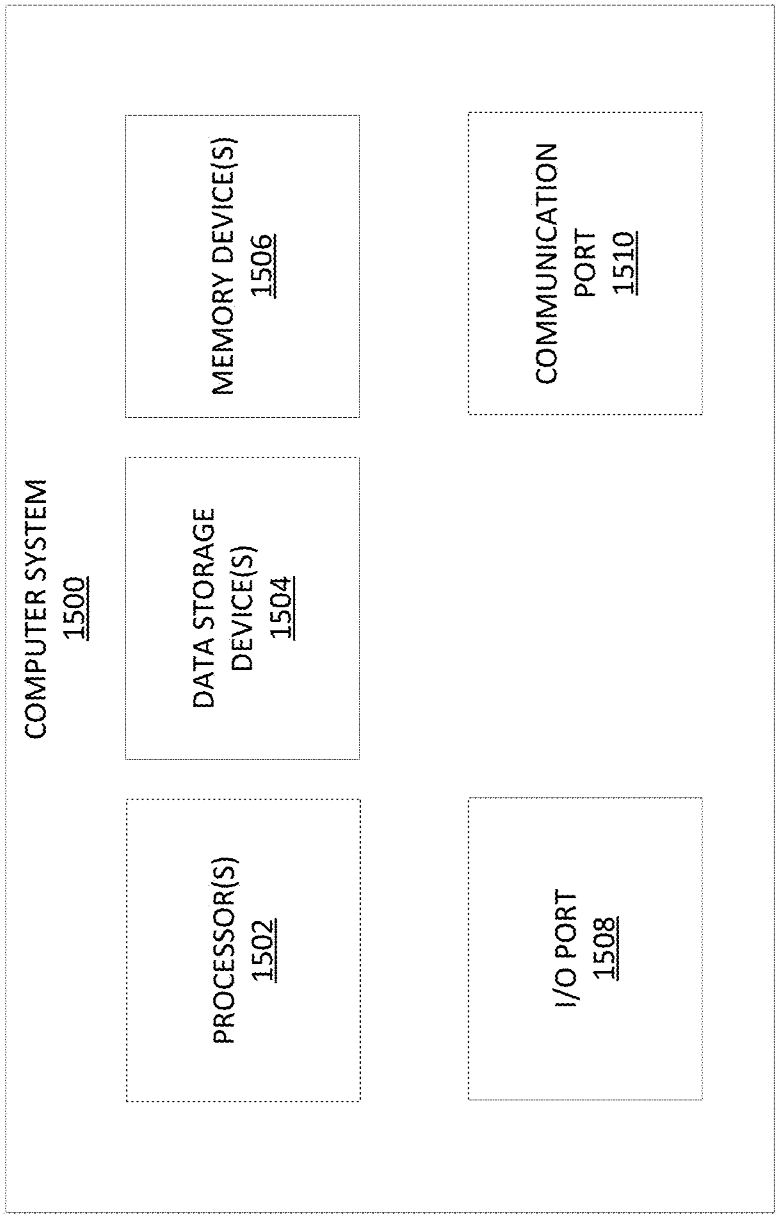
FIG. 19 is an example computing system having one or more computing units that may implement various systems and methods discussed herein is provided.

Referring to FIG. 19, a detailed description of an example computing system 1500 having one or more computing units that may implement various systems and methods discussed herein is provided. The computing system 1500 may be applicable to any of the computers or systems utilized in the preoperative planning and postoperative analysis of the arthroplasty procedure, and other computing or network devices. It will be appreciated that specific implementations of these devices may be of differing possible specific computing architectures not all of which are specifically discussed herein but will be understood by those of ordinary skill in the art.

The computer system 1500 may be a computing system that is capable of executing a computer program product to execute a computer process. Data and program files may be input to the computer system 1500, which reads the files and executes the programs therein. Some of the elements of the computer system 1500 are shown in FIG. 19, including one or more hardware processors 1502, one or more data storage devices 1504, one or more memory devices 1508, and/or one or more ports 1508-1510. Additionally, other elements that will be recognized by those skilled in the art may be included in the computing system 1500 but are not explicitly depicted in FIG. 19 or discussed further herein. Various elements of the computer system 1500 may communicate with one another by way of one or more communication buses, point-to-point communication paths, or other communication means not explicitly depicted in FIG. 19.

The processor 1502 may include, for example, a central processing unit (CPU), a microprocessor, a microcontroller, a digital signal processor (DSP), and/or one or more internal levels of cache. There may be one or more processors 1502, such that the processor 1502 comprises a single central-processing unit, or a plurality of processing units capable of executing instructions and performing operations in parallel with each other, commonly referred to as a parallel processing environment.

The computer system 1500 may be a conventional computer, a distributed computer, or any other type of computer, such as one or more external computers made available via a cloud computing architecture. The presently described technology is optionally implemented in software stored on the data stored device(s) 1504, stored on the memory device(s) 1506, and/or communicated via one or more of the ports 1508-1510, thereby transforming the computer system 1500 in FIG. 19 to a special purpose machine for implementing the operations described herein. Examples of the computer system 1500 include personal computers, terminals, workstations, mobile phones, tablets, laptops, personal computers, multimedia consoles, gaming consoles, set top boxes, and the like.

The one or more data storage devices 1504 may include any non-volatile data storage device capable of storing data generated or employed within the computing system 1500, such as computer executable instructions for performing a computer process, which may include instructions of both application programs and an operating system (OS) that manages the various components of the computing system 1500. The data storage devices 1504 may include, without limitation, magnetic disk drives, optical disk drives, solid state drives (SSDs), flash drives, and the like. The data storage devices 1504 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1506 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1504 and/or the memory devices 1506, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1500 includes one or more ports, such as an input/output (I/O) port 1508 and a communication port 1510, for communicating with other computing, network, or vehicle devices. It will be appreciated that the ports 1508-1510 may be combined or separate and that more or fewer ports may be included in the computer system 1500.

The I/O port 1508 may be connected to an I/O device, or other device, by which information is input to or output from the computing system 1500. Such I/O devices may include, without limitation, one or more input devices, output devices, and/or other devices.

In one implementation, the input devices convert a human-generated signal, such as, human voice, physical movement, physical touch or pressure, and/or the like, into electrical signals as input data into the computing system 1500 via the I/O port 1508. Similarly, the output devices may convert electrical signals received from computing system 1500 via the I/O port 1508 into signals that may be sensed as output by a human, such as sound, light, and/or touch. The input device may be an alphanumeric input device, including alphanumeric and other keys for communicating information and/or command selections to the processor 1502 via the I/O port 1508. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

In one implementation, a communication port 1510 is connected to a network by way of which the computer system 1500 may receive network data useful in executing the methods and systems set out herein as well as transmitting information and network configuration changes determined thereby. Stated differently, the communication port 1510 connects the computer system 1500 to one or more communication interface devices configured to transmit and/or receive information between the computing system 1500 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1510 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1510 may communicate with an antenna or other link for electromagnetic signal transmission and/or reception.

In an example implementation, patient data, bone models (e.g., generic, patient specific), transformation software, implant models, and other software and other modules and services may be embodied by instructions stored on the data storage devices 1504 and/or the memory devices 1506 and executed by the processor 1502. The computer system 1500 may be integrated with or otherwise form part of the surgical system 100.

The system set forth in FIG. 19 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed herein, for example, those shown in FIG. 5, among others, may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure including any of the methods described herein may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A method for determining accuracy of a surgical modification of a patient bone, the method comprising:

receiving first data comprising a planned surgical modification to the patient bone and images of the patient bone in a first condition at a first point in time;

receiving second data comprising images of the patient bone in a second condition at a second point in time subsequent to the first point in time and an attempt to implement the planned surgical modification;

comparing the second condition to the first condition;

assigning an outcome score based on the comparison of the second condition to the first condition, the outcome score conveying an extent to which the planned surgical modification was implemented; and storing the outcome score in a database for planning a further surgical modification of the patient bone, wherein planning the further surgical modification comprises accessing the database to retrieve the outcome score.

2. The method of claim 1, wherein comparing the second condition to the first condition comprises:

generating a computer model of the patient bone from the second data; and registering the computer model of the patient bone to the patient bone in the first data.

3. The method of claim 2, further comprising segmenting the images of the patient bone in the first data and using the segmented images to generate a computer model of the patient bone in the first condition at the first point in time.

4. The method of claim 3, wherein the planned surgical modification includes a surgical procedure to implant an implant on the patient bone, and wherein the method further comprises accessing a data base to retrieve a computer model of the implant and combining the computer model of the implant with the computer model of the patient bone in the first condition.

5. The method of claim 4, further comprising combining data pertaining to the planned surgical modification with the computer model of the implant and the computer model of the patient bone in the first condition.

6. The method of claim 1, wherein the planned surgical modification includes a surgical procedure to implant an implant on the patient bone.

7. The method of claim 6, wherein the first data includes implant position and orientation data associated with the planned surgical modification.

8. The method of claim 1, wherein the first point in time is preoperative to the planned surgical modification, and the second point in time is postoperative to the planned surgical modification.

9. The method of claim 1, further comprising segmenting the images of the patient bone in the second data and using the segmented images to generate a computer model of the patient bone in the second condition.

10. The method of claim 9, wherein the planned surgical modification includes a surgical procedure to implant an implant on the patient bone, and wherein segmenting the images of the patient bone in the second data further includes segmenting out an implant implanted onto the patient bone as part of the planned surgical modification.

11. The method of claim 10, wherein the segmenting out of the implant implanted onto the patient bone results in the computer model of the patient bone in the second condition having a void corresponding to a location of the implant.

12. The method of claim 9, wherein the planned surgical modification includes a surgical procedure to implant an implant on the patient bone, and the method further comprises accessing a computer model of the implant from a data base and combining the computer model of the implant with the computer model of the patient bone in the second condition.

13. The method of claim 1, wherein the planned surgical modification includes a surgical procedure to implant an implant on the patient bone, and wherein the method further comprises determining the extent to which the planned surgical modification was implemented by computing a difference between a position and orientation of the implant actually implanted and a planned implant position and orientation.

14. The method of claim 1, wherein the planned surgical modification includes a surgical procedure to implant an implant on the patient bone, and wherein the method further comprises displaying on a display screen the implant from the images of the patient bone in the second condition overlaid on the patient bone in the images of the patient bone in the first condition.

15. The method of claim 1, wherein the method is performed by a surgical navigation system in communication with at least one computing device.

16. The method of claim 1, wherein the method is performed by a surgical robot in communication with at least one computing device.

17. The method of claim 1, wherein the planned surgical modification includes a surgical procedure to implant an implant on the patient bone, and the patient bone is part of a patient knee, hip, ankle, shoulder or elbow.

18. The method of claim 1, further comprising using the outcome score stored in the database to segment surgical plans based on a projected patient outcome.

19. The method of claim 1, further comprising using the outcome score stored in the database to classify the further surgical modification based on a projected clinical outcome.

* * * * *